United States Patent
Avigad et al.

(10) Patent No.: US 10,557,173 B2
(45) Date of Patent: Feb. 11, 2020

(54) PROGNOSTIC METHODS, COMPOSITIONS AND KITS FOR PREDICTION OF ACUTE LYMPHOBLASTIC LEUKEMIA (ALL) RELAPSE

(71) Applicant: Mor Research Applications Ltd., Tel Aviv (IL)

(72) Inventors: Smadar Avigad, Tel Aviv (IL); Isaac Yaniv, Petach Tikva (IL)

(73) Assignee: MOR RESEARCH APPLICATIONS LTD., Tel Aviv (IL)

( * ) Notice: Subject to any disclaimer, the term of this patent is extended or adjusted under 35 U.S.C. 154(b) by 467 days.

(21) Appl. No.: 15/014,074

(22) Filed: Feb. 3, 2016

(65) Prior Publication Data

US 2016/0222464 A1 Aug. 4, 2016

Related U.S. Application Data

(63) Continuation-in-part of application No. 13/847,446, filed on Mar. 19, 2013.

(51) Int. Cl.
*C12Q 1/68* (2018.01)
*C12Q 1/6886* (2018.01)

(52) U.S. Cl.
CPC ...... *C12Q 1/6886* (2013.01); *C12Q 2600/118* (2013.01); *C12Q 2600/158* (2013.01); *C12Q 2600/178* (2013.01)

(58) Field of Classification Search
None
See application file for complete search history.

(56) References Cited

FOREIGN PATENT DOCUMENTS

WO 2008157319 12/2008

OTHER PUBLICATIONS

Mi et al; PNAS, vol. 104, pp. 19971-19976; 2007.*
Kramer; Curr. Protoc. Mol. Biol. vol. 95, 15.10.1-15.10.15; 2011.*
D Schotte et al, "Identification of new microRNA genes and aberrant microRNA profiles in childhood acute lymphoblastic leukemia", Leukemia, vol. 23, No. 2, 2008, pp. 313-322.
Kaddar T et al, "Prognostic value of miR-16 expression in childhood acute lymphoblastic leukemia relationships to normal and malignant lymphocyte proliferation", Leukemia Research, vol. 33, No. 9 2008., pp. 1217-1223.
X. Agirre et al, "Epigenetic Silencing of the Tumor Suppressor MicroRNA Hsa-miR-124a Regulates CDK6 Expression and Confers a Poor Prognosis in Acute Lymphoblastic Leukemia", Cancer Research, vol. 69, No. 10, pp. 4443-4453, 2009.
Lammens T et al, "MicroRNA Expression in Pediatric Precursor-B Acute Lymphoblastic Leukemia: Biology, Classification and Prognosis", Haematologica—The Hematology Journal, 15th Annual Meeting of the European-Hematology-Association; Barcelona, Spain; Jun. 10-13, 2010, vol. 95, No. Suppl. 2, p. 255.
Wang Y et al, "MicroRNAs expression signatures are associated with lineage and survival in acute leukemias", Blood Cells, Molecules and Diseases, vol. 44, No. 3, 2009, pp. 191-197.
Zhang Hua et al, "Genome-Wide Analysis of Small RNA and Novel MicroRNA Discovery in Human Acute Lymphoblastic Leukemia Based on Extensive Sequencing Approach", vol. 4, No. 9, 2009.
Montes-Moreno S et al, "MicroRNA Expression in DLBCL: Identification of Unique miRNAs Signatures Related to Clinical Outcome Prediction in R-CHOP Treated Patients", Laboratory Investigation, & 98th Annual Meeting of the United-States-and-Canadian-Academy-of-Path Ology; 2009 vol. 89, No. Suppl. 1, p. 278A.
Keller Andreas et al, "miRNAs in lung cancer—Studying complex fingerprints in patient's blood cells by microarray experiments", BMC Cancer, Biomed Central, vol. 9, No. 1, p. 353, 2009.
Ju Xiuli et al, "Differential microRNA Expression in Childhood B-Cell Precursor Acute Lymphoblastic Leukemia", Pediatric Hematology and Oncology, vol. 26, No. 1, pp. 1-10, 2009.
Hickey Christopher et al, "MicroRNA-181a Targets TEL/AML1 Expression and Impairs Cell Proliferation in t(12;21) Acute Lymphocytic Leukemia (ALL) Cells", Blood, 51st Annual Meeting of the American-Society-of-Hematology; New Orleans, LA, USA; Dec. 5-8, 2009, vol. 114, No. 22, p. 318.
Zhou et al, Oncology Reports, 23:121-128, 2010.
Bostjancic et al, Disease Markers 27:255-268, 2009.

* cited by examiner

*Primary Examiner* — Jehanne S Sitton
(74) *Attorney, Agent, or Firm* — JMB Davis Ben-David

(57) ABSTRACT

The present invention relates to prognostic methods and kits for the assessment and monitoring of relapse-free or disease-free survival of ALL patients. The detection is based on the use of detecting nucleic acids, specific for determination of the expression of at least one of miR-151-5p and miR-451 in a test sample. The invention thereby also provides methods and kits for monitoring and early diagnosis of cancerous disorders associated with low miR-151-5p and/or miR-451 expression, specifically ALL, and appropriate associated treatments thereof.

7 Claims, 14 Drawing Sheets

Specification includes a Sequence Listing.

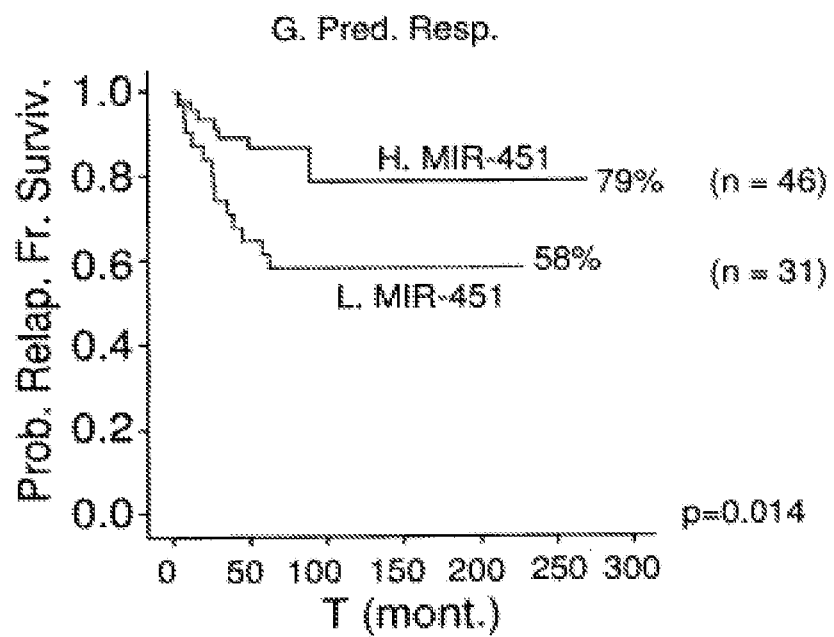
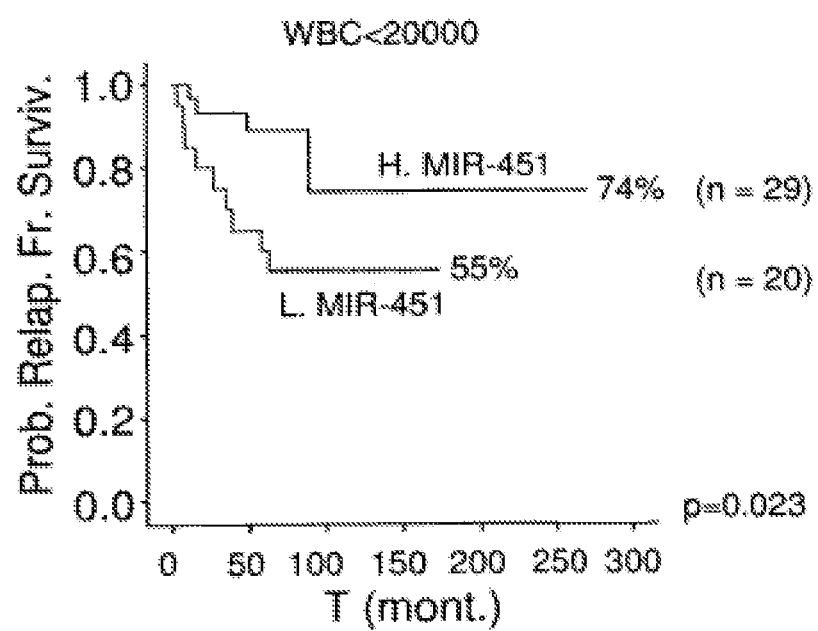

SEQUENCE LISTING

```
<160> NUMBER OF SEQ ID NOS: 7

<210> SEQ ID NO 1
<211> LENGTH: 21
<212> TYPE: RNA
<213> ORGANISM: Homo sapiens

<400> SEQUENCE: 1
ucgaggagcu cacagucuag u                                            21

<210> SEQ ID NO 2
<211> LENGTH: 22
<212> TYPE: RNA
<213> ORGANISM: Homo sapiens

<400> SEQUENCE: 2
aaaccguuac cauuacugag uu                                           22

<210> SEQ ID NO 3
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 3
gtcgtatcca gtgcagggtc cgaggtattc gcactggata cgacactaga            50

<210> SEQ ID NO 4
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 4
gtcgtatcca gtgcagggtc cgaggtattc gcactggata cgacaactca            50

<210> SEQ ID NO 5
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 5
ccagtgcagg gtccgaggta                                              20

<210> SEQ ID NO 6
<211> LENGTH: 24
<212> TYPE: DNA
<213> ORGANISM: Artificial Sequence
<220> FEATURE:
<223> OTHER INFORMATION: Synthetic Oligonucleotide
```

```
<400> SEQUENCE: 6
tcgaggagct cacagtctag tgtc                                          24

<210> SEQ ID NO 7
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 7
aaaccgttac cattactgag ttgtcg                                        26
```

PROGNOSTIC METHODS, COMPOSITIONS AND KITS FOR PREDICTION OF ACUTE LYMPHOBLASTIC LEUKEMIA (ALL) RELAPSE

CROSS REFERENCE TO RELATED APPLICATIONS

This is a Continuation-in Part of co-pending U.S. patent application Ser. No. 13/847,446, filed Mar. 19, 2013, which is the U.S. national stage of International Patent Application No. PCT/IL2011/00754, filed Sep. 25, 2011, which claims the benefit of U.S. Patent Application No. 61/387,864, filed Sep. 29, 2010. The contents of the foregoing applications are hereby incorporated by reference in their entirety.

FIELD OF THE INVENTION

The present invention relates to prognosis of Acute Lymphoblastic Leukemia (ALL) relapse. More specifically, the invention relates to the microRNAs miR-151-5p and miR-451, and their use, for the prognosis of ALL, monitoring and early diagnosis of ALL relapse.

BACKGROUND OF THE INVENTION

All publications mentioned throughout this application are fully incorporated herein by reference, including all references cited therein.

Leukemia is a cancer of the blood or bone marrow characterized by an abnormal increase of blood cells, usually leukocytes. Leukemia is clinically and pathologically subdivided into a variety of large groups. The first division is between its acute and chronic forms:

Acute leukemia is characterized by the rapid increase of immature blood cells. This crowding makes the bone marrow unable to produce healthy blood cells. Immediate treatment is required in acute leukemia due to the rapid progression and accumulation of the malignant cells, which then spill over into the bloodstream and spread to other organs of the body. Acute forms of leukemia are the most common forms of leukemia in children.

Chronic leukemia is distinguished by the excessive buildup of relatively mature, but still abnormal, white blood cells. Typically taking months or years to progress, the cells are produced at a much higher rate than normal cells, resulting in many abnormal white blood cells in the blood. Whereas acute leukemia must be treated immediately, chronic forms are sometimes monitored for some time before treatment to ensure maximum effectiveness of therapy. Chronic leukemia mostly occurs in older people, but can theoretically occur in any age group.

In 2000, approximately 256,000 children and adults around the world developed some form of leukemia, and 209,000 died as a result of it. About 90% of all leukemias are diagnosed in adults.

Pediatric leukemia is the most common type of malignancy in children. Among the leukemia subtypes, acute lymphoblastic leukemia (ALL) is the most frequent [Ries L A G et al., National Cancer Institute, SEER Program. NIH Pub. No. 99-4649. Bethesda, Md., 1999]. During the last 40 years accumulating data regarding the biology of pediatric ALL has improved the ability to assess the situation and adapt the most suitable treatment based on risk classification [Moghrabi A et al., Blood. (2007) 109: 896-904; Schultz K R et al., Blood. (2007); 109: 926-935; Möricke A et al., Leukemia. (2010); 24: 265-284; Gaynon P S et al., Leukemia. (2010); 24: 285-297; Stark B et al., Leukemia. (2010); 24: 419-424].

The Berlin-Frankfurt-Münster (BFM) and the Children Cancer Group (CCG) are examples of such classifications in which patients are divided into risk groups based on their white blood cells count (WBC), response to prednisone at day 8 (d8), age, leukemia cell type (B-lineage or T-cell) and the involvement of adverse chromosomal aberrations such as MLL-rearrangement t(4;11) or Philadelphia chromosome t(9;22) [Schrappe M, Ann Hematol. (2004); 83: S 121-3; Vrooman L M et al., Curr Opin Pediatr. (2009); 21(1):1-8]. Minimal residual disease (MRD) is an indication of the amount of remaining leukemic blasts in a patient's bone marrow (BM) during and/or after treatment, which can be measured by means of flow cytometry (FACS) and polymerase-chain reaction (PCR) [van Dongen J J M et al., Lancet. (1998); 352(9142):1731-1738; Bartram C R, Clin. Chim. Acta. (1993); 217: 75-83]. Currently, the BFM MRD-based protocol is regarded as the most accurate prediction of the chances for disease relapse [Möricke A et al., Leukemia. (2010); 24: 265-284]. Although current knowledge has improved the cure rate up to 80-90%, certain children are still over- or under-treated, resulting in treatment failure [Schrappe M et al., Leukemia. (2010); 24: 253-254; Pui C H and Evans W E, N. Engl. J. Med. (2006); 354: 166-178]. This illustrates the necessity of more knowledge regarding new aspects of ALL biology that will predict disease relapse more accurately. Genetic changes (e.g. Philadelphia chromosome) are already acknowledged as important contributors to ALL development [Smith M et al., J. Clin. Oncol. (1996); 14(1):18-24], however, little is known about the significance of epigenetic changes in pediatric ALL.

The findings presented here provide a link between ALL relapse rates and specific microRNAs (miRNAs or miRs) expression values. More specifically, the present invention demonstrates a link between expression values of miR-151-5p and miR-451, and relapse rates for pediatric ALL and B-ALL.

miRNAs are small (18-24 bp) non-coding RNA molecules that bind the 3' untranslated region (3' UTR) of mRNAs to prevent their translation [Bartel D P, Cell. (2004); 116: 281-297]. miRNAs function by either complete complementation with the 3' UTR that leads to mRNA degradation (similar to siRNA) or by incomplete complementation that results in translational inhibition [Meister G, Cell. (2007); 131: 25-28; He L and Hannon G J, Nat. Rev. Genet. (2004); 5: 522-531; Chen K and Rajewsky N, Nat. Rev. Genet. (2007); 8: 93-103]. The end result of both mechanisms is a decrease in specific protein level, which is thought to be a fine-tuning mechanism of protein expression. For this reason, miRNAs can function as pro-oncogenes or tumor suppressors by preventing the translation of tumor suppressors or oncogenes, respectively [Voorhoeve P M and Agami R, Biochim. Biophys. Acta. (2007). 1775(2):274-82; Chen C Z, N. Engl. J. Med. (2005); 353: 1768-1771; Esquela-Kercher A and Slack F J, Nature Rev. (2006); 6: 259-269].

In other types of malignant diseases the role of miRNAs was already investigated and certain miRNAs have already been linked to disease prognosis, disease profiling and even became interesting targets for therapy.

An example of such involvement of miRNAs can be demonstrated in normal and malignant hematopoeisis, where miRNA such as miR-150 contributes to normal lymphocytes development by changing its expression levels according to the phase of differentiation to regulate c-MYB translation [Xiao C et al, Cell. (2007); 131:146-59; Kluiver J et al., Leukemia. (2006); 20(11):1931-1936]. On the other hand, miR-150 and miR-96 were reported as downregulated and overexpressed, respectively, in CML [Agirre X et al., Mol Cancer Res (2008); 6(12):1830-1840]. As mentioned before, miRNAs may be used to classify diseases as demonstrated by Mi et al. [Proc. Natl. Acad. Sci. USA. (2007); 104(50):19971-19976] that showed how ALL can be distinguished from AML based on their miRNA profile. Mi et al. demonstrated that miR-451 expression is low in ALL in comparison with AML, thus generally attributing diagnostic, but not prognostic value to miRNA expression patterns in ALL.

Bandres E et al. [Clin. Cancer Res. 2009; 15(7) Apr. 1, 2009] provided a real-time PCR expression analysis of human mature miRNAs on paraffin-embedded tumor samples of gastric cancer stage III. Bandres identified the miRNAs correlated with disease-free and overall survival times, the results were evaluated using other patients, and in vitro cell proliferation and radio-sensitivity studies were performed to support clinical data. Bandres demonstrated that down-regulation of miR-451 was associated with worse prognosis. Over-expression of miR-451 in gastric and colorectal cancer cells reduced cell proliferation and increased sensitivity to radiotherapy. European Patent EP 2,196,543 disclosed methods and kits for prognosis of a predisposition to develop hepatocellular cancer, wherein one of the kits disclosed includes a probe for hsa-miR-451 for said prognosis. Agirre X., et al., [Mol. Cancer Res. 2008, 6(12), December 2008] identified miRNAs potentially implicated in chronic myeloid leukemia (CML). Agirre showed that out of 157 miRNAs tested in mononuclear cells (MNC) and $CD34^+$ cells from 6 patients with CML, hsa-miR-10a, hsa-miR-150, and hsa-miR-151 were down-regulated in CML, whereas hsa-miR-96 was up-regulated in CML cells, compared with cells isolated from healthy donors. Agirre thus showed that low hsa-miR-151 expression is a marker for CML diagnosis when comparing mononuclear cells (MNC) and $CD34^+$ from CML patients with cells derived from healthy patients.

However, stage III gastric cancer in mature, post-operative and post-chemotherapy/radiation therapy patients, hepatocellular cancer patients and CML (myeloid cell line cancer) patients cannot be compared with ALL (lymphoid cell cancer) patients.

Xiuli J. et al., [Ped. Hem. Oncol., 26:1-10, 2009] provided an informative profile of the expression of miRNAs in pre-B-ALL using two independent and quantitative methods: miRNA chip and qRT-PCR of mature miRNA from 40 newly diagnosed pre-B-ALL children. Both approaches showed that miR-222, miR-339, and miR-142-3p were dramatically overexpressed in pre-B-ALL patients, and down regulation of hsa-miR-451 and hsa-miR-373* was confirmed. Thus, Xiuli taught that miR-451 expression is down-regulated in pre-B-ALL patients, in comparison with healthy patients, but only based on a comparison of six healthy and six pre-B-ALL patients, i.e., a small number of patients suffering from B-ALL. Based on this data, Xiuli showed that miR-451 down-regulation is diagnostic of pre-B-ALL, but, as with Mi et al., it was not mentioned or even hinted that miR-451 down regulation is prognostic for B-ALL patients' relapse. Furthermore, the present inventors did not observe a difference in miR-451 expression in B- and T-ALL samples. Specifically, 45% (30/67) and 54% (15/28) of all B-ALL and T-ALL samples, respectively, showed low miR-451 expression, and therefore, according to the present invention it is impossible to discern T-ALL from B-ALL based on miR-451 expression level.

Finally, Fulci V., et al., [Genes, Chromosomes & Cancer 48:1069-1082 (2009)] investigated miRNAs expression profiles in adult ALL patients. miRNA expression was determined by microarray analysis and identified miR-148, miR-151, and miR-424 as discriminative of T-lineage versus B-lineage ALL. While this agrees with some of the inventors' findings, Fulci had found a statistical correlation between miR-151 and B-ALL, but did not make the connection to relapse risk as a function of miR-151 expression.

In pediatric ALL, little is known about the biological role of miRNA and the link between them and ALL was rarely investigated [Schotte D et al., Leukemia. (2009); 23: 313-322]. For this reason, this study focuses on finding miRNA that are involved in pediatric ALL biology with main emphasis on disease relapse. Possible correlation to clinical parameters is sought and potential implementation of those miRNA in disease risk-assessment is evaluated.

The present invention focuses on miRNAs that are involved in pediatric ALL biology, namely miR-451 and miR-151-5p, as well as any combinations thereof, with main emphasis on disease relapse. The inventors demonstrate a correlation between said miRNA expression patterns and clinical parameters allowing the implementation of novel, more accurate risk assessment procedures for ALL relapse. Furthermore, the present invention allows the prognosis to take place at initial diagnosis, rather than later when dependent on diagnostic methods which require lengthy periods. This allows for an early identification of the relapse risk of the patient and the administration of an optimal treatment.

Therefore, one object of the invention is to provide prognostic methods, compositions and kits for the prognosis of ALL.

A more specific object of the invention is to provide prognostic methods, compositions and kits for the prognosis of ALL, monitoring and early detection or diagnosis of ALL relapse, which allow an early accurate prognosis of ALL and provides the necessary information for directing an appropriate treatment regimen from initial diagnosis.

These and other objects of the invention will become apparent as the description proceeds.

SUMMARY

In the first aspect, the present invention provides a method for the prognosis of acute lymphoblastic leukemia (ALL) and monitoring and/or early diagnosis of ALL relapse in a mammalian subject. The method of the invention comprises the steps of: (a) contacting detecting nucleic acid molecules specific for at least one of miR-151-5p and miR-451 and for at least one suitable control reference gene or miRNA, with a test sample of the subject or with any nucleic acid product obtained therefrom and optionally with a suitable control sample. The second step (b) involves determining the expression value of at least one of miR-151-5p, and miR-451 in the test sample, and optionally, in a suitable control sample; and (c) determining the expression value of at least one suitable control reference gene or miRNA in the test sample, and optionally, in a suitable control sample. In the next step (d) the expression values of the at least one of miR-151-5p, and miR-451 obtained in step (b) are normalized according to the expression value of the least one suitable control reference gene or miRNA obtained in step (c). In the next step (e) comparing the at least one normalized expression value obtained in step (d) with a corresponding predetermined cutoff value or with a normalized expression value of at least one of miR-151-5p, and miR-451 obtained from a suitable control sample according to step (b). It should be noted that a positive expression value of at least one of the miR-151-5p, and miR-451 indicates that the subject belongs to a pre-established ALL patient population associated with a specific relapse rate, the relapse rate is higher than the specific relapse rate associated with the pre-established ALL patient population where a corresponding at least one of the miR-151-5p and miR-451 has a negative expression value.

It should be noted that the presence of at least one of said miR-151-5p, and miR-451 with a positive expression value indicates that the subject belongs to a pre-established ALL patient population associated with a specific relapse rate that is higher than the specific relapse rate associated with the pre-established ALL patient population where a corresponding at least one of the miR-151-5p and miR-451 has a negative expression value.

Furthermore, according to specific embodiments of the invention, said positive expression value indicates that the subject belongs to a pre-established ALL patient population associated with a more accurate specific relapse rate than current clinical or biological methods could detect.

In the second aspect, the present invention contemplates a prognostic composition for the prognosis of ALL, monitoring, prediction or early detection of ALL relapse. The composition of the invention may comprise detecting nucleic acid molecules specific for determination of the expression of at least one of miR-151-5p and miR-451 and of at least one control reference gene or miRNA, the composition is for determining the expression value of at least one of miR-151-5p and miR-451 in a biological test sample of a mammalian subject.

In a further aspect, the present invention relates to a prognostic and/or a diagnostic kit for prognosis of ALL, monitoring and/or early diagnosis of ALL relapse in a mammalian subject. The kit of the invention comprises: (a) detecting molecules specific for determining the expression of at least one of miR-151-5p and miR-451; (b) detecting molecules specific for determining the expression of at least one control reference gene or miRNA; (c) optionally, at least one control sample selected from a negative control sample and a positive control sample; (d) optionally, instructions for carrying out the detection and quantification of expression of the at least one of miR-151-5p and miR-451 and of at least one control reference gene or miRNA in the sample, and for obtaining an expression value of each of the at least one of miR-151-5p and miR-451; (e) optionally, pre-determined calibration curve providing normalized expression values of the at least one of miR-151-5p and miR-451; and (f) instructions for comparing the expression values of at least one of the miR-151-5p and miR-451 in the test sample with a corresponding predetermined cutoff value of each the at least one of miR-151-5p and miR-451 or with a normalized expression value of at least one of miR-151-5p, and miR-451 obtained from a suitable control sample according to (c).

In the last aspect, the present invention relates to a method of preventing or delaying the relapse of ALL relapse, comprising the step of administering to a subject in need thereof a therapeutically effective amount of at least one of miR-151-5p and miR-451 or any gene encoding the at least one of miR-151-5p and miR-451, pri-miRNA, pre-miRNA thereof, a construct encoding the at least one of miR-151-5p and miR-451, any combinations thereof or any composition comprising the same.

These and other aspects of the invention will become apparent as the description proceeds.

BRIEF DESCRIPTION OF THE FIGURES

FIG. 1A: RFS for 95 ALL patients in correlation with miR-151-5p. Out of 47 high miR-151-5p samples, 9 relapsed. Out of 48 low miR-151-5p samples, 22 relapsed. FIG. 1B: RFS for the 95 ALL patients in correlation with miR-451. Out of 50 high miR-451 samples, 10 relapsed. Out of 45 low miR-451 samples, 21 relapsed. FIG. 1C: RFS for 95 ALL patients in correlation with both miR-151-5p and miR-451. Out of 31 high miR-151-5p and miR-451 samples, 4 relapsed. Out of 65 samples in which at least one of miR-151-5p and miR-451 are low, 27 relapsed. Abbreviations: H. miR-151-5p (high miR-151-5p expression); L. miR-151-5p (low miR-151-5p expression); H. miR-451 (high miR-451 expression); L. miR-451 (low miR-451 expression); Bot. Hig. (both high); A. Leas. On. Lo. (at least one low); T (mont.) (time (months)); Prob. Relap. Fr. Surviv. (probability of relapse-free survival).

FIG. 2A: RFS for 67 B-ALL patients in correlation with miR-151-5p. Out of 44 high miR-151-5p samples, 7 relapsed. Out of 23 low miR-151-5p samples, 13 relapsed. FIG. 2B: RFS for 67 B-ALL patients in correlation with miR-451. Out of 37 high miR-451 samples, 5 relapsed. Out of 30 low miR-451 samples, 15 relapsed. FIG. 2C: RFS for 67 B-ALL patients in correlation with both miR-151-5p and miR-451. Out of 28 high miR-151-5p and miR-451 samples, 2 relapsed. Out of 39 samples in which at least one of miR-151-5p and miR-451 are low, 18 relapsed. Abbreviations: H. miR-151-5p (high miR-151-5p expression); L. miR-151-5p (low miR-151-5p expression); H. miR-451 (high miR-451 expression); L. miR-451 (low miR-451 expression); Bot. Hig. (both high); A. Leas. On. Lo. (at least one low); T (mont.) (time (months)); Prob. Relap. Fr. Surviv. (probability of relapse-free survival).

FIG. 3A: RFS for 43 ALL patients in correlation with miR-151-5p. Out of 27 high miR-151-5p samples, 1 relapsed. Out of 16 low miR-151-5p samples, 4 relapsed. FIG. 3B: RFS for 32 B-ALL patients out of the 43 ALL patients in correlation with miR-151-5p. Out of 25 high miR-151-5p samples, none relapsed. Out of 7 low miR-151-5p samples, 2 relapsed. In total, out of 32 B-ALL patients, 2 relapsed. FIG. 3C RFS for 32 B-ALL patients out of the 43 ALL patients in correlation with miR-451. Out of 24 high miR-451 samples, none relapsed. Out of 8 low miR-451 samples, 2 relapsed. Abbreviations: H. miR-151-5p (high miR-151-5p expression); L. miR-151-5p (low miR-151-5p expression); H. miR-451 (high miR-451 expression); L. miR-451 (low miR-451 expression); T (mont.) (time (months)); Prob. Relap. Fr. Surviv. (probability of relapse-free survival).

FIG. 4A: RFS for 49 ALL patients with a white blood cells (WBC) count under 20,000 in correlation with miR-151-5p. FIG. 4B: RFS for 77 ALL patients showing a good prednisone response on day 8 (d8) in correlation with miR-151-5p. Abbreviations: H. miR-151-5p (high miR-151-5p expression); L. miR-151-5p (low miR-151-5p expression); T (mont.) (time (months)); Prob. Relap. Fr. Surviv. (probability of relapse-free survival); WBC<20000 (white blood count<20000); G. Pred. Resp. (good prednisone responders).

FIG. 5A-5C: Kaplan Meier estimation of Relapse Free Survival (RFS) by miR-451 expression in cohort of ALL and B-ALL patients classified according to favorable prognostic factors. Probability of relapse-free survival in months from diagnosis commencement is shown. FIG. 5A: RFS for 42 female ALL patients in correlation with miR-451. FIG. 5B: RFS for 77 ALL patients showing a good prednisone response on day 8 (d8) in correlation with miR-451. FIG. 5C: RFS for 49 ALL patients with a WBC under 20,000 in correlation with miR-45. Abbreviations: H. miR-451 (high miR-451 expression); L. miR-451 (low miR-451 expression); T (mont.) (time (months)); Prob. Relap. Fr. Surviv. (probability of relapse-free survival); Fem. (females); WBC<20000 (white blood count<20000); G. Pred. Resp. (good prednisone responders).

FIG. 6A: RFS for 83 B-ALL patients in correlation with miR-151-5p. Out of 59 high miR-151-5p samples, 11 relapsed. Out of 24 low miR-151-5p samples, 12 relapsed. FIG. 6B: RFS for 88 B-ALL patients in correlation with miR-451. Out of 49 high miR-451 samples, 7 relapsed. Out of 39 low miR-451 samples, 16 relapsed. FIG. 6C: RFS for 80 B-ALL patients in correlation with both miR-151-5p and miR-451. Out of 65 high miR-151-5p and miR-451 samples, 14 relapsed. Out of 15 samples in which at least one of miR-151-5p and miR-451 are low, 9 relapsed. FIG. 6D: RFS for 84 B-ALL patients in correlation with miR-151-5p and miR-451. Out of 37 patients where both miR-151-5p and miR-451 were expressed in high levels, 4 relapsed. Out of 47 patients where at least one of miR-151-5p and miR-451 were expressed in low levels, 19 relapsed.

Abbreviations: H. miR-151-5p (high miR-151-5p expression); L. miR-151-5p (low miR-151-5p expression); H. miR-451 (high miR-451 expression); L. miR-451 (low miR-451 expression); Bot. Lo. (both low); A. Leas. On. Lo. (at least one low); A. Leas. On. Hig. (at least one high); T (mont.) (time (months)); Prob. Relap. Fr. Surviv. (probability of relapse-free survival).

Figure 3A:
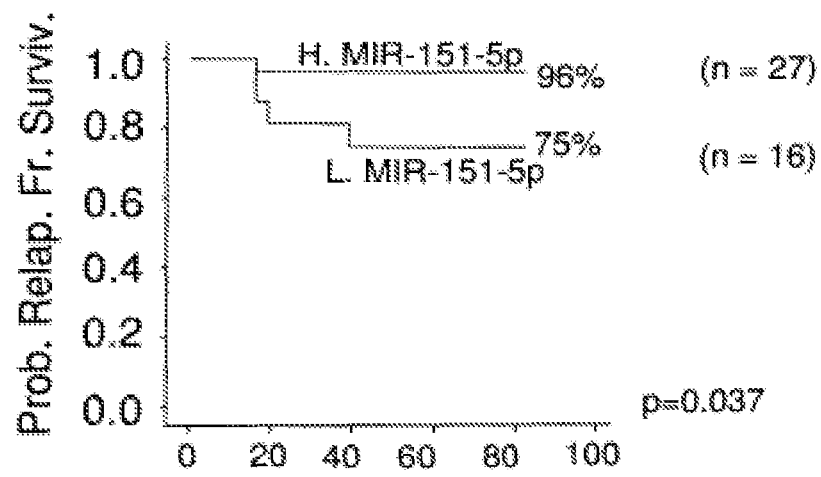
FIG. 3A-3C: Kaplan Meier estimation of Relapse Free Survival (RFS) in the MRD-defined non-high risk cohort of ALL and B-ALL patients. Probability of relapse-free survival in months from diagnosis commencement is shown.
Figure 3B:
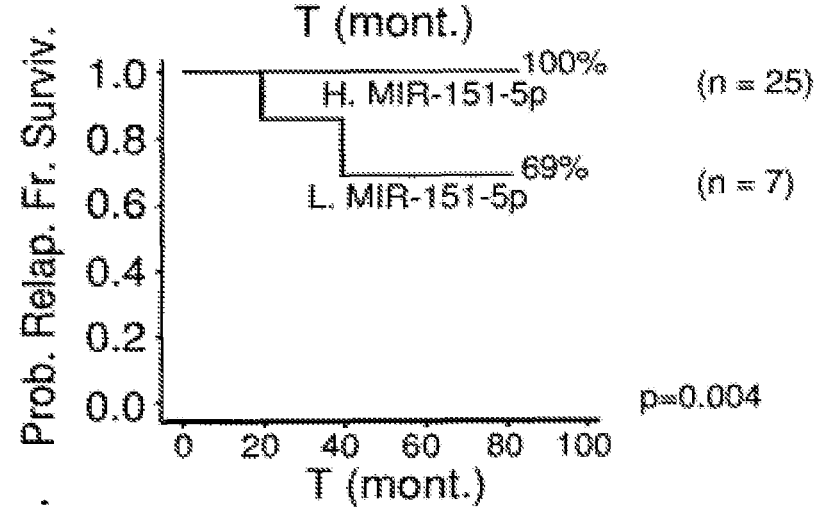
Figure 3C:
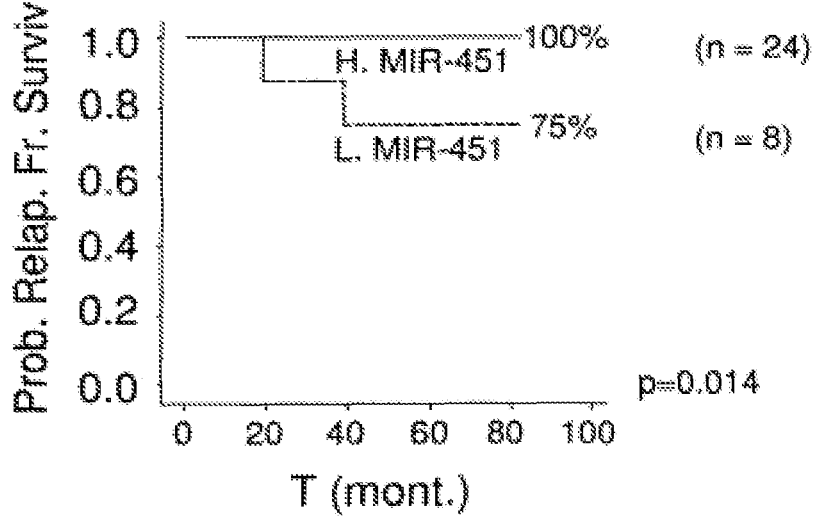
Figure 7A:
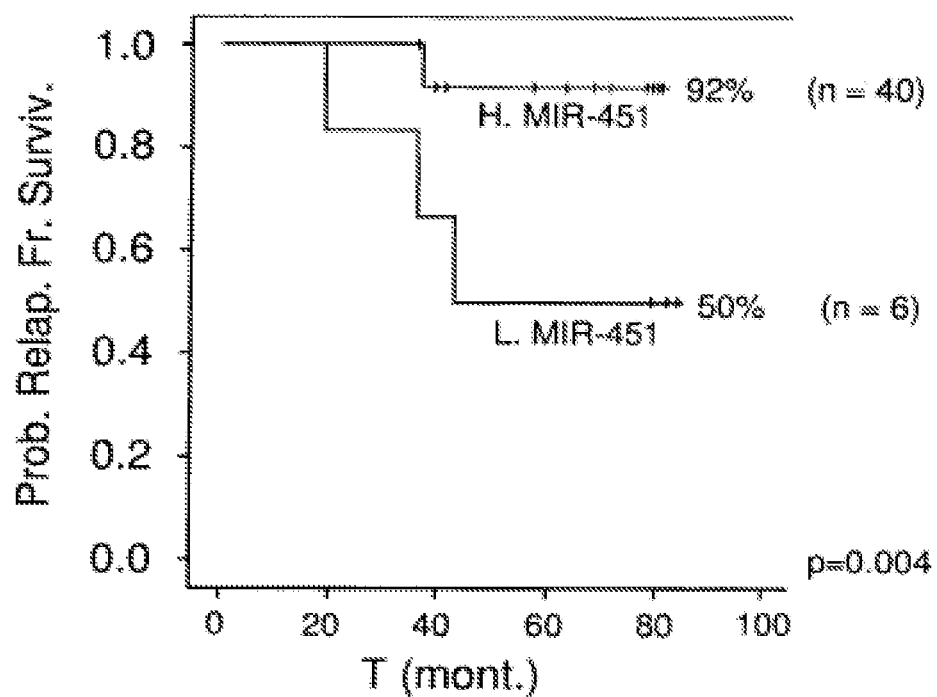
Figure 7B:
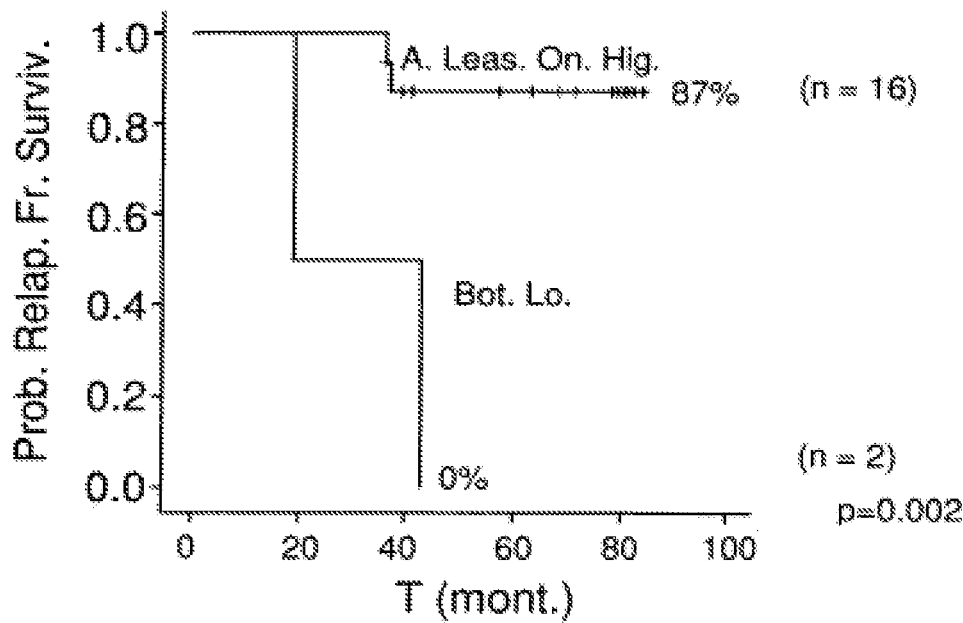

FIG. 7A-7B: Prognostic relevance of miR-151-5p and miR-451 expression in an extended cohort in patients classified as non-high risk according to PCR-MRD Probability of relapse-free survival in months from diagnosis commencement is shown. The figure provides an analysis of the original patient population (which is presented in FIG. 3) augmented by the addition of more patients (extended cohort), and classified as non-high risk according to PCR-MRD FIG. 7A: non-high risk group RFS for 46 B-ALL patients classified as non-high risk according to PCR-MRD in correlation with miR-451. Out of 40 high miR-451 samples, 3 relapsed. Out of 6 samples in which miR-451 was low, 3 relapsed. FIG. 7B: intermediate risk group RFS for 18 B-ALL patients classified as intermediate-risk according to PCR-MRD in correlation with miR-151-5p and miR-451 (both low). Out of 16 high miR-151-5p and miR-451 samples, 2 relapsed. Out of 2 samples in which miR-151-5p and miR-451 were both low, all relapsed.

Abbreviations: H. miR-151-5p (high miR-151-5p expression); L. miR-451 (low miR-451 expression); Bot. Lo. (both low); A. Leas. On. Hig. (at least one high); T (mont.) (time (months)); Prob. Relap. Fr. Surviv. (probability of relapse-free survival).

Figure 8:
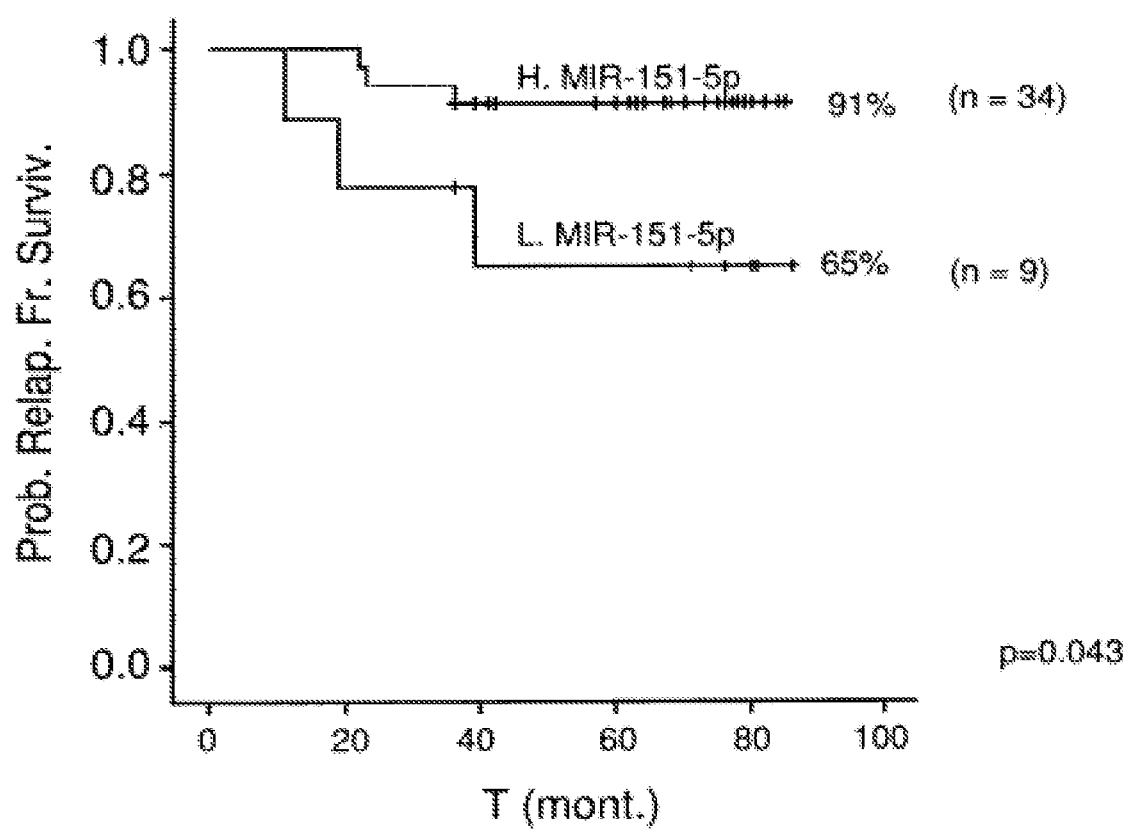

FIG. 8: Analysis of cohort following exclusion of Ikaros deletion and/or P2RY8-CRLF2 rearrangement Probability of relapse-free survival in months from diagnosis commencement is shown. RFS for 43 B-ALL patients not suffering from Ikaros deletion and/or P2RY8-CRLF2 rearrangement, in correlation with miR-151-5p. Out of 34 high miR-151-5p samples, 3 relapsed. Out of 9 low miR-151-5p samples, 3 relapsed.

Abbreviations: H. miR-151-5p (high miR-151-5p expression); L. miR-151-5p (low miR-151-5p expression); T (mont.) (time (months)); Prob. Relap. Fr. Surviv. (probability of relapse-free survival).

Figure 9:
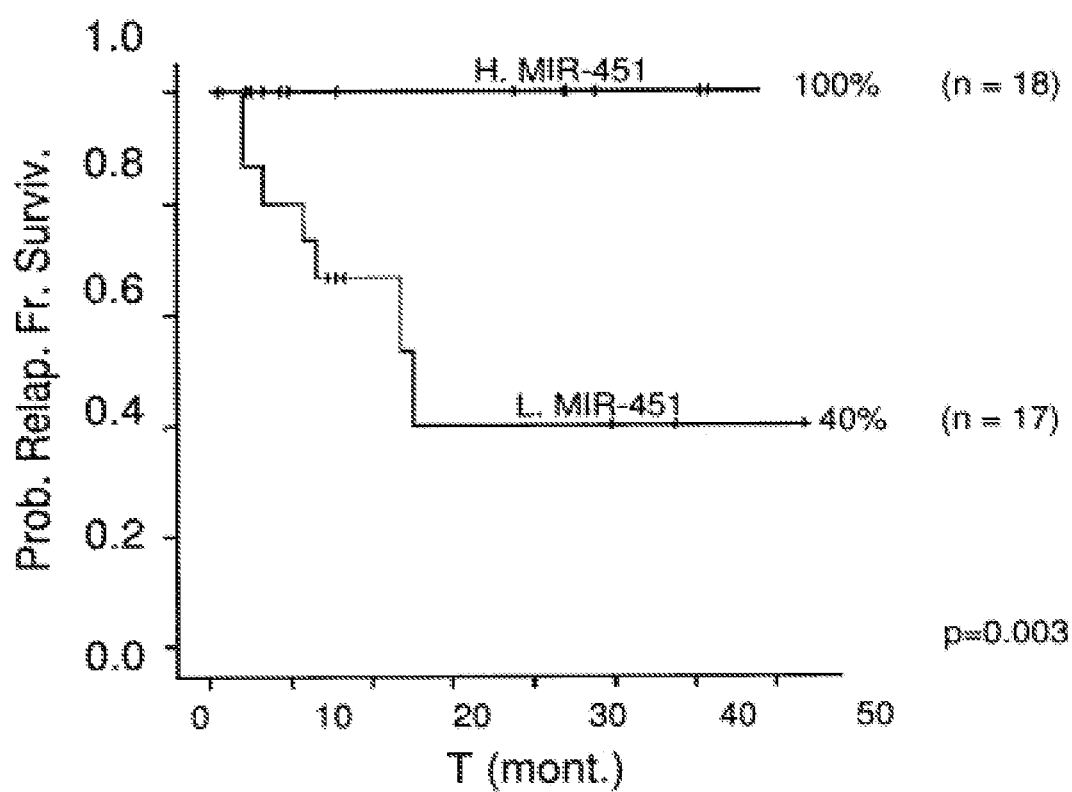

FIG. 9: Validation of miR-451 as a relapse prognostic marker in B-ALL patients undergoing a Dutch Childhood Oncology Group (DCOG) protocol ALL-9 treatment regimen Probability of relapse-free survival in months from diagnosis commencement is shown. RFS for 35 B-ALL patients undergoing a Dutch Childhood Oncology Group (DCOG) protocol ALL-9 treatment regimen in correlation with miR-451. Out of 18 high miR-451 samples, none relapsed. Out of 17 samples in which miR-451 is low 7 patients relapsed.

Abbreviations: H. miR-451 (high miR-451 expression); L. miR-451 (low miR-451 expression); T (mont.) (time (months)); Prob. Relap. Fr. Surviv. (probability of relapse-free survival).

Figure 10A:
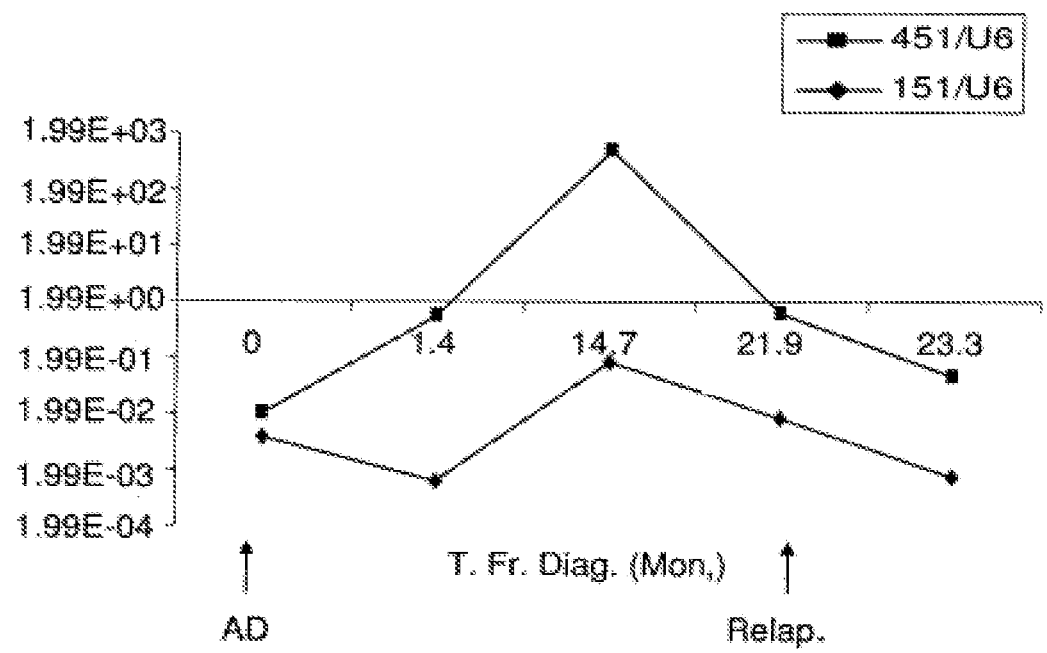
Figure 10B:
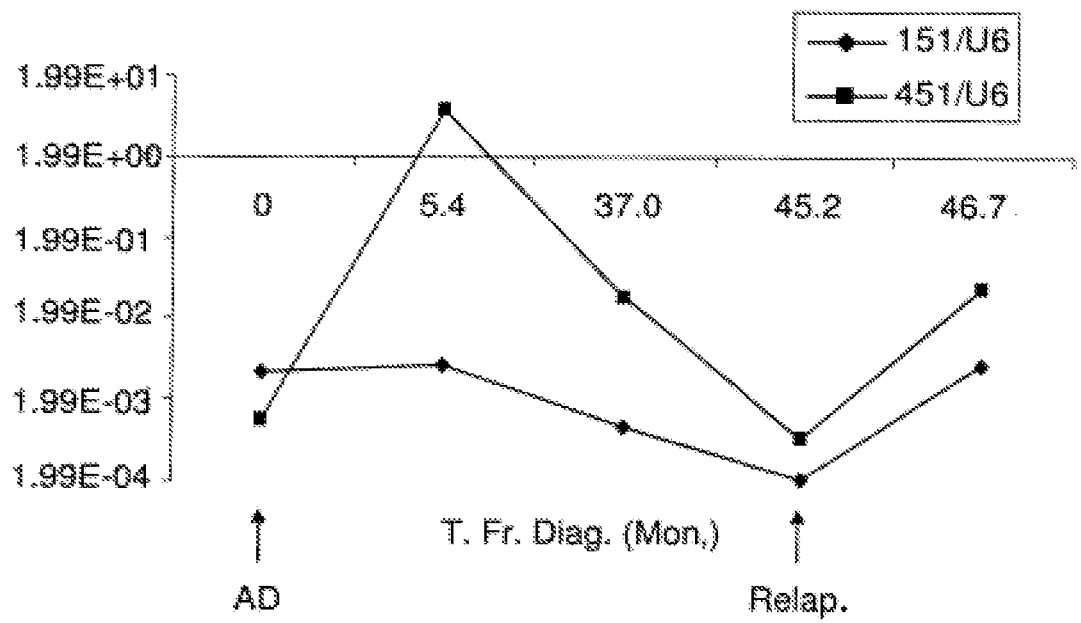
Figure 10C:
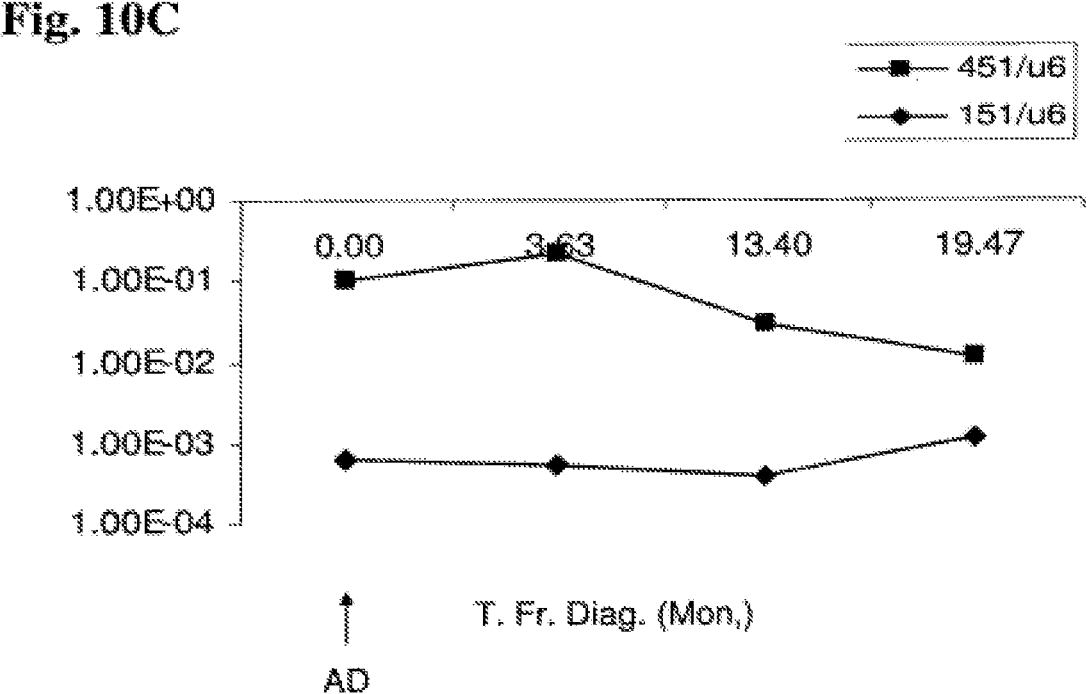
Figure 10D:
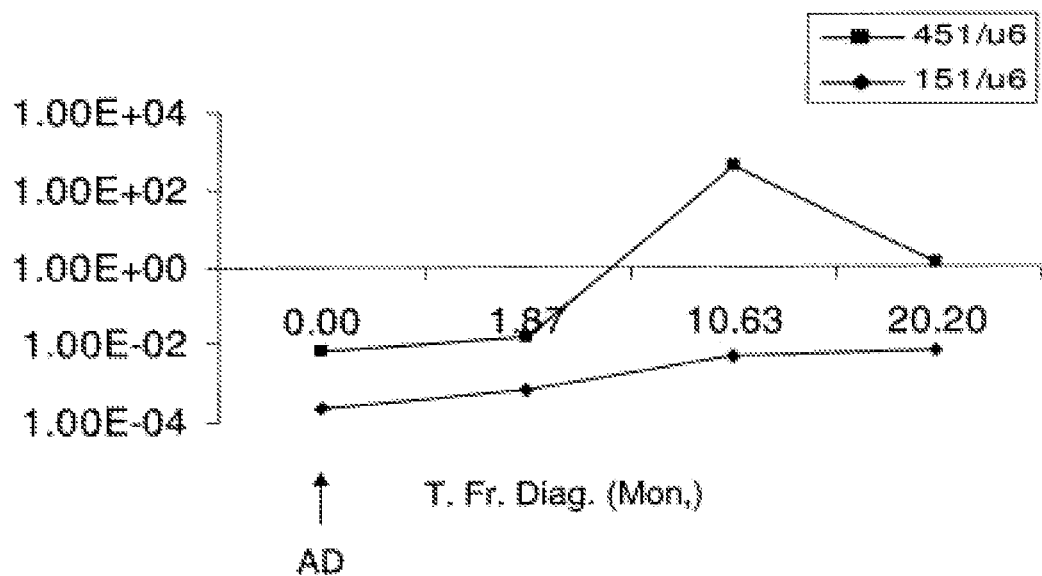

FIG. 10A-10D: Time-course analysis of miR-151-5p and miR-451 expression from diagnosis onwards Expression of miR-151-5p and miR-451 as a function of time elapsing from diagnosis in four patients are shown: 2 patients that relapsed (A and B) and 2 patients that are well during a long follow up (C and D). Expression values shown are normalized expression values (marker/U6 control). FIG. 10A: miR-151-5p and miR-451 expression pattern in patient A. FIG. 10B: miR-151-5p and miR-451 expression pattern in patient B. FIG. 10C: miR-151-5p and miR-451 expression pattern in non-relapse patient C. FIG. 10D: miR-151-5p and miR-451 expression pattern in non-relapse patient D. Abbreviations: T. Fr. Diag. (Mon.) (time from diagnosis (months)); AD (at diagnosis); Relap. (relapse).

Figure 11:
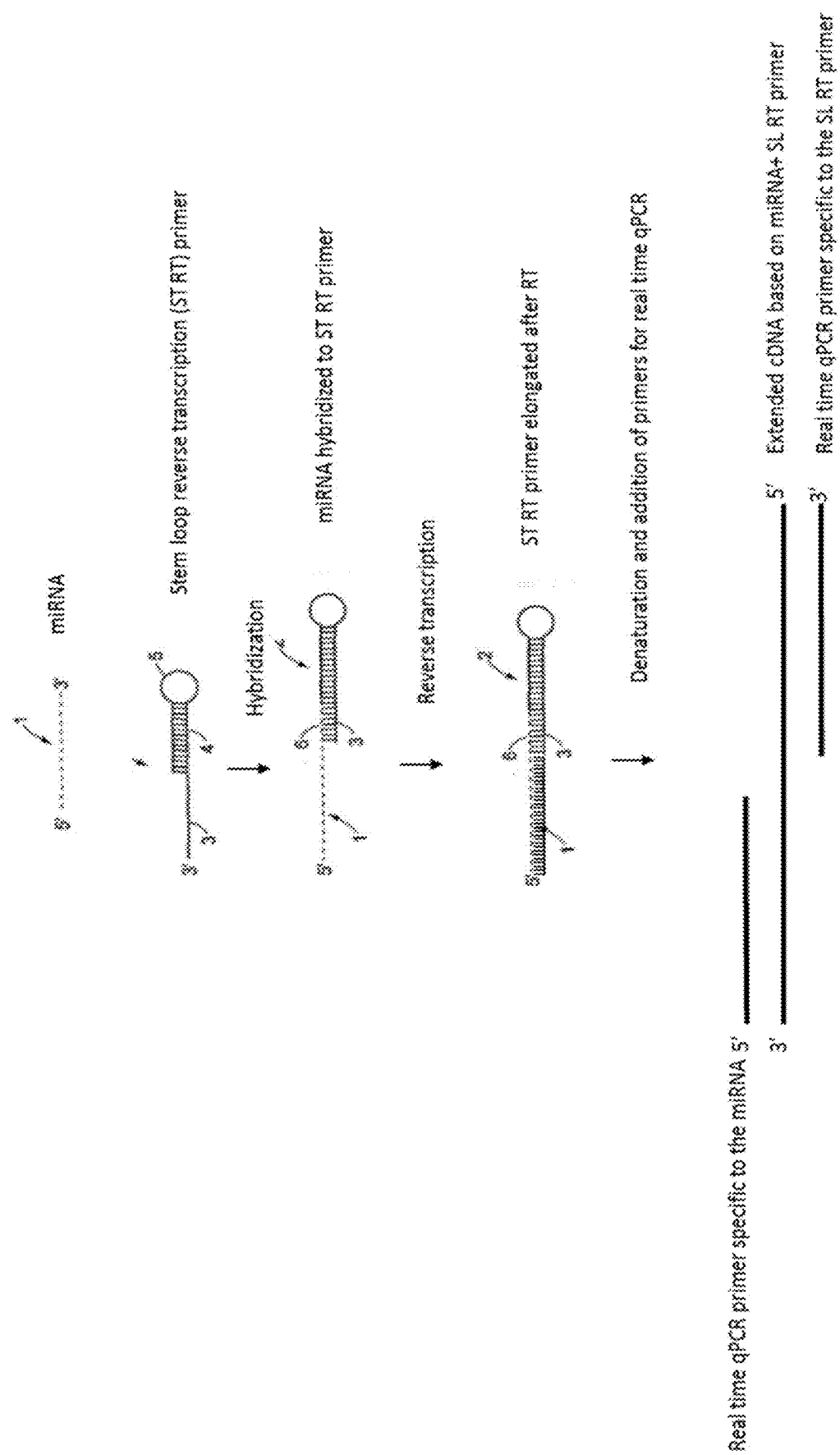

FIG. 11: schematic overview of miRNA amplification by RT-qPCR, using a stem-loop oligonucleotide primer.

BRIEF DESCRIPTION OF THE DESCRIBED SEQUENCES

The nucleic acid sequences provided herewith are shown using standard letter abbreviations for nucleotide bases as defined in 37 C.F.R. 1.822. Only one strand of each nucleic acid sequence is shown, but the complementary strand is understood as included by any reference to the displayed strand. The Sequence Listing is submitted as an ASCII text file named 3044_11_3001_seq_list_ST25.txt, created Feb. 2, 2016, about 1.5 KB, which is incorporated by reference herein. In the accompanying sequence listing:

SEQ ID NO: 1 is the nucleotide sequence of miR-151-5p.
SEQ ID NO: 2 is the nucleotide sequence of miR-451.
SEQ ID NO: 3 is the nucleotide sequence of a stem loop reverse transcription DNA primer for miR-151-5p.
SEQ ID NO: 4 is the nucleotide sequence of a stem loop reverse transcription DNA primer for miR-451.
SEQ ID NO: 5 is the nucleotide sequence of a forward general stem-loop primer.

SEQ ID NO: 6 is the nucleotide sequence of a reverse primer for miR-151-5p.

SEQ ID NO: 7 is the nucleotide sequence of a reverse primer for miR-451.

DETAILED DESCRIPTION

The most significant cause of treatment failure is disease relapse; this fact is true for both adult and pediatric hematological malignancies. Prediction of relapse has proved to be the key for successful treatment of pediatric ALL, although improvements have been made in the last ten years, it is still very difficult if not impossible to determine at the time of diagnosis which patients would eventually relapse. In the present invention, a cohort of 95 bone marrow samples of ALL patients from the day of diagnosis was analyzed for miRNA expression. Two particular miRNAs, miR-151-5p and miR-451 seemed to have lower expression in patients that eventually relapsed. These two miRNAs also correlated to other clinical risk factors like poor prednisone response. The inventors also analyzed an extended cohort, as well as a group of patients undergoing a different therapeutic regimen, and thus demonstrated the applicability of the invention to other patient groups which are not necessarily treated according to the INS-84, INS-89, INS-98 and INS-2003 protocols-which are BFM based treatments.

To date, this is the first study that attempts to correlate specific miRNAs to disease relapse, although correlation to other factors e.g. MLL-rearrangement or other cytogenetic aberrations were already reported in pediatric ALL [Schotte D et al., Leukemia. (2009); 23: 313-322; Schotte D et al., Blood. (2009); 114(22):41 abstract 89]. Since low expression level of those miRNAs correlated with worse prognosis, it has been assumed that they target oncogenes that might play a role in ALL carcinogenesis. Other publications already indicated that miR-451 has anti-neoplastic function in glioma and gastrointestinal tumors [Gal H et al., Biochem. Biophys. Res. Commun. (2008); 376(1):86-90; Bandres E et al., Clin Cancer Res. (2009); 15(7):2281-2290], while the role of miR-151-5p is less understood and seems to be tumor type dependent [Ding J et al., Nature Cell. Bio. (2010); 12(4):390-400]. Based on bioinformatics tools (e.g. target scan and target rank) potential targets of those miRNAs were sought. miR-151-5p was predicted to target oncogenes like WNT1, KIT and PAX2, which are known contributors to the malignant phenotype of leukemia in general. miR-451 was predicted to target ADAM10, a metallopeptidase known to cleave many proteins like TNF-α and E-cadherin. Due to technical reasons, validation of those potential targets was not achieved and so nothing could be said about the biological role of miR-151-5p and miR-451. However, this does not diminish their significant ability to predict at the day of diagnosis which child would relapse.

As mentioned before, even with the most advanced technology and risk assessment protocols, about 25% of the cases would eventually relapse [Pui C H et al., Leukemia. (2010); 24(2):371-382]. Although the majority of relapse cases occur in HR (high risk) groups, it is far from being exclusive to this group [Conter V et al., Blood. (2010); 115(16)3206-3214]. This means that many patients that are classified as either IR (intermediate risk) or SR (standard risk) should have actually been classified as HR and received a more intensive treatment. In fact, according to Conter et al., the relapse rate for IR patients is as high as 22.4% and for SR patients is 7.7%. Here, the inventors demonstrated how miRNA can help identify those that are truly at risk among all the patients that are classified as intermediate or non-HR and need to receive the intense high risk treatment regimen. When compared to other routinely used risk classification methods (e.g. the BFM), it appears that the combination of miR-151-5p and miR-451 provides identification of patients at risk just as well as the entire BFM-system and adds unique information on the patient that is not found in other available prognostic variables. Even the most accurate system of the PCR-MRD had problems with the detection of all relapse cases and out of the fifty patients that were classified by PCR-MRD as non-HR, six eventually relapsed, demonstrating that miR-151-5p and miR-451 adds unique information that is not found in MRD, and which is used, as described herein, to inform the proper course of treatment. Four out of those six had low miR-151-5p, miR-451 or both, which clearly indicates how these miRNAs can improve classification of ALL risk groups, and subsequent treatment decisions. At least as impressive are the results obtained for patients classified as non-high risk (which includes the SR and IR patients) according to PCR-MRD. In these patients, high miR-451 had a 92% relapse-free survival rate, whereas low miR-451 had a 50% relapse-free survival rate (FIG. 7A). Even more dramatically, combined high miR-451 and miR-151-5p had a 87% relapse-free survival rate, whereas combined low miR-451 and miR-151-5p had a 0% relapse-free survival rate in the IR group of patients (FIG. 7B).

It should be noted that the expression of the miRs of the invention was found to be an independent prognostic marker—with a relative risk of 9 to relapse as compared to the relative risk of 5.9 when using MRD results, as demonstrated by Table 3 and even in a more impressive manner in Table 4.

Finally, although the entire cohort included both T- and B-ALL patients, it seems as though miR-151-5p and miR-451 are more accurate in B-ALL. This can partly be explained by the fact that our cohort consisted of only 28 T-ALL samples that had generally low levels of those miRNAs. These results are also consistent with a previous publication that showed lower level of miR-151-5p in T-ALL [Fulci V et al., Genes, Chromosomes & Cancer. (2009); 48:1069-1082]. The results presented by the invention assist in promoting the idea of using miRNA and particularly, miR-151-5p and miR-451 as prognostic tools in ALL, and specifically, in pediatric ALL.

It should be appreciated that accurate and early prediction of prognosis, at the time of diagnosis may enable efficient and preventive treatment thereby decreasing relapse probability. Currently the risk group classification is obtained following day 78 from initial treatment by PCR-MRD analysis. Only then the treatment is tailored accordingly. The present invention enables stratification on the day of diagnosis (day 0).

Thus, in the first aspect, the present invention provides a method for the prognosis of ALL, monitoring and/or early diagnosis of ALL relapse in a mammalian subject, and directing an appropriate treatment regimen. The method of the invention comprises the steps of: first, in step (a) contacting detecting nucleic acid molecules specific for at least one of miR-151-5p and miR-451 and at least one suitable control reference gene or miRNA, with a test sample of the subject or with any nucleic acid product obtained therefrom, and optionally with a suitable control sample. The second step (b) involves the determination of the expression value of at least one of miR-151-5p, and miR-451 in the test sample, and optionally, in a suitable control sample. Similarly, step (c) involves the determination of the expression value of at least one suitable control reference gene or miRNA in the test sample, and optionally, in a suitable control sample, followed by (d) normalizing the expression value of the at least one of miR-151-5p, and miR-451 obtained in step (b) according to the expression value of the least one suitable control reference gene or miRNA obtained in step (c). Finally, in step (e), comparing the at least one normalized expression value obtained in step (d) with a corresponding predetermined cutoff value or with a normalized expression value of at least one of miR-151-5p, and miR-451 obtained from a suitable control sample according to step (b); wherein a positive expression value of at least one of the miR-151-5p, and miR-451 indicates that the subject belongs to a pre-established ALL patient population associated with a specific relapse rate. It should be understood that this relapse rate associated with said positive expression value is higher than the specific relapse rate associated with the pre-established ALL patient population where a corresponding at least one of the miR-151-5p and miR-451 has a negative expression value.

Thus, a positive expression value of either one of miR-151-5p and miR-451 or both reflects low expression of said miRNAs and is therefore indicative of a specific probability to relapse, said probability being higher than the specific probability of relapse in patients where the corresponding expression value of either one of miR-151-5p and miR-451 or both are negative. To disambiguate, a positive expression value indicates a higher risk for relapse than a negative expression value. More particularly, the relapse rate is at least 1%, at least %2, at least 3%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 70%, at least 80%, at least 90% or more higher than the relapse rate of the pre-established ALL patient population associated with the corresponding negative expression value (that reflects high levels of expression of these miRNAs). Non-limiting examples of such differences in relapse rate are provided in Examples 2-3 and 5-10. For instance, in Example 6 and FIG. 4A it is shown that ALL patients with WBC count under 20,000 and a high miR-151-5p expression value are associated with a 19% relapse rate, whereas ALL patients with WBC count under 20,000 and a low miR-151-5p expression value are associated with a 63% relapse rate. Thus, according to Example 6, ALL patients with WBC count under 20,000 and a low miR-151-5p expression value, which is under the cutoff value and therefore considered to be a positive expression value, have a relapse rate that is 44% higher than the relapse rate of ALL patients with WBC count under 20,000 and a high miR-151-5p expression value (which is considered to be a negative expression value vis a vis the cutoff value).

Generally, expression values lower than the cutoff values correlate with patient relapse better than expression values higher than the cutoff values. Thus, expression values of either miR-151-5p or miR-451 (or both) lower than their corresponding cutoff values are considered to be positive expression values and indicate a higher risk for relapse than negative expression values that reflect high level of expression. A group of patients having the same combination of clinical parameters as defined herein (including WBC>20,000 or WBC<20,000, gender, response to prednisone at day 8, etc.) and the same positive or negative miR-151-5p and miR-451 pattern belong to a pre-established population having the same specific probability to relapse.

The term "specific probability" refers to a probability of a patient to relapse based on the patients positive or negative miR-151-5p and miR-451 expression pattern, wherein the probability is calculated according to the patient population analysis provided herein, but may be further fine-tuned as more patient clinical data is accumulated and the same statistical analysis is reiterated using the augmented clinical population database, as demonstrated in Example 8 and illustrated in FIGS. 6 and 7.

This ascription of specific probabilities to relapse to defined populations means that the method of the invention may provide an early warning and indication for specific treatment regimens to patients in relapse risk, but it is also important to point out that the method may also indicate a positive outcome (i.e., relapse-free), and thereby prevent over-treatment. It should be further appreciated that the invention therefore provides a method for determining regimen of therapy by indicating whether the treated patient belongs to a relapse free group or will eventually relapse.

Furthermore, said positive expression value indicates that the subject belongs to a pre-established ALL patient population associated with a more accurate specific relapse rate than current clinical or biological methods could detect.

For clarity, when referring to a pre-established population of ALL patients, it is meant that a statistically-meaningful group of ALL patients was analyzed as disclosed herein, and the correlations between miR-151-5p and miR-451 expression values (and optionally other patient clinical parameters) and relapse rate was calculated. For example, a specific fraction of a group of patients, which was found to express miR-151-5p and miR-451 levels over the cutoff values according to the invention, was found to relapse in a certain rate. Thus, this rate of relapse is associated with a population expressing high levels of both miR-151-5p and miR-451, i.e., said population is a pre-established population, that is, a defined population whose relapse rate is known. Moreover, the populations may be defined by miR-151-5p and miR-451 expression rate vis a vis the cutoff values of the invention, but they may optionally be further divided into sub-populations according to other patient parameters, as elaborated herein, including for example gender, age, white blood cells count, response to prednisone treatment and mean residual disease as determined by PCR. For example, a population expressing miR-151-5p below the cutoff value according to the invention, miR-451 above the cutoff value according to the invention, and presenting a white blood count over 20,000 cells/ml is associated with a specific relapse rate, and is therefore an example of a pre-established population.

Nevertheless, the present invention shows that both miRs may serve as prognostic markers for ALL, specifically for predicting and monitoring ALL relapse. These markers were shown as independent markers that are not affected by clinical parameters or treatment regimen. The expression "associated with a specific relapse rate", "linked to a specific relapse rate", "associated with a relapse rate" or "associated with a pre-established ALL patient population" or similar expressions refer to a statistical connection between expression values of miR-151-5p and miR-451, and optionally, clinical parameters and a specific relapse rate, or the patient population which is known to relapse in that rate. Thus, for instance, as shown in Example 3 and FIG. 1, relapse free survival (RFS) rate in patients with high miR-151-5p was 79% and 52% for patients with low miR-151-5p. RFS of patients with high miR-451 was 75% and 53% for patients with low miR-451. RFS of patients with high expression of both miRNAs was 83% compared to 53% if at least one of them was low.

As indicated above, the present aspect of the invention relates to a prognostic method. Prognosis is defined as a forecast of the future course of a disease or disorder, based on medical knowledge. This highlights the major advantage of the instant invention over prior art, namely, the ability to predict relapse rate in patients as soon as they are diagnosed, even prior to treatment. This early prognosis facilitates the selection of appropriate treatment regimens that may minimize the predicted relapse, individually to each patient, as part of personalized medicine. As shown in the Examples provided, prior art lacks precision prognostic methods, and consequently some patients are under- or over-treated, resulting in relapse and excessive side effects of the treatment. Importantly, ALL patients defined as non-high or intermediate risk according to current knowledge are found to include subjects that are in fact in high risk by the instant prognostic method. Thus, the inventor's surprising finding that miR-151-5p and miR-451 expression correlates with relapse is both novel and extremely useful.

The foremost prognostic method currently in use is PCR-MRD, which is dependent on analysis on days 33 and 78 from the beginning of treatment. Until these time points only a crude prognosis is available based on clinical parameters (age, gender, WBC count, d8 prednisone response, cytogenetic abnormalities, etc.). Thus, depending on the analysis results, accurate prognosis is currently only available after 33 and in other cases 78 days after initiation of treatment. In contrast, the present invention provides a highly accurate prognosis as early as at the time of diagnosis, before initiation of treatment, and in fact, may assist in determining the optimal treatment. Accordingly, the prognostic method of the invention may provide a prognosis at the time of diagnosis, or up to at least 1 day, at least 2 days, at least 3 days, at least 4 days, at least 5 days, at least 6 days, at least 7 days, at least 8 days, at least 9 days, at least 10 days, at least 11 days, at least 12 days, at least 13 days, at least 14 days, at least 15 days, at least 16 days, at least 17 days, at least 18 days, at least 19 days, at least 20 days, at least 21 days, at least 22 days, at least 23 days, at least 24 days, at least 25 days, at least 26 days, at least 27 days, at least 28 days, at least 29 days, at least 30 days, at least 31 days, at least 32 days, at least 33 days, at least 40 days, at least 50 days, at least 60 days, at least 70 days, at least 78 days, at least 80, at least 90 days, at least 100 days, at least 110, at least 120 days, at least 130 days, at least 140 days or at least 150 days after diagnosis. At specific embodiments, the prognostic method of the invention may facilitate an accurate prognosis earlier than day 78 of treatment.

It should be appreciated that the sequences of miR-151-5p, and miR-451 are denoted by SEQ ID NO.:1 and 2, respectively.

The method of invention relies on the detection and determination of quantity of at least one of miR-151-5p, and miR-451, by contacting detecting nucleic acid molecules specific for at least one of miR-151-5p and miR-451 and at least one suitable control reference gene or miRNA. The term "contacting" means to bring, put, incubate or mix together. As such, a first item is contacted with a second item when the two items are brought or put together, e.g., by touching them to each other or combining them. In the context of the present invention, the term "contacting" includes all measures or steps which allow interaction between the at least one of the detection molecules for miR-151-5p, miR-451 and at least one suitable control reference gene or miRNA and the nucleic acid molecules of the tested sample. The contacting is performed in a manner so that the at least one of detecting molecule of miR-151-5p, miR-451 and at least one suitable control reference gene or miRNA can interact with or bind to the nucleic acid molecules in the tested sample. The binding will preferably be non-covalent, reversible binding, e.g., binding via salt bridges, hydrogen bonds, hydrophobic interactions or a combination thereof.

As described hereinabove, step (e) of the method for the prognosis of acute lymphoblastic leukemia provided by the invention refers to a predetermined cutoff value. It should be noted that a "cutoff value", sometimes referred to simply as "cutoff" herein, is a value that meets the requirements for both high diagnostic sensitivity (true positive rate) and high diagnostic specificity (true negative rate). miRNA expression level values that are higher or lower in comparison with said miRNAs corresponding cutoff value indicate that the examined sample belongs to a pre-established population associated with a specific relapse rate and limited to the said sensitivity and specificity.

It should be noted that the terms "sensitivity" and "specificity" are used herein with respect to the ability of one or more marker genes, specifically miR-451 and miR-151-5p, to correctly classify a sample as belonging to a pre-established population associated with a specific relapse rate.

"Sensitivity" indicates the performance of the marker genes with respect to correctly classifying samples as belonging to pre-established populations that are likely to relapse, wherein said marker genes expression values are lower than the cutoff, that is, positive values indicating higher relapse rates more likely to relapse than corresponding pre-established populations wherein said corresponding marker genes expression values are higher than the cutoff, that is, negative values indicating lower relapse rates.

"Specificity" indicates the performance of the marker genes with respect to correctly classifying samples as belonging to pre-established populations that are unlikely to relapse, wherein said marker genes expression values are higher than the cutoff, that is, negative values indicating lower relapse rates less likely to relapse than corresponding pre-established populations wherein said corresponding marker genes expression values are lower than the cutoff, that is, positive values indicating higher relapse rates.

Simply put, "sensitivity" relates to the rate of correct identification of high-relapse rate samples as such out of a group of samples, whereas "specificity" relates to the rate of correct identification of low-relapse rate samples as such out of a group of samples.

Cutoff values may be used as a control sample, said cutoff values being the result of a statistical analysis of miRNAs expression value differences in pre-established populations which either relapsed or remained disease-free. Specifically, it is understood that miR-151-5p and/or miR-451 expression values lower than the cutoff value found by the inventors, which are 0.00015 and 0.001, respectively (i.e., positive expression value), indicate a higher tendency to relapse in a patient than a patient where the corresponding miR-151-5p and/or miR-451 expression values are higher than the cutoff value (i.e., negative results). Thus, a given population having specific clinical parameters will have a defined likelihood to relapse based on the expression values of miR-151-5p and/or miR-451 being above or below said cutoff values. It should be emphasized that the nature of the invention is such that the accumulation of further patient data may improve the accuracy of the presently provided cutoff values, which are based on an ROC (Receiver Operating Characteristic) curve generated according to said patient data using, for example, a commercially available analytical software program. The miR-151-5p and/or miR-451 expression values are selected along the ROC curve for optimal combination of prognostic sensitivity and prognostic specificity which are as close to 100% as possible, and the resulting values are used as the cutoff values that distinguish between patients who will relapse at a certain rate, and those who will not (with said given sensitivity and specificity). The ROC curve may evolve as more and more patient-relapse data and related miR-151-5p and/or miR-451 expression values are recorded and taken into consideration, modifying the optimal cutoff values and improving sensitivity and specificity. Thus, the provided cutoff values should be viewed as a starting point that may shift as more patient-relapse data allows more accurate cutoff value calculation. Although considered as initial cutoff values, the presently provided values already provide good sensitivity and specificity, and are readily applicable in current clinical use, even in patients undergoing different treatment regimens, as described in Example 10.

Accordingly, specific relapse rates are provided by the inventors for different miR-151-5p and/or miR-451 expression levels, optionally, in combination with different clinical subgroups. It should be appreciated that the correlation of the negative or positive miR-151-5p and/or miR-451 expression values (as judged in relation to the cutoff value) indicate different specific relapse rates for patients presenting different clinical features. The inventors show that WBC count, age, MRD risk index, cytogenetic aberrations, response to prednisone treatment on day 8 and ploidy, all correlate with different relapse rates for different miR-151-5p and/or miR-451 expression values. Therefore, the inventors optionally provide specific relapse rates for various combinations of negative and positive miR-151-5p and/or miR-451 expression values (as judged in relation to the cutoff value) in combination with said different clinical features.

As indicated above, the method of the invention comprise the step of (d) normalizing the level of expression or the expression value of the at least one of miR-151-5p and miR-451, obtained in step (b) with the level of expression of control reference gene or miRNAs obtained in step (c) and thereby obtaining a normalized expression value of each of the at least one of miR-151-5p and miR-451 in the test sample. In certain embodiments, the control reference gene or miRNA could be 5S ribosomal RNA (rRNA), U6 small nuclear RNA, or any microRNA that maintained stable in all samples analyzed in the microarray analysis. The expression level of each miRNA relative to 5S may be determined by using dCt method, where dCt=(Ct miRNA-Ct 5S rRNA). The relative expression was calculated automatically by the LightCycler software. The Ct (cycle threshold) is defined as the number of amplification cycles required for the fluorescent signal to cross the threshold (i.e. exceeds background level). Ct levels are inversely proportional to the amount of target nucleic acid in the sample (i.e. the lower the Ct level the greater the amount of target nucleic acid in the sample). In yet another embodiment the relative expression level can be calculated according to the 2-[Delta][Delta]CT Method using a reference sample for normalization as described in Kenneth J. Livak and Thomas D. Schmittgen. Analysis of Relative Gene Expression Data Using Real-Time Quantitative PCR and the 2-[Delta][Delta]CT Method. Methods, 25(4):402-408, 2001.

In other embodiments, the miRXplore Universal Reference (UR) may be used as control reference, representing a pool of 979 synthetic miRNA for comparison of multiple samples.

Still further, in certain embodiments where a control sample is being used, the normalized expression values of at least one of the miRNAs used by the invention in the test sample are compared to the expression values in the tested sample.

In other embodiments a mix of synthetic miRNA 451 and miRNA 151 can be used as a reference samples.

The method of the invention involves the use of specific miRNAs as prognostic markers for predicting, monitoring and early diagnosis of ALL relapse. "MicroRNAs" ("miRNAs" or "miRs") as used herein are post-transcriptional regulators that bind to complementary sequences in the three prime untranslated regions (3' UTRs) of target messenger RNA transcripts (mRNAs), usually resulting in gene silencing. miRNAs are short ribonucleic acid (RNA) molecules, on average only 22 nucleotides long. The human genome may encode over 1000 miRNAs, which may target about 60% of mammalian genes and are abundant in many human cell types. Each miRNA may repress hundreds of mRNAs. miRNAs are well conserved in eukaryotic organisms and are thought to be a vital and evolutionarily ancient component of genetic regulation.

miRNA genes are usually transcribed by RNA polymerase II (Pol II). The polymerase often binds to a promoter found near the DNA sequence encoding what will become the hairpin loop of the pre-miRNA. The resulting transcript is capped with a specially-modified nucleotide at the 5' end, polyadenylated with multiple adenosines (a poly(A) tail), and spliced. The product, called a primary miRNA (pri-miRNA), may be hundreds or thousands of nucleotides in length and contain one or more miRNA stem loops. When a stem loop precursor is found in the 3' UTR, a transcript may serve as a pri-miRNA and a mRNA. RNA polymerase III (Pol III) transcribes some miRNAs, especially those with upstream Alu sequences, transfer RNAs (tRNAs), and mammalian wide interspersed repeat (MWIR) promoter units.

A single pri-miRNA may contain from one to six miRNA precursors. These hairpin loop structures are composed of about 70 nucleotides each. Each hairpin is flanked by sequences necessary for efficient processing. The double-stranded RNA structure of the hairpins in a pri-miRNA is recognized by a nuclear protein known as DiGeorge Syndrome Critical Region 8 (DGCR8 or "Pasha" in invertebrates), named for its association with DiGeorge Syndrome. DGCR8 associates with the enzyme Drosha, a protein that cuts RNA, to form the "Microprocessor" complex. In this complex, DGCR8 orients the catalytic RNase III domain of Drosha to liberate hairpins from pri-miRNAs by cleaving RNA about eleven nucleotides from the hairpin base (two helical RNA turns into the stem). The resulting hairpin, known as a pre-miRNA, has a two-nucleotide overhang at its 3' end; it has 3' hydroxyl and 5' phosphate groups.

pre-miRNAs that are spliced directly out of introns, bypassing the Microprocessor complex, are known as "mirtrons." Originally thought to exist only in *Drosophila* and *C. elegans*, mirtrons have now been found in mammals.

Perhaps as many as 16% of pri-miRNAs may be altered through nuclear RNA editing. Most commonly, enzymes known as adenosine deaminases acting on RNA (ADARs) catalyze adenosine to inosine (A to I) transitions. RNA editing can halt nuclear processing (for example, of pri-miR-142, leading to degradation by the ribonuclease Tudor-SN) and alter downstream processes including cytoplasmic miRNA processing and target specificity (e.g., by changing the seed region of miR-376 in the central nervous system). pre-miRNA hairpins are exported from the nucleus in a process involving the nucleocytoplasmic shuttle Exportin-5. In the cytoplasm, the pre-miRNA hairpin is cleaved by the RNase III enzyme Dicer. This endoribonuclease interacts with the 3' end of the hairpin and cuts away the loop joining the 3' and 5' arms, yielding an imperfect miRNA:miRNA* duplex about 22 nucleotides in length. Overall hairpin length and loop size influence the efficiency of Dicer processing, and the imperfect nature of the miRNA:miRNA* pairing also affects cleavage. Although either strand of the duplex may potentially act as a functional miRNA, only one strand is usually incorporated into the RNA-induced silencing complex (RISC) where the miRNA and its mRNA target interact.

The mature miRNA is part of an active RNA-induced silencing complex (RISC) containing Dicer and many associated proteins. RISC is also known as a microRNA ribonucleoprotein complex (miRNP); RISC with incorporated miRNA is sometimes referred to as "miRISC."

The prefix "mir" is followed by a dash and a number, the latter often indicating order of naming. For example, mir-123 was named and likely discovered prior to mir-456. The uncapitalized "mir-" refers to the pre-miRNA, while a capitalized "miR-" refers to the mature form. miRNAs with nearly identical sequences bar one or two nucleotides are annotated with an additional lower case letter. For example, miR-123a would be closely related to miR-123b. miRNAs that are 100% identical but are encoded at different places in the genome are indicated with additional dash-number suffix: miR-123-1 and miR-123-2 are identical but are produced from different pre-miRNAs. Species of origin is designated with a three-letter prefix, e.g., hsa-miR-123 would be from human (*Homo sapiens*). microRNAs originating from the 3' or 5' end of a pre-miRNA are denoted with a -3p or -5p suffix. When relative expression levels are known, an asterisk following the name indicates an miRNA expressed at low levels relative to the miRNA in the opposite arm of a hairpin. For example, miR-123 and miR-123* would share a pre-miRNA hairpin, but relatively more miR-123 would be found in the cell.

In particular non-limiting embodiments, the ALL patient population group that may be examined and monitored by the prognostic and treatment methods and systems of the present invention may optionally further be defined by sub-grouping of the patient according to at least one clinical criterion, and each the patient sub-group belongs to a specific pre-established ALL patient population associated with a specific relapse rate and specific treatment regimen. According to such optional certain embodiments, the clinical criteria comprise:
a. sub-grouping according to B-ALL and T-ALL diagnosis;
b. sub-grouping according to minimal residual disease (MRD) high, intermediate and low risk definitions;
c. sub-grouping according to response to prednisone on day 8 of treatment;
d. sub-grouping according to BFM high, intermediate and low risk definitions;
e. sub-grouping according to white blood count (WBC) being over or below 20,000 cells/ml;
f. sub-grouping according to patient age being over one and under six years old or otherwise;
g. sub-grouping according to CCG high, intermediate and low risk definitions;
h. sub-grouping according to gender.

According to one embodiment, a good response to prednisone (prednisone dosage is 60 mg/M$^2$/per day) on day 8 of treatment is defined as a finding of less than 1000 leukemic blast cells, whereas a poor response to prednisone on day 8 of treatment is defined as a finding of more than 1000 leukemic blast cells per microliter of blood.

In specific embodiments, the patient sub-group clinical criterion of the prognostic method of the invention is B-ALL diagnosis.

Figure 2A:
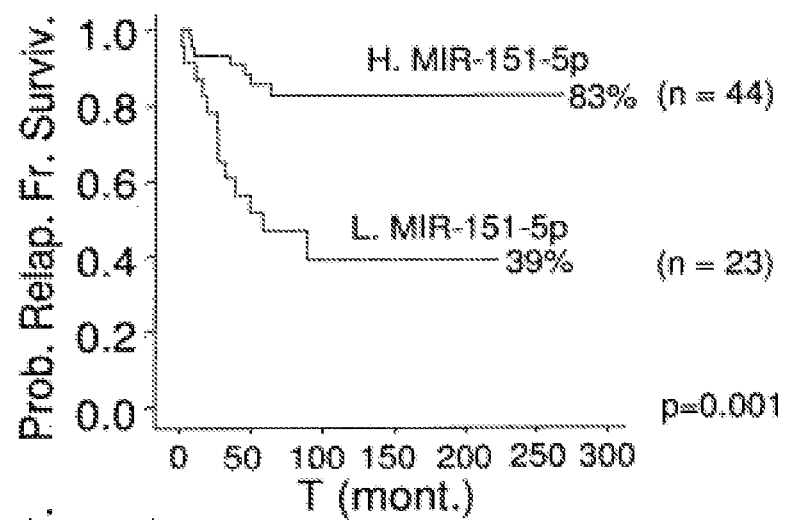
FIG. 2A-2C: Kaplan Meier estimation of Relapse Free Survival (RFS) in a cohort of 67 B-ALL patients. Probability of relapse-free survival in months from diagnosis commencement is shown.
Figure 2B:
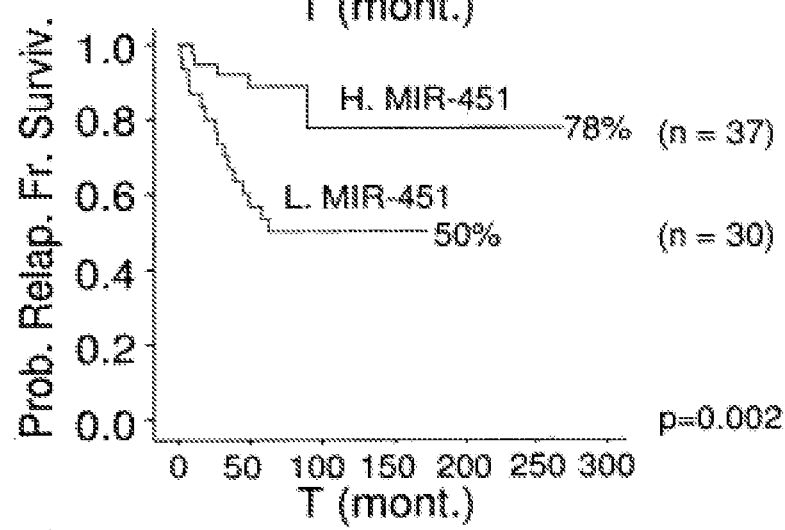
Figure 2C:
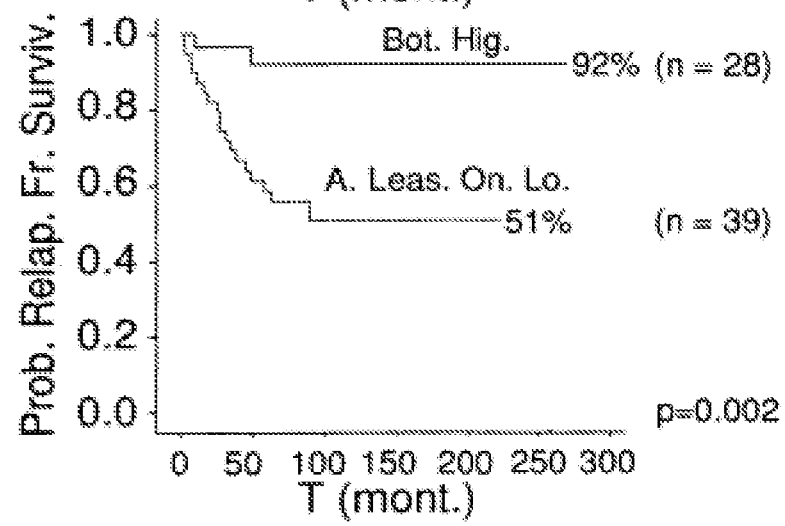

In particular embodiments, the method of the invention is specifically applicable for predicting B-ALL relapse. Since the expression level of both miRNAs was generally low in the T-cell group, the inventors focused only on the B-ALL group. In this group, miR-451 or miR-151-5p or both combined can significantly divide this group into two subgroups with distinct relapse rates: high expression correlated with good prognosis of 78%-92% versus 39%-51% RFS in the low expression group (FIG. 2A-C). The same results were achieved in an extended B-ALL cohort (n=91)(FIG. 6A-D).

Thus, in yet more specific embodiments, the method of the invention is specifically applicable for predicting B-ALL relapse and providing the appropriate treatment regimen known to the art to inhibit the relapse. However, it should be appreciated that the prognostic methods of the invention may be also suitable for prognosis and monitoring of T-ALL relapse.

In particular and specific embodiment, the prognosis methods and kits of the invention are particularly suitable for predicting and monitoring ALL relapse in pediatric patients.

In yet another embodiment, the methods of the invention may be used for predicting and monitoring relapse in adult ALL patients.

According to other embodiments, the patient risk according to at least one of minimal residual disease (MRD) risk definitions, response to prednisone on day 8 of treatment, BFM high, intermediate and low risk definitions, white blood count (WBC) being over or below 20,000 cells/ml, patient age being over one and under six years old or otherwise, CCG high and low risk definitions and gender, as explained below.

The classification of patients to HR and non-HR was performed twice: first according to clinical parameters for high and non-high risk (herein referred to as BFM-R) which takes into account for HR: cytogenetic abnormalities as MLL rearrangements and Philadelphia chromosome, poor prednisone response, age under one year and hypodiploidy. SR defined as with no cytogenetic abnormality and good prednisone response. IR: all patients outside the scope of HR and SR definitions. The second classification was based on PCR-MRD. The PCR-MRD standard group was defined as patients who were MRD negative at both time points (days 33 and 78), the PCR-MRD high risk group as positive MRD levels ($>10^{-3}$) at the second time point, and PCR-MRD intermediate group consisted of all the rest. PCR-MRD non-HR contained SR and IR patients.

In certain embodiments, the method of the invention is specifically applicable for predicting relapse within the PCR-MRD non-HR and in the IR (intermediate-risk) ALL patients who need to be treated by the intense HR treatment regimen. When analyzing only the B-ALL non-HR patients or only the IR group, the expression levels of both miRs could divide this risk group into two distinct subgroups with different outcome. As demonstrated in FIGS. 7A and 7B, patients expressing low levels of both miRNAs had a poor RFS (50% and 0%, respectively) in comparison with 92% and 87% in patients where both were highly expressed. Thus, even within the intermediate risk group population, the expression level of both miRs—can still discriminate within the non-HR and the IR risk group between two subgroups with different relapse rates, and thus be used for determining the corresponding treatment regimen. miR-451 was also found to be of significantly associated with relapse free survival in the IR: out of 13 patients expressing high levels of miR-451, 1 relapsed. Out of the 6 expressing low levels, 3 relapsed (p=0.041).

It should be appreciated that MRD may be monitored by any technique acceptable in the art, for example, PCR or FACS.

According to one embodiment, the prognostic method of the invention may be performed using a test sample of the subject, obtained during diagnosis of ALL.

It is understood that according to this embodiment, the method of the invention offers an accurate prognosis for the subject, and facilitates an intelligent, evidence-based choice of optimal treatment regimen before commencing any initial standardized treatment.

As indicated above, the present invention further provides early diagnosis of ALL relapse. The diagnostic method of the invention is based upon the finding demonstrated in Example 11 and illustrated in FIGS. 10A and 10B, that patients undergoing a relapse express decreasing amounts of at least one of miR-151-5p, and miR-451. It is therefore appreciated that the reduction in the expression of these markers constitutes an early marker of relapse. In fact, this early marker provides "early diagnosis" and is a molecular, sub-symptomatic precursor to the clinical symptoms associated with a relapse. By monitoring the patient for these markers expression patterns, medical staff may become away of a relapse earlier than they currently are, and consequently, provide earlier and more effective treatment.

Thus, according to one embodiment, the method of the invention further provides early diagnosis and monitoring of ALL relapse. Such method may further comprise the steps of: (f) repeating steps (a) to (d) to obtain normalized expression values of the at least one of miR-151-5p, and miR-451, for at least one more temporally-separated test sample; and (e) calculating the rate of change of the normalized expression values of the at least one of miR-151-5p, and miR-451 between the temporally-separated test samples. A negative rate of change of the normalized expression values of at least one of the miR-151-5p, and miR-451 indicates that the subject is in relapse.

In practice, to detect a decline in miR-151-5p, and miR-451 expression, at least two "temporally-separated" test samples must be collected from the patient, and preferably more. The expression of at least one of the markers is then determined using the method of the invention, applied for each sample. The rate of change in marker expression is then calculated by determining the difference in normalized expression values of said markers between any two samples and dividing the difference by the period of time that had over-lapsed between the collections of said two samples that are "temporally-separated" i.e., obtained from the same patient in different time-points or time intervals. This period of time, also referred to as "time interval", or the difference between time points (wherein each time point is the time when a specific sample was collected) may be any period deemed appropriate by medical staff and modified as needed according to the specific requirements of the patient and the clinical state he or she may be in. For example, this interval may be at least one day, at least three days, at least three days, at least one week, at least two weeks, at least three weeks, at least one month, at least two months, at least three months, at least four months, at least five months, at least one year, or even more.

When calculating the rate of change, one may use any two samples collected at different time points from the patient. To ensure more reliable results and reduce statistical deviations to a minimum, averaging the calculated rates of several sample pairs is preferable. A calculated or average negative rate of change of the normalized expression values of at least one of the miR-151-5p and miR-451 indicates that the subject is in relapse.

For example, if three samples were collected on (i) January 1, (ii) March 1 and (iii) April 20, and the normalized expression level of miR-451 was 10, 6 and 4 [arbitrary units], respectively, then the rate of change may be calculated as any one of:

(A) calculated from (i) to (ii): (6-10)/59 [days]=−0.0678 [arbitrary unit/day]
(B) calculated from (ii) to (iii): (4-6)/109 [days]=−0.01835 [arbitrary unit/day]
(C) Average of (A) and (B)=−0.04307 [arbitrary unit/day]

Although the three results are slightly different, they are all negative, thus indicating a relapse.

As indicated above, in order to execute the diagnostic method of the invention, at least two different samples must be obtained from the subject in order to calculate the rate of expression change in at least one of miR-151-5p, and miR-451. By obtaining at least two and preferably more biological samples from a subject and analyzing them according to the method of the invention, the diagnostic method may be effective for predicting, monitoring and early diagnosing molecular alterations indicating a relapse in said patient. Thus, the prognostic method may be applicable for early, sub-symptomatic diagnosis of relapse when used for analysis of more than a single sample along the time-course of diagnosis, treatment and follow-up. An "early diagnosis" provides diagnosis prior to appearance of clinical symptoms. Prior as used herein is meant days, weeks, months or even years before the appearance of such symptoms. More specifically, at least 1 week, at least 1 month, 2 months, 3 months, 4 months, 5 months, 6 months, 7 months, 8 months, 9 months, 10 months, 11 months, 12 months, or even few years before clinical symptoms appear.

Simply put, a decline in the expression of at least one of miR-151-5p, and miR-451 indicates a relapse, and may provide an early sign before over symptoms occur, allowing for a quicker and more efficient therapeutic response.

Of course, more samples taken in more time-points may provide a statistically robust analysis of said expression trends, and may also be utilized as a method for continuous monitoring of subjects, especially those still undergoing and those that have undergone therapy. The more samples are available over a given time period, the higher is the resolution of the expression patterns of miR-151-5p, and miR-451 during said period.

The number of samples collected and used for evaluation of the subject may change according to the frequency with which they are collected. For example, the samples may be collected at least every day, every two days, every four days, every week, every two weeks, every three weeks, every month, every two months, every three months every four months, every 5 months, every 6 months, every 7 months, every 8 months, every 9 months, every 10 months, every 11 months, every year or even more. Furthermore, to assess the trend in expression rates according to the invention, it is understood that the rate of change may be calculated as an average rate of change over at least three samples taken in different time points, or the rate may be calculated for every two samples collected at adjacent time points. It should be appreciated that the sample may be obtained from the monitored patient in the indicated time intervals for a period of several months or several years. More specifically, for a period of 1 year, for a period of 2 years, for a period of 3 years, for a period of 4 years, for a period of 5 years, for a period of 6 years, for a period of 7 years, for a period of 8 years, for a period of 9 years, for a period of 10 years, for a period of 11 years, for a period of 12 years, for a period of 13 years, for a period of 14 years, for a period of 15 years or more. In one particular example, the samples are taken from the monitored subject every two months for a period of 5 years.

In any case, a reduction in the normalized expression values of at least one of miR-151-5p, and miR-451 indicates a relapse, whereas an increase in their values may indicate an improvement in the clinical condition of the subject, i.e., that the patient is in remission (FIGS. 10C and 10D).

As indicated above, according to certain embodiments, the method of the invention uses detecting nucleic acid molecules to determine the expression levels of the miRNAs of the invention in a tested sample. In certain embodiments, such detecting molecules may comprise isolated oligonucleotides that specifically hybridize to a nucleic acid sequence of at least one of miR-151-5p and miR-451 and of at least one of the control reference gene or miRNA.

As used herein, "nucleic acid(s)" is interchangeable with the term "polynucleotide(s)" and generally refers to any polyribonucleotide or poly-deoxyribonucleotide, which may be unmodified RNA or DNA or modified RNA or DNA or any combination thereof. "Nucleic acids" include, without limitation, single- and double-stranded nucleic acids. As used herein, the term "nucleic acid(s)" also includes DNAs or RNAs as described above that contain one or more modified bases. Thus, DNAs or RNAs with backbones modified for stability or for other reasons are "nucleic acids". The term "nucleic acids" as it is used herein embraces such chemically, enzymatically or metabolically modified forms of nucleic acids, as well as the chemical forms of DNA and RNA characteristic of viruses and cells, including for example, simple and complex cells. A "nucleic acid" or "nucleic acid sequence" may also include regions of single- or double-stranded RNA or DNA or any combinations.

As used herein, the term "oligonucleotide" is defined as a molecule comprised of two or more deoxyribonucleotides and/or ribonucleotides, and preferably more than three. Its exact size will depend upon many factors which in turn, depend upon the ultimate function and use of the oligonucleotide. The oligonucleotides may be from about 8 to about 1,000 nucleotides long. Although oligonucleotides of 5 to 100 nucleotides are useful in the invention, preferred oligonucleotides range from about 5 to about 15 bases in length, from about 5 to about 20 bases in length, from about 5 to about 25 bases in length, from about 5 to about 30 bases in length, from about 5 to about 40 bases in length or from about 5 to about 50 bases in length. More specifically, the detecting oligonucleotides molecule used by the methods, as well as by the compositions and kits of the invention may comprise any one of 5, 6, 7, 8, 9, 10, 11, 12, 13, 14, 15, 16, 17, 18, 19, 20, 21, 22, 23, 24, 25, 26, 27, 28, 29, 30, 35, 40, 45, 50 bases in length.

The term "about" as used herein indicates values that may deviate up to 1%, more specifically 5%, more specifically 10%, more specifically 15%, and in some cases up to 20% higher or lower than the value referred to, the deviation range including integer values, and, if applicable, non-integer values as well, constituting a continuous range.

As indicated above, the compositions, kits and methods of the invention comprise oligonucleotides that specifically hybridize to nucleic acid sequences of miR-151-5p and miR-451. As used herein, the term "hybridize" refers to a process where two complementary nucleic acid strands anneal to each other under appropriately stringent conditions. Hybridizations are typically and preferably conducted with probe-length nucleic acid molecules, for example, 5-100 nucleotides in length, 5-50, 5-40, 5-30 or 5-20.

As used herein "selective or specific hybridization" in the context of this invention refers to a hybridization which occurs between a polynucleotide encompassed by the invention as detecting molecules, and any one of miR-151-5p and miR-451 or any control reference gene or miRNA, wherein the hybridization is such that the polynucleotide binds to miR-151-5p and miR-451 or any control reference gene or miRNA preferentially to any other RNA in the tested sample. In a preferred embodiment a polynucleotide which "selectively hybridizes" is one which hybridizes with a selectivity of greater than 60%, greater than 70%, greater than 80%, greater than 90% and most preferably on 100% (i.e. cross hybridization with other RNA species preferably occurs at less than 40%, less than 30%, less than 20%, less than 10%). As would be understood to a person skilled in the art, a detecting polynucleotide which "selectively hybridizes" to miR-151-5p, miR-451 or any control reference gene or miRNA can be designed taking into account the length and composition.

The terms, "specifically hybridizes", "specific hybridization" refers to hybridization which occurs when two nucleic acid sequences are substantially complementary (at least about 60% complementary over a stretch of at least 5 to 25 nucleotides, preferably at least about 70%, 75%, 80% or 85% complementary, more preferably at least about 90% complementary, and most preferably, about 95% complementary).

The measuring of the expression of any one of miR-151-5p, miR-451 and any control reference gene or miRNA and combination thereof can be done by using those polynucleotides as detecting molecules, which are specific and/or selective for miR-151-5p, miR-451 or any control reference gene or miRNA to quantitate the expression of said miR-151-5p, miR-451 or any control reference gene or miRNA. In a specific embodiment of the invention, the polynucleotides which are specific and/or selective for said miR-151-5p, miR-451 or any control reference gene or miRNA may be probes or primers. It should be further appreciated that the methods, as well as the compositions and kits of the invention may comprise, as an oligonucleotide-based detection molecule, both primers and probes.

The term, "primer", as used herein refers to an oligonucleotide, whether occurring naturally as in a purified restriction digest, or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be single-stranded or double-stranded and must be sufficiently long to prime the synthesis of the desired extension product in the presence of the inducing agent. The exact length of the primer will depend upon many factors, including temperature, source of primer and the method used. For example, for diagnostic applications, depending on the complexity of the target sequence, the oligonucleotide primer typically contains 10-30 or more nucleotides, although it may contain fewer nucleotides. More specifically, the primer used by the methods, as well as the compositions and kits of the invention may comprise 10, 11, 12, 13, 14, 15, 16, 17, 18, 19, 20, 21, 22, 23, 24, 25, 26, 27, 28, 29 or 30 nucleotides or more. In certain embodiments, such primers may comprise 30, 40, 50, 60, 70, 80, 90, 100 nucleotides or more. In specific embodiments, the primers used by the method of the invention may have a stem and loop structure. The factors involved in determining the appropriate length of primer are known to one of ordinary skill in the art and information regarding them is readily available.

As used herein, the term "probe" means oligonucleotides and analogs thereof and refers to a range of chemical species that recognize polynucleotide target sequences through hydrogen bonding interactions with the nucleotide bases of the target sequences. The probe or the target sequences may be single- or double-stranded RNA or single- or double-stranded DNA or a combination of DNA and RNA bases. A probe is at least 5 or preferably, 8 nucleotides in length and less than the length of a complete miRNA. A probe may be 5, 6, 7, 8, 9, 10, 11, 12, 13, 14, 15, 16, 17, 18, 19, 20, 21, 22, 23, 24, 25, 26, 27, 28, 29 and up to 30 nucleotides in length as long as it is less than the full length of the target miRNA or any gene encoding said miRNA. Probes can include oligonucleotides modified so as to have a tag which is detectable by fluorescence, chemiluminescence and the like. The probe can also be modified so as to have both a detectable tag and a quencher molecule, for example TaqMan® and Molecular Beacon® probes, that will be described in detail below.

The oligonucleotides and analogs thereof may be RNA or DNA, or analogs of RNA or DNA, commonly referred to as antisense oligomers or antisense oligonucleotides. Such RNA or DNA analogs comprise, but are not limited to, 2'-O-alkyl sugar modifications, methylphosphonate, phosphorothioate, phosphorodithioate, formacetal, 3-thioformacetal, sulfone, sulfamate, and nitroxide backbone modifications, and analogs, for example, LNA analogs, wherein the base moieties have been modified. In addition, analogs of oligomers may be polymers in which the sugar moiety has been modified or replaced by another suitable moiety, resulting in polymers which include, but are not limited to, morpholino analogs and peptide nucleic acid (PNA) analogs. Probes may also be mixtures of any of the oligonucleotide analog types together or in combination with native DNA or RNA. At the same time, the oligonucleotides and analogs thereof may be used alone or in combination with one or more additional oligonucleotides or analogs thereof.

Thus, according to one embodiment, such oligonucleotides are any one of a pair of primers or nucleotide probes, and wherein the level of expression of at least one of the miR-151-5p and miR-451 is determined using a nucleic acid amplification assay selected from the group consisting of: a Real-Time PCR, micro array, PCR, in situ hybridization and comparative genomic hybridization.

The term "amplify", with respect to nucleic acid sequences, refers to methods that increase the representation of a population of nucleic acid sequences in a sample. Nucleic acid amplification methods, such as PCR, isothermal methods, rolling circle methods, etc., are well known to the skilled artisan. More specifically, as used herein, the term "amplified", when applied to a nucleic acid sequence, refers to a process whereby one or more copies of a particular nucleic acid sequence is generated from a template nucleic acid, preferably by the method of polymerase chain reaction.

"Polymerase chain reaction" or "PCR" refers to an in vitro method for amplifying a specific nucleic acid template sequence. The PCR reaction involves a repetitive series of temperature cycles and is typically performed in a volume of 50-100 µl. The reaction mix comprises dNTPs (each of the four deoxynucleotides dATP, dCTP, dGTP, and dTTP), primers, buffers, DNA polymerase, and nucleic acid template. The PCR reaction comprises providing a set of polynucleotide primers wherein a first primer contains a sequence complementary to a region in one strand of the nucleic acid template sequence and primes the synthesis of a complementary DNA strand, and a second primer contains a sequence complementary to a region in a second strand of the target nucleic acid sequence and primes the synthesis of a complementary DNA strand, and amplifying the nucleic acid template sequence employing a nucleic acid polymerase as a template-dependent polymerizing agent under conditions which are permissive for PCR cycling steps of (i) annealing of primers required for amplification to a target nucleic acid sequence contained within the template sequence, (ii) extending the primers wherein the nucleic acid polymerase synthesizes a primer extension product. "A set of polynucleotide primers", "a set of PCR primers" or "pair of primers" can comprise two, three, four or more primers.

Real time nucleic acid amplification and detection methods are efficient for sequence identification and quantification of a target since no pre-hybridization amplification is required. Amplification and hybridization are combined in a single step and can be performed in a fully automated, large-scale, closed-tube format.

Methods that use hybridization-triggered fluorescent probes for real time PCR are based either on a quench-release fluorescence of a probe digested by DNA Polymerase (e.g., methods using TaqMan®, MGB-TaqMan®), or on a hybridization-triggered fluorescence of intact probes (e.g., molecular beacons, and linear probes). In general, the probes are designed to hybridize to an internal region of a PCR product during annealing stage (also referred to as amplicon). For those methods utilizing TaqMan® and MGB-TaqMan® the 5'-exonuclease activity of the approaching DNA Polymerase cleaves a probe between a fluorophore and a quencher, releasing fluorescence.

Thus, a "real time PCR" assay provides dynamic fluorescence detection of amplified miR-151-5p and miR-451 or any control reference gene or miRNA produced in a PCR amplification reaction. During PCR, the amplified products created using suitable primers hybridize to probe nucleic acids (TaqMan® probe, for example), which may be labeled according to some embodiments with both a reporter dye and a quencher dye. When these two dyes are in close proximity, i.e. both are present in an intact probe oligonucleotide, the fluorescence of the reporter dye is suppressed. However, a polymerase, such as AmpliTaq Gold™, having 5'-3' nuclease activity can be provided in the PCR reaction. This enzyme cleaves the fluorogenic probe if it is bound specifically to the target nucleic acid sequences between the priming sites. The reporter dye and quencher dye are separated upon cleavage, permitting fluorescent detection of the reporter dye. Upon excitation by a laser provided, e.g., by a sequencing apparatus, the fluorescent signal produced by the reporter dye is detected and/or quantified. The increase in fluorescence is a direct consequence of amplification of target nucleic acids during PCR.

The method and hybridization assays using self-quenching fluorescence probes with and/or without internal controls for detection of nucleic acid application products are known in the art, for example, U.S. Pat. Nos. 6,258,569; 6,030,787; 5,952,202; 5,876,930; 5,866,336; 5,736,333; 5,723,591; 5,691,146; and 5,538,848.

More particularly, QRT-PCR or "qPCR" (Quantitative RT-PCR), which is quantitative in nature, can also be performed to provide a quantitative measure of gene expression levels. In QRT-PCR reverse transcription and PCR can be performed in two steps, or reverse transcription combined with PCR can be performed. One of these techniques, for which there are commercially available kits such as TaqMan® (Perkin Elmer, Foster City, Calif.), is performed with a transcript-specific antisense probe. This probe is specific for the PCR product (e.g. a nucleic acid fragment derived from a gene, or in this case, from a pre-miRNA) and is prepared with a quencher and fluorescent reporter probe attached to the 5' end of the oligonucleotide. Different fluorescent markers are attached to different reporters, allowing for measurement of at least two products in one reaction.

When Taq DNA polymerase is activated, it cleaves off the fluorescent reporters of the probe bound to the template by virtue of its 5-to-3' exonuclease activity. In the absence of the quenchers, the reporters now fluoresce. The color change in the reporters is proportional to the amount of each specific product and is measured by a fluorometer; therefore, the amount of each color is measured and the PCR product is quantified. The PCR reactions can be performed in any solid support, for example, slides, microplates, 96 well plates, 384 well plates and the like so that samples derived from many individuals are processed and measured simultaneously. The TaqMan® system has the additional advantage of not requiring gel electrophoresis and allows for quantification when used with a standard curve.

A second technique useful for detecting PCR products quantitatively without is to use an intercalating dye such as the commercially available QuantiTect SYBR Green PCR (Qiagen, Valencia Calif.). RT-PCR is performed using SYBR green as a fluorescent label which is incorporated into the PCR product during the PCR stage and produces fluorescence proportional to the amount of PCR product.

Both TaqMan® and QuantiTect SYBR systems can be used subsequent to reverse transcription of RNA. Reverse transcription can either be performed in the same reaction mixture as the PCR step (one-step protocol) or reverse transcription can be performed first prior to amplification utilizing PCR (two-step protocol).

Additionally, other known systems to quantitatively measure mRNA expression products include Molecular Beacons® which uses a probe having a fluorescent molecule and a quencher molecule, the probe capable of forming a hairpin structure such that when in the hairpin form, the fluorescence molecule is quenched, and when hybridized, the fluorescence increases giving a quantitative measurement of gene expression, or in this case, miRNA expression.

In one embodiment, the polynucleotide-based detection molecules of the invention may be in the form of nucleic acid probes which can be spotted onto an array to measure RNA from the sample of a subject to be diagnosed.

As defined herein, a "nucleic acid array" refers to a plurality of nucleic acids (or "nucleic acid members"), optionally attached to a support where each of the nucleic acid members is attached to a support in a unique pre-selected and defined region. These nucleic acid sequences are used herein as detecting nucleic acid molecules. In one embodiment, the nucleic acid member attached to the surface of the support is DNA. In a preferred embodiment, the nucleic acid member attached to the surface of the support is either cDNA or oligonucleotides. In another embodiment, the nucleic acid member attached to the surface of the support is cDNA synthesized by polymerase chain reaction (PCR). In another embodiment, a "nucleic acid array" refers to a plurality of unique nucleic acid detecting molecules attached to nitrocellulose or other membranes used in Southern and/or Northern blotting techniques.

For oligonucleotide-based arrays, the selection of oligonucleotides corresponding to the gene of interest which are useful as probes is well understood in the art.

More particularly, it is important to choose regions which will permit hybridization to the target nucleic acids. Factors such as the Tm of the oligonucleotide, the percent GC content, the degree of secondary structure and the length of nucleic acid are important factors.

According to this embodiment, the detecting molecule may be in the form of probe corresponding and thereby hybridizing to any region or part of miR-151-5p and miR-451 or any control reference gene or miRNA.

As indicated above, assay based on micro array or RT-PCR may involve attaching or spotting of the probes in a solid support. As used herein, the terms "attaching" and "spotting" refer to a process of depositing a nucleic acid onto a substrate to form a nucleic acid array such that the nucleic acid is stably bound to the substrate via covalent bonds, hydrogen bonds or ionic interactions.

As used herein, "stably associated" or "stably bound" refers to a nucleic acid that is stably bound to a solid substrate to form an array via covalent bonds, hydrogen bonds or ionic interactions such that the nucleic acid retains its unique pre-selected position relative to all other nucleic acids that are stably associated with an array, or to all other pre-selected regions on the solid substrate under conditions in which an array is typically analyzed (i.e., during one or more steps of hybridization, washes, and/or scanning, etc.).

As used herein, "substrate" or "support" or "solid support", when referring to an array, refers to a material having a rigid or semi-rigid surface. The support may be biological, non-biological, organic, inorganic, or a combination of any of these, existing as particles, strands, precipitates, gels, sheets, tubing, spheres, beads, containers, capillaries, pads, slices, films, plates, slides, chips, etc. Often, the substrate is a silicon or glass surface, (poly)tetrafluoroethylene, (poly)vinylidendifluoride, polystyrene, polycarbonate, a charged membrane, such as nylon or nitrocellulose, or combinations thereof. Preferably, at least one surface of the substrate will be substantially flat. The support may optionally contain reactive groups, including, but not limited to, carboxyl, amino, hydroxyl, thiol, and the like. In one embodiment, the support may be optically transparent.

It should be further noted that a standard Northern blot assay can also be used to ascertain an RNA transcript size and the relative amounts of miR-151-5p and miR-451 or any control gene product, in accordance with conventional Northern hybridization techniques known to those persons of ordinary skill in the art.

Particular embodiments of the method of the invention are based on detecting the expression values of miR-151-5p. According to this embodiment, the detecting nucleic acid molecules used by the method of the invention comprise isolated oligonucleotides that specifically hybridize to a nucleic acid sequence of miR-151-5p, and isolated oligonucleotides that specifically hybridize to a nucleic acid sequence of at least one of the control reference gene or miRNA.

Other specific embodiments of the method of the invention are based on detecting expression values of miR-451.

According to such embodiment, the detecting nucleic acid molecules used by the method of the invention comprise isolated oligonucleotides that specifically hybridize to a nucleic acid sequence of miR-451 and isolated oligonucleotides that specifically hybridize to a nucleic acid sequence of at least one of the control reference gene or miRNA.

Yet other embodiments of the method of the invention are based on detecting the expression values of miR-151-5p and of miR-451. According to this embodiment, the detecting nucleic acid molecules used by the method of the invention comprise isolated oligonucleotides that specifically hybridize to a nucleic acid sequence of miR-151-5p, isolated oligonucleotides that specifically hybridize to a nucleic acid sequence of miR-451 and isolated oligonucleotides that specifically hybridize to a nucleic acid sequence of at least one of the control reference gene or miRNA.

It should be appreciated that all the detecting molecules used by any of the methods, as well as the compositions and kits of the invention are isolated and/or purified molecules. As used herein, "isolated" or "purified" when used in reference to a nucleic acid means that a naturally occurring sequence has been removed from its normal cellular (e.g., chromosomal) environment or is synthesized in a non-natural environment (e.g., artificially synthesized). Thus, an "isolated" or "purified" sequence may be in a cell-free solution or placed in a different cellular environment. The term "purified" does not imply that the sequence is the only nucleotide present, but that it is essentially free (about 90-95% pure) of non-nucleotide material naturally associated with it, and thus is distinguished from isolated chromosomes.

As used herein the terms "miR-151-5p", "miR-451" or any "control reference gene or miRNA" refer to the miRNA expressed by genes encoding miR-151-5p, miR-451 or any control reference gene or miRNA, and refers to the sequence of miR-151-5p, miR-451 or any control reference gene miRNA, including pri- and pre-miR-151-5p and miR-451 or any appropriate control reference gene or miRNA. It should be noted that the miRs sequences used by the present invention were obtained from miRBase. More specifically, the mature sequence: MIMAT0004697 of hsa-miR-151-5p comprises the nucleic acid sequence of: ucgaggagcucacagucuagu. In certain embodiments, said miR-151-5p is also denoted by SEQ ID NO. 1. It yet other embodiments, the mature sequence: MIMAT0001631 of hsa-miR-451 comprises the nucleic acid sequence of aaaccguuaccauuacugaguu. More specifically, said miR-451 is also denoted by SEQ ID NO. 2.

The method of the invention relates to prognosis of ALL based on examining the expression of certain miRNAs, specifically, miR-151-5p and/or miR-451 in a test sample, specifically, a biological sample obtained from a subject. It is appreciated that the biological sample of the invention is any one of bone marrow, lymph fluid, blood cells, blood, serum, plasma, urine, sputum, saliva, faeces, semen, spinal fluid or CSF, the external secretions of the skin, respiratory, intestinal, and genitourinary tracts, tears, milk, any human organ or tissue, any sample obtained by lavage optionally of the breast ductal system, plural effusion, samples of in vitro or ex vivo cell culture and cell culture constituents or in vivo samples.

In certain embodiments, the sample that may be evaluated by the method of the invention may be a sample of bone marrow.

Bone marrow can be obtained through biopsy or aspiration from the sternum or the calvarium in adults, and in long bones, such as the femur and tibia, in adolescents. Biopsy needles for extraction of solid bone marrow are known.

It should be appreciated that the method of the invention is particularly applicable for the determination and carrying out an appropriate treatment regimen for ALL, including both, B-ALL and T-ALL. More specifically, the method of the invention may be suitable for the prognosis of T-ALL relapse. In certain embodiments, the method of the invention is particularly powerful in predicting relapse of ALL, specifically, B-ALL.

In a second aspect, the present invention relates to a diagnostic or prognostic composition for the prognosis of ALL. The composition of the invention comprises detecting nucleic acid molecules specific for determination of the expression of at least one of miR-151-5p and miR-451, also denoted by SEQ ID NO.:1 and 2, respectively, and of at least one control reference gene or miRNA. In certain embodiments, the composition of the invention is for determining the expression value of at least one of miR-151-5p and miR-451 in a biological test sample of a mammalian subject.

According to some embodiments, the ALL of the prognostic composition of the invention may be any one of B-ALL or T-ALL. It yet another specific embodiment, the prognostic methods of the invention are also suitable for prediction, monitoring and early diagnosis of B-ALL relapse.

According to some embodiments, the detecting nucleic acid molecules comprised within the diagnostic or prognostic composition of the invention may comprise isolated oligonucleotides that specifically hybridize to a nucleic acid sequence of miR-151-5p and isolated oligonucleotides that specifically hybridize to a nucleic acid sequence of at least one of the control reference gene or miRNA.

In specific embodiments, the detecting nucleic acid molecules comprised within the prognostic composition of the invention may comprise isolated oligonucleotides that specifically hybridize to a nucleic acid sequence of miR-451 and isolated oligonucleotides that specifically hybridize to a nucleic acid sequence of at least one of the control reference gene or miRNA.

In other specific embodiments, the detecting nucleic acid molecules comprised within the diagnostic or prognostic composition of the invention may comprise isolated oligonucleotides that specifically hybridize to a nucleic acid sequence of miR-151-5p, isolated oligonucleotides that specifically hybridize to a nucleic acid sequence of miR-451 and isolated oligonucleotides that specifically hybridize to a nucleic acid sequence of at least one of the control reference gene or miRNA.

Thus, in certain embodiments, the compositions of the invention may further comprise detecting molecules specific for control reference gene or miRNA. Such miRNAs may be used for normalizing the detected expression levels for each of miR-151-5p and miR-451.

The miRNAs described herein can be detected by any methods known to the art, including use of standard oligonucleotides primers and probes, each of which can specifically hybridize to a nucleic acid sequence of at least one of miR-151-5p (SEQ ID NO: 1), and miR-451 (SEQ ID NO: 2), and of at least one control reference miRNA. Such sequences include sequences that are 100% identical to the reverse complement of SEQ ID NOs 1-2. It is understood that such primers and probes can also be less than identical to the reverse complement of SEQ ID NOs 1-2, such as 98%, 95%, 90%, 85% or even less, and that the design of such primers is well known in the art.

It will be appreciated however, that although certain techniques can utilize standard primers and probes, the miRNA 18-24 nt length precludes use of simple amplification techniques. In particular embodiments, miRNA is detected using a DNA microarray, wherein miRNA is extracted from a sample, reverse transcribed, labeled and exposed to DNA microarray with match oligos. miRNA amounts are quantified by measured fluorescence after washing non specifically bound reverse transcribed sequences.

In another embodiment, miRNA can be measured by adding a poly-A tract to extracted RNA, reverse transcribing the poly-adenylated RNAs using a poly-A primer, followed by miRNA-sequence specific qPCR, with specific (miRNA-specific) and non-specific (poly-AA) primers.

In yet another embodiment, extracted miRNA is reverse transcribed using an miRNA structure-specific stem-loop primer. The reverse transcribed miRNA sequences are then amplified and quantified by qPCR with miRNA sequence-specific forward primers and a backward primer specific to the miRNA loop. Design of miRNA stem-loop primers and their use in RT-qPCR is described in Kramer, *Curr. Prot in Molec. Biol.* 15:10, July 2011 (available online at ncbi.nlm.nih.gov/pmc/articles/PMC3152947/). Non-limiting examples of stem-loop primers for use in reverse transcribing miR-151-5p, and miR-451, are based on the description in Kramer (*Curr. Prot in Molec. Biol.* 15:10, July 2011), and are set forth as SEQ ID NOs 3 and 4, respectively. A non-limiting example of the general stem-loop, miR-151-5p, and miR-451 PCR primers are set forth herein as SEQ ID NOs 5-7, respectively. Use of a stem-loop primer in RT-qPCR is illustrated in FIG. 11 (see also Chen et al. *NAR*, 33:e179, 2005).

Non-limiting examples of standard nucleic acid detection methods include PCR (in all of its forms, including qPCR), nucleic acid microarrays, Northern blot analysis, and various forms of primer extension.

According to one optional embodiment, the compositions described by the invention or any components thereof, specifically, the detecting molecules may be attached to a solid support. The solid support may include polymers, such as polystyrene, agarose, sepharose, cellulose, glass, glass beads and magnetizable particles of cellulose or other polymers. The solid-support can be in the form of large or small beads, chips or particles, tubes, plates, or other forms.

As explained earlier, the inventors have analyzed the expression values of miR-151-5p and miR-451 further and discovered specific cutoff values for each miRNA, a deviation from which of at least one of miR-151-5p and miR-451 is indicative of an increased likelihood for relapse in a tested ALL subject, specifically, B-ALL. It should be appreciated that an important step in the prognostic method of the inventions is determining whether the normalized expression value of any one of miR-151-5p and miR-451 is positive and thereby belongs to a pre-established population with an associated specific relapse rate, or is negative and thereby belongs to a pre-established population with a different specific relapse rate. The presence of at least one of miR-151-5p and miR-451 with a positive normalized expression value indicates that the subject belongs to a pre-established population with an associated relapse rate which is higher than the relapse rate associated with, ceteris paribus, subjects where both miR-151-5p and miR-451 have negative normalized expression values, "positive" and "negative" referring to the relation of said expression values to said cutoff value. According to certain embodiments a "positive result" may be determined where a normalized value of any one of miR-151-5p and miR-451 is lower than the cutoff value and therefore predicts relapse.

As used herein, "normalized values" are the quotient of raw expression values of marker genes, namely, miR-151-5p and miR-451, divided by the expression value of a control gene, such as a stably-expressed housekeeping control gene or mirRNA. Any assayed sample may contain more or less biological material than is intended, due to human error and equipment failures. Importantly, the same error or deviation applies to both the marker genes of the invention and to said control gene or mirRNAS, whose expression is essentially constant. Thus, division of the marker gene raw expression value by the control gene or mirRNA raw expression value yields a quotient which is essentially free from any technical failures or inaccuracies (except for major errors which destroy the sample for testing purposes) and constitutes a normalized expression value of said marker gene. This normalized expression value may then be compared with normalized cutoff values, i.e., cutoff values calculated from normalized expression values.

Normalized miR-151-5p and miR-451 expression level values that are higher or lower in comparison with said miRNA's corresponding cutoff value indicate that the examined sample belongs to a population of ALL patients with a specific associated relapse rate, and which indicate a corresponding recommended specific treatment regimen.

In certain embodiments, cutoff values may be used as a control sample, said cutoff values being the result of a statistical analysis of miR-151-5p and miR-451 expression value differences in pre-established different relapse-rate populations.

As used herein, the term "expression value", "level of expression" or "expression level" refers to numerical representation of a quantity of a gene product, which herein is miRNA. For example, miRNA expression values measured in Real-Time Polymerase Chain Reaction, sometimes also referred to as RT-PCR or quantitative PCR (qPCR), represent luminosity measured in a tested sample, where an intercalating fluorescent dye is integrated into double-stranded DNA products of the qPCR reaction performed on reverse-transcribed sample RNA, i.e., test sample RNA converted into DNA for the purpose of the assay. The luminosity is captured by a detector that converts the signal intensity into a numerical representation which is said expression value, in terms of miRNA.

As indicated herein before, the compositions and methods of the invention are particularly intended for predicting and monitoring ALL relapse. The term "relapse", as used herein, relates to the re-occurrence of a condition, disease or disorder that affected a person in the past. Specifically, the term relates to the re-occurrence of ALL. More specifically, the term relates to the re-occurrence of B-ALL or T-ALL. Most specifically, the term relates to the re-occurrence of B-ALL.

In yet a further embodiment, the compositions and methods of the invention may be applicable for providing probability for relapse in patients. Said compositions and methods may be applicable for the prognosis of ALL by analysis of samples taken at the time of initial ALL diagnosis or any other time, including remission. The term "remission", as used herein, relates to the state of absence of disease activity in patients known to have un-curable chronic illness. It is commonly used to refer to absence of active cancer when this disease is expected to manifest again in the future. A partial remission may be defined for cancer as 50% or greater reduction in the measurable parameters of tumor growth as may be found on physical examination, radiologic study, or by biomarker levels from a blood or urine test. A complete remission is defined as complete disappearance of all such manifestations of disease. Each disease or even clinical trial can have its own definition of a partial remission.

The terms "relapse free survival", "disease free survival", RFS or DFS, as referred to herein, relate to the time to relapse of disease. Specifically, the terms relate to the time to relapse of ALL, most specifically, B-ALL. Relapse may be defined biochemically or clinically. Relapse is defined as the recurrence of a disease after apparent recovery. Clinically it is defined as above 5% blasts in the bone marrow. Relapse can also occur in the CNS.

In certain embodiments, the diagnostic or prognostic compositions of the invention are particularly suitable for use according to the prognostic method of the invention.

Thus, the invention further provides compositions for use in the prognosis of ALL as well as monitoring and early diagnosis of ALL relapse.

It should be further appreciated that the composition of the invention may be used for diagnosis of ALL relapse, wherein determination of the expression values of at least one of miR-151-5p, and miR-451 is performed for at least one more temporally-separated test sample. The rate of change of the normalized expression values of at least one of miR-151-5p, and miR-451 between said temporally-separated test samples is being calculated. A case of a negative rate of change of said normalized expression values of at least one of said miR-151-5p, and miR-451 indicates that said subject is in relapse.

According to one embodiment of the composition of the invention, the composition may be used to perform the prognostic method of the invention using a test sample of the subject obtained during diagnosis of ALL.

Furthermore, in another embodiment of the composition of the invention, the composition may be used according to the prognostic method of the invention using at least two test samples of the subject, preferably three or more samples, wherein the samples are collected at different times from the subject.

The composition of the invention may therefore facilitate the monitoring and early sub-symptomatic diagnosis or prediction of a relapse in a subject when used according to the method of the invention for analysis of more than a single sample along the time-course of diagnosis, treatment and follow-up.

In a further aspect, the present invention contemplates a prognostic kit for prognosis of ALL and monitoring or early diagnosis of ALL relapse in a mammalian subject. The kit of the invention comprises: (a) detecting molecules specific for determining the expression value of at least one of miR-151-5p and miR-451. It should be appreciated that miR-151-5p and miR-451 are also denoted by SEQ ID NO.:1 and 2, respectively; (b) detecting molecules specific for determining the expression of at least one control reference gene or miRNA; (c) optionally, at least one control sample selected from a negative control sample and a positive control sample; (d) optionally, instructions for carrying out the detection and quantification of expression of the at least one of miR-151-5p and miR-451 and of at least one control reference gene or miRNA in the sample, and for obtaining an expression value of each of the at least one of miR-151-5p and miR-451; (e) optionally, pre-determined calibration curve providing normalized expression values of the at least one of miR-151-5p and miR-451; and (e) instructions for comparing the expression values of at least one of the miR-151-5p and miR-451 in the test sample with a corresponding predetermined cutoff value of each the at least one of miR-151-5p and miR-451 or with a normalized expression value of at least one of miR-151-5p, and miR-451 obtained from a suitable control sample according to (c).

For using the kit of the invention, one must first obtain samples from the tested subjects. To do so, means for obtaining such samples may be required. Such means for obtaining a sample from the mammalian subject (a) can be any means for obtaining a sample from the subject known in the art. Examples for obtaining e.g. bone marrow or blood samples are known in the art and could be any kind of finger or skin prick or lancet based device, which basically pierces the skin and results in a drop of blood being released from the skin. In addition, aspirating or biopsy needles may be also used for obtaining bone marrow samples. Samples may of course be taken from any other living tissue, or body secretions comprising viable cells, such as biopsies, saliva or even urine.

According to certain optional embodiments, the kit of the invention is contemplated, wherein the clinical criteria comprise at least one of: a. sub-grouping according to B-ALL and T-ALL diagnosis; b. sub-grouping according to minimal residual disease (MRD) high, intermediate and low risk treatment definitions; c. sub-grouping according to response to prednisone on day 8 of treatment; d. sub-grouping according to BFM high, intermediate and low risk treatment definitions; e. sub-grouping according to white blood count (WBC) being over or below 20,000 cells/ml; f. sub-grouping according to patient age being over one and under six years old or otherwise; g. sub-grouping according to CCG high, intermediate and low risk definitions; and h. sub-grouping according to gender.

Specifically, the kit of the invention is contemplated, wherein the patient sub-group clinical criterion is B-ALL diagnosis.

Thus, in certain embodiments the kit of the invention is particularly useful for prognosis of ALL, specifically, B-ALL or T-ALL. More specifically, the kit of the invention is suitable for predicting relapse of B-ALL.

In particularly preferred embodiments, the kit of the invention is considered, wherein the patient sub-group clinical criterion is defined as intermediate or non-high risk according to at least one of minimal residual disease (MRD) high, intermediate and low risk definitions, response to prednisone on day 8 of treatment, BFM high, intermediate and low risk definitions, white blood count (WBC) being over or below 20,000 cells/ml, patient age being over one and under six years old or otherwise, CCG high, intermediate and low risk definitions and gender.

According to certain embodiments, the kit of the invention is used for performing the prognostic method of the invention.

According to other embodiments, the kit of the invention is used for performing the early diagnostic method of the invention.

In particular embodiments of the kit of the invention may be adapted or adjusted for monitoring and performing the early diagnostic method of the invention. More specifically, such kit for early diagnosis of ALL relapse may further comprise: (j) instructions for calculating the rate of change of the normalized expression values of the at least one of miR-151-5p, and miR-451 between the temporally-separated test samples taken from the examined subject. A negative rate of change of the normalized expression values of at least one of said miR-151-5p, and miR-451 indicates that the subject is in relapse.

The kit of the invention may accordingly be used to monitor patient state with respect to ALL therapy, remission or relapse, and provide an early sub-symptomatic molecular sign for a relapse. Such a kit is likely to be extremely useful as an uncomplicated and readily available tool for detecting relapse early on, and providing effective treatment to the relapsing patient.

Thus, the kit allows the prediction and early diagnosis of a relapse on a molecular level, before overt symptoms are observed. This early detection of relapse provides opportunity for more effective therapy, tackling the relapse at a manageable stage.

According to other embodiments, the detecting nucleic acid molecules of the kit of the invention comprise isolated oligonucleotides that specifically hybridize to a nucleic acid sequence of at least one of miR-151-5p and miR-451 and isolated oligonucleotides that specifically hybridize to a nucleic acid sequence of at least one of the control reference gene or miRNA.

According to one embodiment, the detecting molecule comprised within the kit of the invention may be an isolated nucleic acid molecule. Such molecule may be preferably, an isolated oligonucleotide which specifically hybridizes to a nucleic acid sequence of the miRNA of at least one of miR-151-5p, miR-451 and any control reference gene or miRNA.

Accordingly, the kit of the invention may therefore comprise as the detecting molecule for the control reference gene or miRNA, an oligonucleotide which specifically hybridizes to a nucleic acid sequence of at least one control reference gene or miRNA. In certain embodiments, the 5S ribosomal RNA (rRNA), the U6 small nuclear RNA or the miRXplore Universal Reference (UR) may be used as control reference, representing a pool of 979 synthetic miRNA for comparison of multiple samples.

According to a preferred embodiment, such oligonucleotide may be a pair of primers or nucleotide probe or any combination, mixture or collection thereof.

In another embodiment, the present invention relates in part to kits comprising sufficient materials for performing one or more of the diagnostic methods described by the invention. In preferred embodiments, a kit includes one or more materials selected from the following group in an amount sufficient to perform at least one assay.

Thus, according to another optional embodiment, the kit of the invention may further comprise at least one reagent for performing nucleic acid amplification based assay, such as DNA polymerase, buffer, nucleotides, PCR reaction modifiers such as polyethylene glycol (PEG), DMSO, purified water, or pre-made mixes of at least two of said PCR reagents. Such nucleic acid amplification assay may be any one of Real Time PCR, micro arrays, PCR, in situ Hybridization and Comparative Genomic Hybridization.

Control nucleic acid members may be present on the array including nucleic acid members comprising oligonucleotides or nucleic acids corresponding to any control miRNA. Preferably, the 5S ribosomal RNA (rRNA), the U6 small nuclear RNA or the miRXplore Universal Reference (UR) is used as control reference, representing a pool of 979 synthetic miRNA for comparison of multiple samples. Control nucleic acid members are calibrating or control miRNA whose function is not to tell whether a particular "key" miRNA of interest is expressed, but rather to provide other useful information, such as background or basal level of expression, or indeed indicate a general fault in the performed assay or sample.

Some embodiments relate to the kit of the invention, wherein the detecting nucleic acid molecules comprise isolated oligonucleotides that specifically hybridize to a nucleic acid sequence of miR-151-5p and isolated oligonucleotides that specifically hybridize to a nucleic acid sequence of at least one of the control reference gene or miRNA.

Other embodiments relate to the kit of the invention, wherein the detecting nucleic acid molecules comprise isolated oligonucleotides that specifically hybridize to a nucleic acid sequence of miR-451 and isolated oligonucleotides that specifically hybridize to a nucleic acid sequence of at least one of the control reference gene or miRNA.

Yet other embodiments relate to the kit of the invention, wherein the detecting nucleic acid molecules comprise isolated oligonucleotides that specifically hybridize to a nucleic acid sequence of miR-151-5p, isolated oligonucleotides that specifically hybridize to a nucleic acid sequence of miR-451 and isolated oligonucleotides that specifically hybridize to a nucleic acid sequence of at least one of the control reference gene or miRNA.

According to a preferred embodiment, the kits provided by the invention may further comprise suitable means and reagents for preparing or isolating nucleic acids from said sample.

In certain embodiments, the detecting molecules of the kit of the invention are oligonucleotides selected from a pair of primers or nucleotide probe.

Specific embodiments relate to the kit of the invention, further comprising at least one reagent for performing a nucleic acid amplification based assay selected from the group consisting of a Real-Time PCR, micro arrays, PCR, in situ Hybridization and Comparative Genomic Hybridization.

Thus, another example is a microarray RNA assay, where, according to one method, test sample RNA is conjugated to a fluorescent dye and allowed to specifically hybridize with complementary oligonucleotide probes fixed in pre-determined positions on a stationary phase. After excess RNA is washed away, a detector converts the luminosity of each bound fluorescent-dye conjugated RNA species to a numerical representation, which are expression values.

More specifically, for nucleic acid microarray kits, the kits may generally comprise probes attached to a support surface. The probes may be labeled with a detectable label. In a specific embodiment, the probes are specific for at least one of miR-151-5p, miR-451 and any control gene product. The microarray kits may comprise instructions for performing the assay and methods for interpreting and analyzing the data resulting from the performance of the assay. The kits may also comprise hybridization reagents and/or reagents necessary for detecting a signal produced when a probe hybridizes to a target nucleic acid sequence. Generally, the materials and reagents for the microarray kits are in one or more containers. Each component of the kit is generally in its own a suitable container.

For Real-Time RT-PCR kits, the kits generally comprise pre-selected primers specific for particular RNA products of at least one of miR-151-5p, miR-451 and any control gene product. The RT-PCR kits may also comprise enzymes suitable for reverse transcribing and/or amplifying nucleic acids (e.g., polymerases such as Taq), and deoxynucleotides and buffers needed for the reaction mixture for reverse transcription and amplification. The RT-PCR kits may also comprise probes specific for at least one of miR-151-5p, miR-451 and any control gene product. The probes may or may not be labeled with a detectable label (e.g., a fluorescent label). Each component of the RT-PCR kit is generally in its own suitable container. Thus, these kits generally comprise distinct containers suitable for each individual reagent, enzyme, primer and probe. Further, the RT-PCR kits may comprise instructions for performing the assay and methods for interpreting and analyzing the data resulting from the performance of the assay.

Certain embodiments consider the kit of the invention, wherein the sample is a biological sample, the sample is any one of bone marrow, lymph fluid, blood cells, blood, serum, plasma, urine, sputum, saliva, faeces, semen, spinal fluid or CSF, the external secretions of the skin, respiratory, intestinal, and genitourinary tracts, tears, milk, any human organ or tissue, any sample obtained by lavage optionally of the breast ductal system, plural effusion, samples of in vitro or ex vivo cell culture and cell culture constituents.

More specific embodiments consider the kit of the invention, wherein the sample is a sample of bone marrow.

It should be thus appreciated that any of the kits of the invention may optionally further comprises solid support, such as plates, beads, tube or containers. These may be specifically adopted for performing different detection steps or any nucleic acid amplification based assay, as described for example by the method of the invention. It should be further noted that any substance or ingredient comprised within any of the kits of the invention may be attached, embedded, connected or linked to any solid support.

It should be noted that any of the detecting molecules used by the compositions, methods and kits of the invention may be labeled by a detectable label. The term "detectable label" as used herein refers to a composition or moiety that is detectable by spectroscopic, photochemical, biochemical, immunochemical, electromagnetic, radiochemical, or chemical means such as fluorescence, chemifluoresence, or chemiluminescence, or any other appropriate means. Preferred detectable labels are fluorescent dye molecules, or fluorochromes, such fluorescein, phycoerythrin, CY3, CY5, allophycocyanine, Texas Red, peridenin chlorophyll, cyanine, FAM, JOE, TAMRA, tandem conjugates such as phycoerythrin-CY5, and the like. These examples are not meant to be limiting.

It should be appreciated that all method and kits described herein, preferably comprises any of the compositions of the invention.

It should be recognized that the nucleic acid sequences used by the kits of the present invention relate, in some embodiments, to their isolated form, as isolated polynucleotides (including for all transcripts) and/or oligonucleotides (including for all segments, amplicons and primers). It should be noted that the terms "oligonucleotide" and "polynucleotide" may optionally be used interchangeably.

It should be noted that the prognostic, monitoring and diagnostic methods, compositions and kits of the invention are particularly applicable for prognosis of ALL and prediction of ALL relapse in a subject. By the terms "subject", "subject in need" and "patient", used interchangeably herein, it is meant any organism who may be affected by ALL, and to whom the prognostic, diagnostic or treatment methods herein described is desired, including humans, domestic and non-domestic mammals such as humans, canine and feline subjects, bovine, equine and murine subjects and even rodents. More specifically, the subject is a human. It should be appreciated that the subject may be a pediatric patient or an adult patient. The subject may be at least 1 week old, two weeks old, three weeks old, one month old, two months old, three months old four months old, five months old, six months old, seven months old, eight months old, nine months old, ten months old, eleven months old, 1 year old, at least 3 years old, at least 6 years old, at least 10 years old, at least 20 years old, at least 30 years old, at least 40 years old, at least 50 years old, at least 60 years old, at least 70 years old, at least 80 years old, at least 90 years old or even older. Furthermore, the subject may be a male or a female.

In the fourth aspect, the present invention provides a method of preventing or delaying the relapse of acute lymphoblastic leukemia, comprising the step of administering to a subject in need thereof a therapeutically effective amount of at least one of miR-151-5p and miR-451, or any gene encoding the at least one of miR-151-5p and miR-451, pri-miRNA, pre-miRNA thereof, a construct encoding the at least one of miR-151-5p and miR-451, any combinations thereof or any composition comprising the same. In certain embodiments, miR-151-5p and miR-451 are denoted by SEQ ID NO. 1 and 2, respectively. Additional therapeutic agents, specifically, any immunomodulatory agent or known medicament, may be either combined with at least one of the said miR-151-5p and miR-451 used by the invention or may be administered separately in an additional separate step having an optional different mode of administration.

Some embodiments of the invention contemplate a treatment of a subject suffering from a proliferative disorder, specifically, ALL, with the micro-RNAs of the invention, specifically, miR-151-5p and/or miR-451, wherein the treatment results in the inhibition of abnormal cellular proliferation by about 5% to about 99.9%, specifically, about 5% to about 10%, about 10% to about 15%, about 15% to about 20%, about 20% to about 25%, about 25% to about 30%, about 35% to about 40%, about 40% to about 45%, about 45% to about 50%, about 50% to about 55%, about 55% to about 60%, about 65% to about 70%, about 75% to about 80%, about 80% to about 85%, about 85% to about 90%, about 90% to about 95%, about 95% to about 99.9%.

Other specific embodiments of the invention contemplate a treatment of a subject that is either currently suffering from a proliferative disorder, or previously suffered from a proliferative disorder and is in remission, specifically, said proliferative disorder is ALL, with the micro-RNAs of the invention, specifically, miR-151-5p and/or miR-451, wherein the treatment results in the inhibition or prevention of relapse of the disease in about 5% to about 99.9%, specifically, about 5% to about 10%, about 10% to about 15%, about 15% to about 20%, about 20% to about 25%, about 25% to about 30%, about 35% to about 40%, about 40% to about 45%, about 45% to about 50%, about 50% to about 55%, about 55% to about 60%, about 65% to about 70%, about 75% to about 80%, about 80% to about 85%, about 85% to about 90%, about 90% to about 95%, about 95% to about 99.9%.

The terms "inhibition", "moderation" or "attenuation" as referred to herein, relate to the retardation, restraining or reduction of a process by any one of about 1% to 99.9%, specifically, about 1% to about 5%, about 5% to 10%, about 10% to 15%, about 15% to 20%, about 20% to 25%, about 25% to 30%, about 30% to 35%, about 35% to 40%, about 40% to 45%, about 45% to 50%, about 50% to 55%, about 55% to 60%, about 60% to 65%, about 65% to 70%, about 75% to 80%, about 80% to 85% about 85% to 90%, about 90% to 95%, about 95% to 99%, or about 99% to 99.9%.

The method of the invention involves administration of therapeutically effective amount of the micro-RNAs of the invention. The term "effective amount" as used herein is that determined by such considerations as are known to the man of skill in the art. The amount must be sufficient to prevent or ameliorate proliferative disorders, specifically, ALL, most specifically, B-ALL. In specific embodiments, the amount must be sufficient to prevent inhibit relapse of a disease, specifically, ALL, most specifically, B-ALL. Dosing is dependent on the severity of the symptoms and on the responsiveness of the subject to the active drug. Medically trained professionals can easily determine the optimum dosage, dosing methodology and repetition rates. In any case, the attending physician, taking into consideration the age, sex, weight and state of the disease of the subject to be treated, as well as other clinical parameters according to the invention, will determine the dose.

More specifically, the compositions containing the micro-RNAs of the present invention, or any combination, mixture or cocktail thereof can be administered for prophylactic and/or therapeutic treatments. In therapeutic application, compositions are administered to a patient already affected by a proliferative disorder (e.g., ALL) in an amount sufficient to cure or at least partially arrest the condition and its complications, specifically, relapse of the disease. An amount adequate to accomplish this is defined as a "therapeutically effective dose." Amounts effective for this use will depend upon the severity of the condition and the general state of the patient. Single or multiple administrations on a daily, weekly or monthly schedule can be carried out with dose levels and pattern being selected by the treating physician.

The term "prophylaxis" refers to prevention or reduction the risk of occurrence of the biological or medical event that is sought to be prevented in a tissue, a system, animal or human by a researcher, veterinarian, medical doctor or other clinician, and the term "prophylactically effective amount" is intended to mean that amount of a pharmaceutical composition that will achieve this goal.

In prophylactic applications, compositions containing the micro-RNAs of the invention or any combination, mixture or cocktail thereof are administered to a patient who is at risk of developing the disease state to enhance the patient's resistance. Such an amount is defined to be a "prophylactically effective dose". In this use, the precise amounts again depend upon the patient's state of health and general level of immunity, as well as other clinical parameters according to the invention.

As used herein, "disease", "disorder", "condition" and the like, as they relate to a subject's health, are used interchangeably and have meanings ascribed to each and all of such terms.

According to certain embodiments, the condition or disease to be treated by the method of the invention may be ALL. "Acute lymphoblastic leukemia (ALL)" as used herein is a malignant (clonal) disease of the bone marrow in which early lymphoid precursors proliferate and replace the normal hematopoietic cells of the marrow. Acute lymphoblastic leukemia (ALL) may be distinguished from other malignant lymphoid disorders by the immunophenotype of the cells, which is similar to B- or T-precursor cells. Immunochemistry, cytochemistry, and cytogenetic markers may also aid in categorizing the malignant lymphoid clone.

The malignant cells of acute lymphoblastic leukemia (ALL) are lymphoid precursor cells (i.e., lymphoblasts) that are arrested in an early stage of development. This arrest is caused by an abnormal expression of genes, often as a result of chromosomal translocations. The lymphoblasts replace the normal marrow elements, resulting in a marked decrease in the production of normal blood cells. Consequently, anemia, thrombocytopenia, and neutropenia occur to varying degrees. The lymphoblasts also proliferate in organs other than the marrow, particularly the liver, spleen, and lymph nodes.

Patients with pediatric acute lymphoblastic leukemia (ALL) may be divided into the following three prognostic/treatment groups according to BFM 2000.

Standard risk includes (1) no adverse cytogenetics, (2) age between 1 and 6 years, (3) good response to prednisone treatment on day 8. High risk includes at least one of (1) cytogenetic abnormalities (e.g. t(9;22) and t(4;11)), (2) under 1 year of age, (3) poor response to prednisone treatment on day 8 and (4) hypodiploidy. Intermediate risk includes those whose age is between 1 to 6, show no adverse cytogenetics, no hypodiploidy and a good response to prednisone on day 8 of treatment, as well as those whose condition does not meet the criteria for either standard risk or high risk.

Importantly, these criteria are second only to PCR-MRD diagnosis. PCR-MRD risk stratification is performed after MRD analysis on days 33 and 78 from the beginning of treatment. PCR-MRD standard risk is defined as a negative MRD finding on days 33 and 78. PCR-MRD high risk is defined as a finding of 10-3 leukemic cells (1 leukemic cell in 1000 normal cells) on day 78. All other findings are defined as intermediate risk. In the present invention, the MRD test was performed by PCR amplification of immunoglobulin and T-cell rearrangement sites (PCR-MRD), and interpreted according to the guidelines of the European Study Group for PCR-MRD detection in ALL (ESG-MRD-ALL).

It is understood that the prognostic grouping by the initial clinical risk grouping by the parameters of cytogenetic aberrations, age, prednisone response and ploidy does not imply a different treatment regime for the diagnosed patient treated under the BFM treatment regime. It is understood that the USA Children's Oncology Group (COG) treatment regime administers a different induction therapy according to the National Cancer Institute (NCI) prognostic group determined by white blood cell (WBC) count, age and cytogenetics by not administering anthracycline during induction therapy to NCI-SR and administering anthracycline to NCI-HR. Moreover, as MRD risk classification becomes available after day 78 of treatment, it replaces the previous classification and provides a basis for planning treatment for the patient. Until such time that the MRD risk group prognosis replaces the previous risk classification, a standard treatment is provided to all patients.

An important feature of the present invention is the ability to provide a prognostic indication at the time of initial diagnosis, which is at least as accurate as the PCR-MRD-based prognosis and as accurate as WBC and age. Thus, the present invention allows the planning and administering of an appropriate treatment regimen immediately after diagnosis, which fits into the COG protocol, rather than 78 days after beginning a standard, non-differentiated treatment as in the BFM protocol.

ALL is a biologically heterogeneous disorder, so that morphologic, immunologic, cytogenetic, biochemical, and molecular genetic characterizations of leukemia lymphoblasts are needed to establish the diagnosis or to exclude other possible causes of bone marrow failure and, finally, to classify ALL subtypes. ALL may be either asymptomatic or acute with life-threatening hemorrhage, infection, or episode of respiratory distress. Although ALL is a disease primarily of the bone marrow and peripheral blood, any organ or tissue may be infiltrated by the abnormal cells. The most frequent signs are lymphadenopathies, hepatosplenomegaly, fever, signs of hemorrhage, and bone pain. Biological findings include hyperleukocytosis due to circulating lymphoblasts, anemia and thrombocytopenia. Diagnosis is established by bone marrow biopsy, which evidences the leukemic cells infiltration. Most of the cases of ALL show chromosomal and genetic abnormalities, which occur spontaneously in important regulatory genes in a lymphoid cell population. The most common ALL translocation, the t(12;21), appears to have good prognostic implications. Four main treatment elements can be generally recognized in chemotherapy protocols adopted by international cooperative groups: induction with the aim of complete remission, CNS preventive therapy, consolidation/reinduction, and maintenance therapy. The survival rate for children younger than 15 years of age reaches about 75%, but, despite the significant improvement of outcome during the last decades, still roughly 25% of patients suffer from a relapse of the disease. Even if the management of relapse remains largely controversial, an increasing use of high dose chemotherapy blocks and stem cell transplantation is adopted in most cases. With the need to stratify patients in risk groups and to provide risk-adapted therapy, treatment requires high levels of organization, expertise and knowledge.

The present invention relates to the treatment of subjects, or patients, in need thereof. By "patient" or "subject in need" it is meant any organism who may be affected by the above-mentioned conditions, and to whom the treatment and diagnosis methods herein described is desired, including humans, domestic and non-domestic mammals such as canine and feline subjects, bovine, simian, equine and murine subjects, rodents, domestic birds, aquaculture, fish and exotic aquarium fish. It should be appreciated that the treated subject may be also any reptile or zoo animal. More specifically, the composition of the invention is intended for mammals. By "mammalian subject" is meant any mammal for which the proposed therapy is desired, including human, equine, canine, and feline subjects, most specifically humans. It should be noted that specifically in cases of non-human subjects, the method of the invention may be performed using administration via injection, drinking water, feed, spraying, oral gavage and directly into the digestive tract of subjects in need thereof. It should be further noted that particularly in case of human subject, administering of the miRNAs of the invention to the patient includes both self-administration and administration to the patient by another person.

The term "treatment or prevention" refers to the complete range of therapeutically positive effects of administrating to a subject including inhibition, reduction of, alleviation of, and relief from, ALL and illness, ALL symptoms or undesired side effects or ALL related disorders. More specifically, treatment or prevention of relapse includes the prevention or postponement of development of the disease, prevention or postponement of development of symptoms and/or a reduction in the severity of such symptoms that will or are expected to develop. These further include ameliorating existing symptoms, preventing—additional symptoms and ameliorating or preventing the underlying metabolic causes of symptoms. It should be appreciated that the terms "inhibition", "moderation", "reduction" or "attenuation" as referred to herein, relate to the retardation, restraining or reduction of a process by any one of about 1% to 99.9%, specifically, about 1% to about 5%, about 5% to 10%, about 10% to 15%, about 15% to 20%, about 20% to 25%, about 25% to 30%, about 30% to 35%, about 35% to 40%, about 40% to 45%, about 45% to 50%, about 50% to 55%, about 55% to 60%, about 60% to 65%, about 65% to 70%, about 75% to 80%, about 80% to 85% about 85% to 90%, about 90% to 95%, about 95% to 99%, or about 99% to 99.9%.

Specifically preferred embodiments relate to the prophylactic method of the invention, wherein the subject suffered from B-ALL and is presently in remission.

In other embodiments, the prophylactic method of the invention comprises the step of administering a therapeutically effective amount of miR-151-5p or a gene encoding miR-151-5p, pri-miR-151-5p, pre-miR-151-5p, a construct encoding the miR-151-5p, any combinations thereof or any composition comprising the same.

In further embodiments, the prophylactic method of the invention comprises the step of administering a therapeutically effective amount of miR-451 or a gene encoding miR-451, pri-miR-451, pre-miR-451, a construct encoding the miR-451, any combinations thereof or any composition comprising the same.

In yet further embodiments, the prophylactic method of the invention comprises the step of administering a therapeutically effective amount of a combination of miR-151-5p and miR-451 or any gene encoding the miR-151-5p and miR-451, pri-miRNA, pre-miRNA thereof, a construct encoding miR-151-5p and miR-451 or any composition comprising the same.

In yet another aspect, the inventors also contemplate a therapeutic composition comprising a therapeutically effective amount of at least one of miR-151-5p and miR-451, also denoted by SEQ ID NO.:1 and 2, or any gene encoding the at least one of miR-151-5p and miR-451, pri-miRNA, pre-miRNA thereof, a construct encoding the at least one of miR-151-5p and miR-451, any combinations thereof or any composition comprising the same. The therapeutic composition of the invention is particularly suitable for preventing relapse of ALL.

Described herein are methods of treating an ALL patient thereby reducing the risk of ALL relapse. The described methods involve first determining, through the methods described herein, the risk of relapse in a given patient through determining the expression of mir-151-5p and/or mir-451. Once the risk of relapse is determined, the patient can be given a treatment appropriate for reducing relapse. As noted herein, the described miRNA methods for determining relapse risk provide a clinician information regarding possible relapse weeks before any method currently in use. Accordingly, the treatments administered following relapse determination are given to a patient only as a result of the novel methods described herein.

Most patients diagnosed with acute lymphoblastic leukemia (ALL) enroll in a clinical trial or follow a standard treatment protocol. Several treatment protocols are known to the art, of which several are described herein. Regardless of any differences between the various treatment protocols, distinctions are made amongst all protocols between the appropriate treatment given to patients determined to be standard and high risk for ALL relapse.

In a particular example, such distinctions in treatment are as summarized by the American Cancer Society as follows; this description is not a detailed account of the treatment but points out important differences in treatment of ALL patients according to their risk stratification in USA (available online at cancer.org/acs/groups/cid/documents/webcontent/003095-pdf.pdf).

The main treatment for children with ALL is chemotherapy, which is usually divided into 3 phases in which the patient is treated according to risk stratification:

1. Induction (typically 1 month)—Several treatment protocols determine Induction therapy by the patients'

National Cancer Institute Risk (NCI) determined by white blood cell (WBC) count, age and certain cytogenetic findings.
  a. NCI-Standard Risk patients receive chemotherapy drugs L-asparaginase and vincristine, and a steroid drug (usually dexamethasone).
  b. NCI-High Risk patients receive chemotherapy drugs L-asparaginase and vincristine, steroid drug (usually dexamethasone) and anthracycline class (daunorubicin is the one most often used) is typically added.
2. Consolidation (also called intensification)—The MRD findings are used to help determine the intensification of treatment at this stage;
  a. Standard Risk ALL—are usually treated with drugs such as methotrexate and 6-mercaptopurine or 6-thioguanine, but regimens differ among cancer centers. Vincristine, L-asparaginase, and/or prednisone may also be added.
  b. High Risk ALL—generally receive more intense chemotherapy. Extra drugs such as L-asparaginase, doxorubicin (Adriamycin), etoposide, cyclophosphamide, and cytarabine (ara-C) are often used, and dexamethasone is substituted for prednisone. There may be a second round of intense chemotherapy with the same drugs.
3. Maintenance
  a. Standard risk—Most treatment plans use daily 6-mercaptopurine and weekly methotrexate, given as pills, often along with vincristine, which is given intravenously, and a steroid (prednisone or dexamethasone).
  b. High risk—Some children at higher risk may receive more intense maintenance chemotherapy and intrathecal therapy.

In another embodiment, ALL treatment follows the International Berlin-Frankfurt-Munster Study Treatment Protocol, or a variant thereof. From 2002 to 2007, the International Berlin-Frankfurt-Munster Study Group conducted a prospective randomized clinical trial (ALL IC-BFM 2002) for the management of childhood acute lymphoblastic leukemia (ALL) in 15 countries on three continents (Stary J, Zimmermann M, Campbell M, et al., Intensive chemotherapy for childhood acute lymphoblastic leukemia: results of the randomized intercontinental trial ALL IC-BFM 2002. J Clin Oncol. 2014 Jan. 20; 32:174-184). The following is a synopsis of the treatment in this study.

1. Induction (2 months)
  a. Standard Risk
    i. Phase 1 (1 month)—Prednisone, Vincristine, Daunorubicin (2 Doses), L-asparaginase, Methotrexate
    ii. Phase 2 (1 month)—Cyclophosphamide, Cytarabine, 6-mercaptopurine, Methotrexate
  b. Intermediate and High Risk
    i. Phase 1 (1 month)—Prednisone, Vincristine, Daunorubicin (4 Doses), L-asparaginase, Methotrexate
    ii. Phase 2 (1 month)—Cyclophosphamide, Cytarabine, 6-mercaptopurine, Methotrexate
2. Consolidation (also called intensification)
  a. Standard and Intermediate Risk
    i. 6-mercaptopurine, Methotrexate (intravenous), Methotrexate (intrathecal). Intermediate patients received 4 doses of Methotrexate (intrathecal)
  b. High Risk—Managed with chemotherapy as well as radiotherapy. After a rest of two weeks consolidation phase continues in 3 blocks (Each Block is 11 days with periods of recovery between blocks):
    i. Block 1—Dexamethasone, Vincristine, Methotrexate, Cyclophosphamide, Cytarabine, L-asparaginase, Methotrexate/cytarabine/prednisolone
    ii. Block 2—Dexamethasone, Vindesine, Methotrexate, Ifosfamide, Daunorubicin, L-asparaginase, Methotrexate/cytarabine/prednisolone
    iii. Block 3—Dexamethasone, Cytarabine, Etoposide, L-asparaginase, Methotrexate/cytarabine/prednisolone Maintenance Therapy—Methotrexate and 6-Mercaptopurine.

In yet another embodiment, the treatments described herein follow the protocol described as the United Kingdom (UK) UKALL2003 Protocol, as summarized online at who.int/selection_medicines/committees/subcommittee/2/cytotoxic_review.pdf.

This protocol consists of three regimens depending on the risk i.e. Low Risk (Regimen A), Moderate Risk (Regimen B) and High Risk (Regimen C).

1. Induction (2 months)
  a. Low Risk—Three drug induction (duration 5 weeks) with dexamethasone as steroid of choice.
  b. Moderate Risk—Four drug induction (duration 5 weeks) with dexamethasone as steroid of choice.
  c. High Risk—Four drug induction with dexamethasone as steroid of choice.
2. Augmented BFM Consolidation (duration 9 weeks)
  a. High Risk—all patients receive 6-mercaptopurine.
3. Interim Maintenance I
  a. Low Risk—(duration 8 weeks) with dexamethasone and 6-mercaptopurine.
  b. Moderate Risk—(duration 8 weeks)—dexamethasone and 6-mercaptopurine.
4. Interim Capizzi Maintenance I (duration 8 weeks)
  a. High Risk—PEG asparaginase and escalating doses of IV methotrexate.
5. Delayed Intensification
  a. Low Risk—(duration 7 weeks) with 6-mercaptopurine in reconsolidation;
  b. Moderate Risk—(duration 7 weeks); 6-mercaptopurine in reconsolidation;
  c. High Risk—(duration 8 weeks); 6-mercaptopurine in reconsolidation; PEG asparaginase;
6. Interim Maintenance II
  a. Low Risk—for patients allocated two delayed intensifications) (duration 8 weeks) with dexamethasone and 6-mercaptopurine;
  b. Moderate Risk—for patients allocated two delayed intensifications (duration 8 weeks) with dexamethasone and 6-mercaptopurine;
  c. High Risk—(duration 8 weeks); 6-mercaptopurine in reconsolidation; PEG asparaginase;
7. Maintenance Therapy
  a. Low Risk—with dexamethasone and 6-mercaptopurine to end of week 112 for girls and end of 164 for boys. Delays accrued during phases I-VI are taken off during the maintenance period.
  b. Moderate Risk—with dexamethasone and 6-mercaptopurine to end of week 114 for girls and end of week 166 for boys. Delays accrued during phases I-VI are taken off the maintenance period.

High Risk—with dexamethasone and 6-mercaptopurine to the end of week 118 for girls and end of week 170 for boys. Delays accrued during phases I-VI are taken off the maintenance period.

In a particular embodiment, the described treatment methods are part of a system of treating an ALL patient. The described systems involve first determining the risk of ALL relapse, through the described methods of detecting the expression of at least one of miR-151-5p and miR-451. Once it is determined that a subject has an increased risk of ALL relapse, an appropriate treatment is given, tailored to the determined relapse risk.

As described herein, typical treatments for ALL patients are determined by the prognosis of a high or non-high risk of relapse. Standard protocols (for example, but not limited to, BFM high risk and COG high risk, see Borowitz et al., Blood (2008); 111:5477-5485; and summarized in Hunger, *Am Soc Clin Oncol Educ Book.* 2012, 611-615), have been developed to treat high risk patients more intensively than non-high risk patients and reduce treatment intensity in standard risk patients. Among the differences in such drug protocols between patients who have a high and non-high risk of relapse includes early use of an anthracylcine drug such as daunorubicin in the course of treatment.

Prior to the described systems, determining appropriate ALL treatment not only relied on entirely different clinical parameters (e.g. WBC count, prednisone response), but such determinations were made days or even weeks after the initial diagnosis. In contrast, the current systems can determine appropriate treatment at the time of initial ALL diagnosis, following a test for expression of, and at least one of miR-151-5p and miR-451. Once a determination is made that a patient may have an increased risk of relapse, a "high risk" treatment protocol (such as those employing an anthracycline) can be administered.

The current systems are based on the understanding that modern healthcare services are provided by large entities within which multiple healthcare services are given to a patient. Particular non-limiting examples of such entities include physicians groups, hospital consortiums or networks, and public or private health maintenance organizations. Within these entities, a patient's health care may be managed by a single actor, such as a physician, nurse practitioner, and the like, but specialized services are provided to the patient by multiple actors within the system, such as diagnosticians and specialists. It is recognized that in particular embodiments, certain services may be outsourced to a provider outside of the main service provider. Therefore, the diagnostician may be different from the primary physician or oncologist. However, in all embodiments, it is the main service provider, or representative or employee thereof, who is directing the described systems of treatment.

Disclosed and described, it is to be understood that this invention is not limited to the particular examples, methods steps, and compositions disclosed herein as such methods steps and compositions may vary somewhat. It is also to be understood that the terminology used herein is used for the purpose of describing particular embodiments only and not intended to be limiting since the scope of the present invention will be limited only by the appended claims and equivalents thereof.

It must be noted that, as used in this specification and the appended claims, the singular forms "a", "an" and "the" include plural referents unless the content clearly dictates otherwise.

Throughout this specification and the Examples and claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The following examples are representative of techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without departing from the spirit and intended scope of the invention.

EXAMPLES

Materials miRNeasy mini kit (Qiagen, Hilden, Germany)
Agilent 2100 Bioanalyzer platform (Agilent technologies)
a-Hyb™ hybridization station (Miltenyi biotech, Bergisch Gladbach, Germany)
miRXplore™ (Miltenyi biotech, Bergisch Gladbach, Germany)
PIQOR™ analyzer (Miltenyi biotech, Bergisch Gladbach, Germany)
LNA™ primers (Exiqon, Vedbaek, Denmark)
LightCycler 480 (Roche, Rotkreuz, Switzerland)

Experimental Procedures

Patient Material Collection

Bone marrow (BM) aspirates at the time of diagnosis were obtained from 95 pediatric ALL patients and the percentage of leukemic blasts in those samples was at least 80%. The patients were 53 males and 42 females, with a median age of 6.6 years (range 0.3-18). Twenty-eight patients had T-ALL, 46 patients had a WBC>20000, 18 patients were poor prednisone responders, 32 patients were clinically classified as BFM high-risk, 40 intermediate-risk and 23 standard-risk, 31 patients had relapsed. The median follow-up of patients was 69 months (range 6-296). All patients were treated at Schneider children's medical center of Israel. 4, 16, 25 and 50 patients were treated according to the INS-84, INS-89, INS-98 and INS-2003 protocols respectively [Stark B et al., Leukemia. (2010); 24: 419-424; INS-2003]. This study was approved by the local and national ethical committees and all patient material was obtained according to the Declaration of Helsinki.

RNA Isolation

RNA for the miRNA-microarray and for qRT-PCR was isolated out of $10^7$ cells from BM aspirates according to the miRNeasy mini kit. RNA concentration was determined by measuring the absorbance at 260 nm with a $A_{260}/A_{280}$ ratio of 1.8 or higher to fulfill the microarray requirements.

miRNA Expression Profile

Microarray analysis was performed on 48 ALL samples using the service of Miltenyi biotech (Miltenyi biotech, Bergisch Gladbach, Germany). RNA quality was assessed by Agilent 2100 Bioanalyzer platform and visualized by means of agarose gel electrophoresis. Sample labeling was performed according to the miRXplore™ user manual. For those samples which revealed a sufficient RNA yield, 2 µg total RNA were used for the labeling, for all other samples the available amount of total RNA was used. Subsequently, the fluorescently labeled samples were hybridized overnight to miRXplore™ microarrays using the a-Hyb™ hybridization station. Control samples were labeled with Hy3 and experimental samples were labeled with Hy5. The miRXplore Universal Reference (UR) was used as control samples and it represents a pool of 979 synthetic miRNA for comparison of multiple samples. Fluorescent signals of the hybridized miRXplore™ microarray were detected using a laser scanner from Agilent (Agilent technologies). Normalized Hy5/Hy3 ratios were calculated for each quadruplicate by PIQOR™ analyzer. Only miRNAs that had a signal that was equal or higher than the 50% percentile of the background signal intensities were used for the Hy5/Hy3 ratio calculation. Data was transformed to Log 2 ratios for data clustering (2D-clustering using Pearson correlation and average linkage).

qRT-PCR

In order to verify the miRNA-microarray results, qRT-PCR was performed on 95 samples. cDNA was made from 100 ng according to the manufacturer instructions (Exiqon, Vedbaek, Denmark). qRT-PCR was performed with LNA™ primers (Exiqon) for the selected miRNAs and 5S that was used as a reference during all the analyses. The qRT-PCR reactions were performed in duplicates with the LightCycler 480.

Statistical Analyses miRNA expression data were analyzed with PASW Statistics 18 (SPSS inc. Chicago, Ill., USA). For correlation with age, gender, WBC, d8, type and risk group the Fisher's exact test was used. In order to determine the optimal cutoff value, ROC analysis was performed for each miRNA. Kaplan-Meier analyses were performed to evaluate whether the selected miRNA correlate with relapse and COX-regression was used to determine whether those miRNA can be regarded as independent risk factors. A p-value of <0.05 was considered as significant. It should be noted that the probability of RFS was calculated using Kaplan Meier analysis, applying different weight to patient mortality according to the length of the preceding survival period.

Example 1

Initial miRNA Screening for ALL Clinical Parameters-Correlated Expression

From the panel of 979 synthetic miRNA that were used in this analysis, only 116 and 116 were significantly higher and lower, respectively, than the universal reference (UR). Clustering with age, type, WBC, d8, risk group and relapse revealed 10, 33, 20, 14, 19 and 33 miRNAs, respectively, whose expression was significantly lower in ALL, while 9, 36, 16, 12, 14 and 28 miRNAs, respectively, were significantly higher expressed in ALL. Based on interesting clustering with clinical parameters, three miRNAs that demonstrated lower expression in ALL were selected for validation and further studies. miR-708 expression correlated with all six clinical parameters, miR-151-5p correlated with all of them except for relapse, and miR-451 with all of them except for age.

Example 2 miR-151-5p and miR-451 Expression Correlates with Various ALL Clinical Parameters In order to validate the array results, a small panel of 30 samples was assessed for miRNA expression. As a general rule, the median expression level of each miRNA was taken as a cutoff during the analysis. miR-708 was hardly expressed in this set of pediatric ALL samples and due to sensitivity limits, this miRNA was not used in the large validation set. miR-151-5p and miR-451 showed some interesting correlations with clinical parameters and therefore were chosen to be tested on a panel of 95 patients.

Based on ROC analysis for each miRNA, the cutoff of miR-151-5p was set at 0.00015 (p=0.02, sensitivity=71%, specificity=61%) and the cutoff of miR-451 was set at 0.001 (p=0.02, sensitivity=68%, specificity=62%). Correlation between the two miRNAs and the clinical parameters can be can be found in Table 1 below. Briefly, lower expression of miR-151-5p seems to significantly correlate with all the adverse clinical parameters except for gender, while low expression of miR-451 only correlates with poor prednisone response and HR-classification.

TABLE 1

Correlation between miRNA expression level and clinical parameters in pediatric ALL.

| | MIR-151-5p (n = 95) | | | MIR-451 (n = 95) | | |
|---|---|---|---|---|---|---|
| | <cutoff (n = 47) | >cutoff (n = 48) | p-value | <cutoff (n = 45) | >cutoff (n = 50) | p-value |
| Age < 1 or Age > 6 (n = 52) | 32 (68%) | 20 (42%) | | 25 (56%) | 27 (54%) | |
| 1 < Age < 6 (n = 43) | 15 (32%) | 28 (58%) | 0.0134 | 20 (44%) | 23 (46%) | NS |
| Male (n = 53) | 31 (66%) | 22 (46%) | | 26 (58%) | 27 (54%) | |
| Female (n = 42) | 16 (34%) | 26 (54%) | 0.0635 | 19 (42%) | 23 (46%) | NS |
| WBC > 20000 (n = 46) | 34 (72%) | 12 (25%) | | 25 (56%) | 21 (42%) | |
| WBC < 2000 (n = 49) | 13 (18%) | 36 (75%) | 0 | 20 (44%) | 29 (58%) | NS |
| PPR (n = 18) | 15 (32%) | 3 (6%) | | 14 (31%) | 4 (8%) | |
| GPR (n = 77) | 32 (68%) | 45 (94%) | 0.0016 | 31 (69%) | 46 (92%) | 0.0075 |
| High risk (HR + infant) (n = 32) | 24 (51%) | 8 (17%) | | 23 (51%) | 9 (18%) | |
| Non-HR risk (SR + IR) (n = 63) | 23 (49%) | 40 (83%) | 0.0005 | 22 (49%) | 41 (82%) | 0.001 |
| T-ALL (n = 28) | 25 (53%) | 3 (6%) | | 15 (33%) | 13 (26%) | |
| B-ALL (n = 67) | 22 (47%) | 45 (94%) | 0 | 30 (67%) | 37 (74%) | NS |

Abbreviations:
ALL, acute lymphoblastic leukemia;
PPR, poor prednisone responders;
GPR, good prednisone responders;
BFM risk classification:
HR, high risk;
IR, intermediate risk;
SR, standard risk.
p-values were calculated using the Fischer's exact test.

Thus, the close correlation of various clinical ALL parameters to miR-151-5p and miR-451 suggest that these miRNAs play a role in ALL pathogenesis.

Example 3

Use of miR-151-5p and miR-451 for ALL Prognosis

Figure 1A:
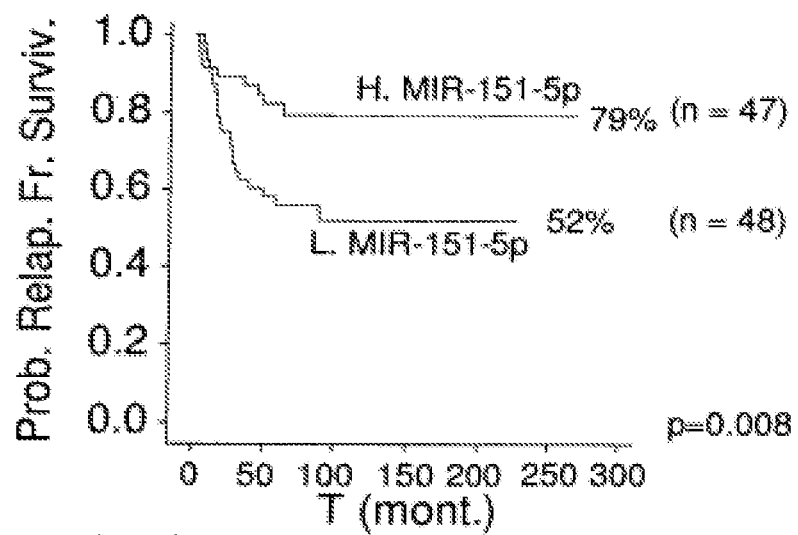
FIG. 1A-1C: Kaplan Meier estimation of Relapse Free Survival (RFS) in a cohort of 95 ALL patients. Probability of relapse-free survival in months from diagnosis commencement is shown.
Figure 1B:
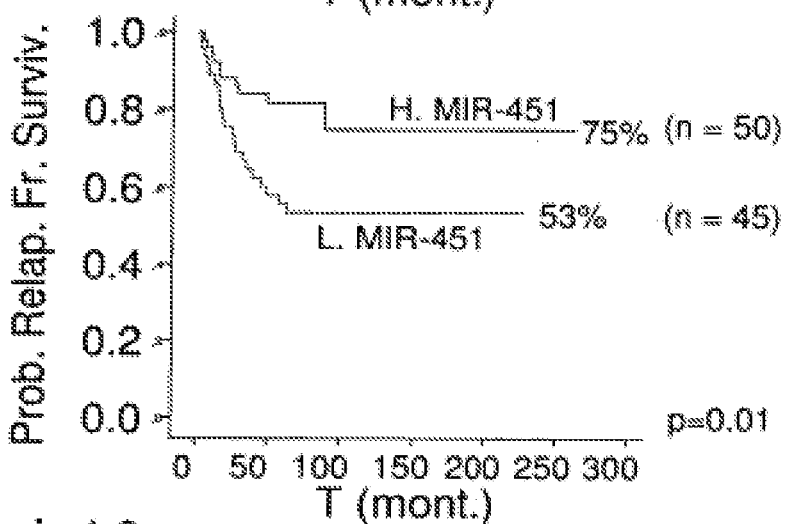
Figure 1C:
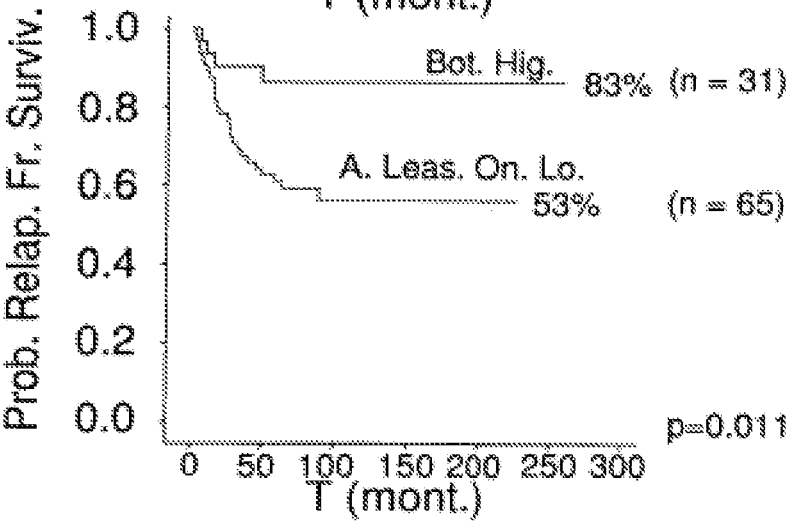

To determine whether expression levels of miR-151-5p and miR-451 are also significant in prediction of relapse free survival, a cohort of 95 patients was evaluated and samples were assigned as having either high or low miRNA based on the previously mentioned cutoffs. The probability of relapse free survival (RFS) was calculated for high and low miRNA using Kaplan Meier analysis, applying different weight to patient mortality according to the length of the preceding survival period. As shown by FIG. 1A, the RFS of patients with high miR-151-5p was 79% and 52% for patients with low miR-151-5p (p=0.008). FIG. 1B shows that RFS of patients with high miR-451 was 75% and 53% for patients with low miR-451 (p=0.01). FIG. 1C shows that when both miRNAs are combined, RFS of patients with high expression of both miRNAs was 83% compared to 53% if at least one of them was low (p=0.011).

When the 95-patient cohort is stratified based on clinical parameters, both miR-151-5p and miR-451 are capable of dividing the clinical group into subgroups. This separation was more significant in the more favorable groups, where high miRNA expression correlated with a much better RFS while low expression was a sign of poor clinical outcome. While in T-ALL, the general expression of miR-151-5p and miR-451 seemed to be very low, in B-ALL two clear groups can be identified. For this reason, the focus of the analysis was shifted to B-ALL only (n=67). In this group, lower expression of miR-151-5p and low expression of miR-451 only correlated with poor prednisone response and HR-classification, as illustrated by Table 2.

was 83% (7 relapses in 44 patients) and 39% for patients with low miR-151-5p (13 relapses in 23 patients), as demonstrated by FIG. 2A (p=0.001). FIG. 2B shows that RFS of patients with high miR-451 was 78% and 50% for patients with low miR-451 (p=0.002), and, finally, FIG. 2C shows that the RFS of patients expressing high levels of both miRNAs was 92% compared to 51% if at least one of them was low (p=0.002).

Example 4

The Combination of miR-151-5p and miR-451 is an Independent Risk-Factor

Multivariate Cox regression analysis revealed that combination of miR-151-5p and miR-451 as prediction markers for disease relapse can be regarded as independent risk-factor. A patient with at least one low miRNA had a relative risk of 5.64 (p=0.021) compared to BFM-HR that had a relative risk of 5.82 (p<0.000) to relapse, however, a patient that was defined as BFM-HR and had at least one low miRNA had a relative risk of 9 to relapse (p<0.000).

Example 5 miR-151-5p and miR-451 Enhance MRD-Based Prognosis

Minimal residual disease (MRD) is regarded as the most accurate prediction method of disease relapse. Therefore a cohort of 43 uniformly treated patients (INS-2003) that were classified by PCR-based MRD as non-HR was evaluated with regards to miR-151-5p and miR-451 expression levels. Patients within this group that had high miR-151-5p had RFS of 96% compared to those with low miR-151-5p who had a RFS of 75% (p=0.037, FIG. 3A). Neither miR-451 nor combination of miR-451 and miR-151-5p was significant. When only B-ALL were considered (n=32), the RFS of

TABLE 2

Correlation between miRNA expression level and clinical parameters in pediatric B-ALL

|  | miR-151-5p (n = 67) | | | miR-451 (n = 67) | | |
| --- | --- | --- | --- | --- | --- | --- |
|  | <cutoff (n = 23) | >cutoff (n = 44) | p-value | <cutoff (n = 30) | >cutoff (n = 37) | p-value |
| Age < 1 or Age > 6 (n = 30) | 12 (52%) | 18 (41%) |  | 13 (43%) | 17 (46%) |  |
| 1 < Age < 6 (n = 37) | 11 (48%) | 26 (59%) | NS | 17 (67%) | 20 (54%) | NS |
| Male (n = 34) | 13 (57%) | 21 (48%) |  | 15 (50%) | 19 (51%) |  |
| Female (n = 33) | 10 (43%) | 23 (52%) | NS | 15 (50%) | 18 (49%) | NS |
| WBC > 20000 (n = 21) | 11 (48%) | 10 (23%) |  | 12 (40%) | 9 (24%) |  |
| WBC < 2000 (n = 46) | 12 (52%) | 24 (77%) | NS | 18 (60%) | 28 (76%) | NS |
| PPR (n = 8) | 6 (26%) | 2 (5%) |  | 7 (23%) | 1 (3%) |  |
| GPR (n = 59) | 17 (74%) | 42 (95%) | 0.0164 | 23 (77%) | 36 (97%) | 0.0184 |
| High risk (HR + infant) (n = 18) | 11 (48%) | 7 (16%) |  | 13 (43%) | 5 (14%) |  |
| Non-HR risk (SR + IR) (n = 49) | 12 (52%) | 37 (84%) | 0.0085 | 17 (57%) | 32 (86%) | 0.0115 |

Abbreviations:
ALL, acute lymphoblastic leukemia;
PPR, poor prednisone responders;
GPR, good prednisone responders;
BFM risk classification:
HR, high risk;
IR, intermediate risk;
SR, standard risk.
P-values were calculated using the Fisher's exact test.

In this group, differences in RFS between low and high miRNAs became more significant. RFS of high miR-151-5p patients with high miR-151-5p was 100% compared to low miR-151-5p who had RFS of 69% (p=0.004, FIG. 3B). RFS of patients with high miR-451 was 100% compared to low miR-451 who had RFS of 75% (p=0.014, FIG. 3C). Combination of those two did not improve the results that were obtained by miR-151-5p on its own. Cox regression analysis revealed that miR-151-5p is an independent risk factor with relative risk of 14.48 to relapse (p=0.039).

Figure 4A:
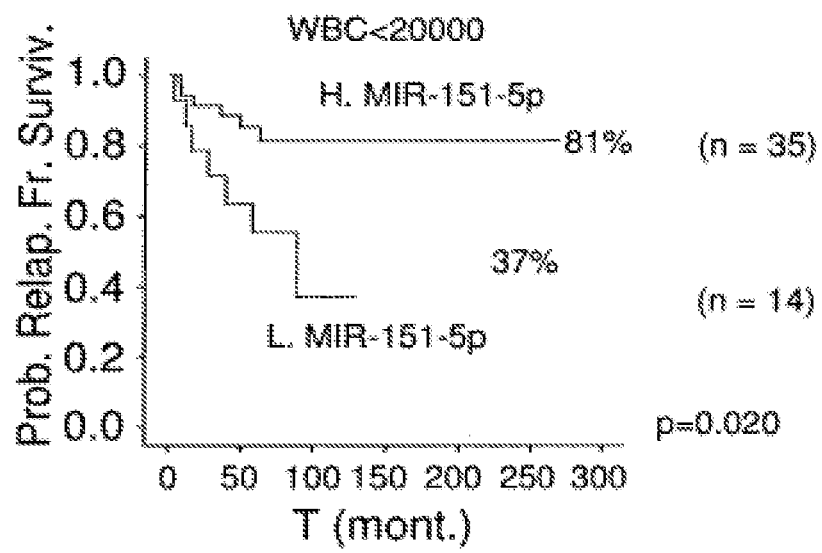
FIG. 4A-4B: Kaplan Meier estimation of Relapse Free Survival (RFS) by miR-151-5p expression in a cohort of ALL and B-ALL patients classified according to favorable prognostic factors. Probability of relapse-free survival in months from diagnosis commencement is shown.
Figure 4B:
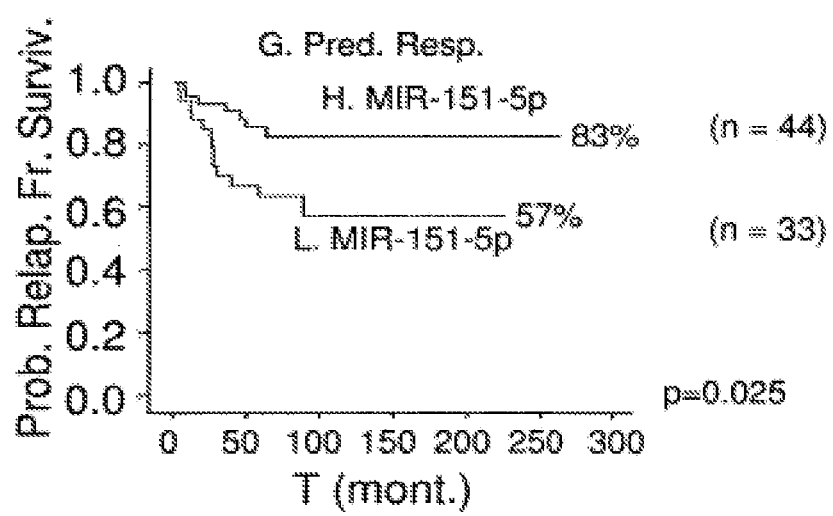

Example 6 miR-151-5p can Distinguish Two Subgroups within the Favorable Clinical Prognostic Groups One important object of the present Invention is providing better tools for prediction of relapse in ALL patients. This is especially important in the case of patients displaying favorable clinical prognostic parameters, where current conventional prognostic tools predict a good outcome. Such a prognosis may lead to a decision to avoid over-treatment, and if wrong, the decision may lead to relapse. Therefore, precise prognostic tools are required. FIG. 4 demonstrates that miR-151-5p expression values can discern between low and high RFS within ALL patients groups showing good clinical parameters. FIG. 4A shows that in patients with WBC count under 20,000 (n=49), high miR-151-5p expression correlates with RFS at 81% (6 relapses in a group of 35 patients), whereas low miR-151-5p expression correlates with RFS at 37% (7 relapses in a group of 14 patients) (p=0.02). FIG. 4B shows that in patients with a good prednisone response (n=77), high miR-151-5p expression correlates with RFS at 83% (7 relapses in a group of 44 patients), whereas low miR-151-5p expression correlates with RFS at 57% (13 relapses in a group of 33 patients) (p=0.025). As indicated earlier in Example 3, FIG. 2A illustrates that within the entire B-ALL patients group, high miR-151-5p expression correlates with RFS at 83%, whereas low miR-151-5p expression correlates with RFS at 39% (p=0.001).

Figure 5A:
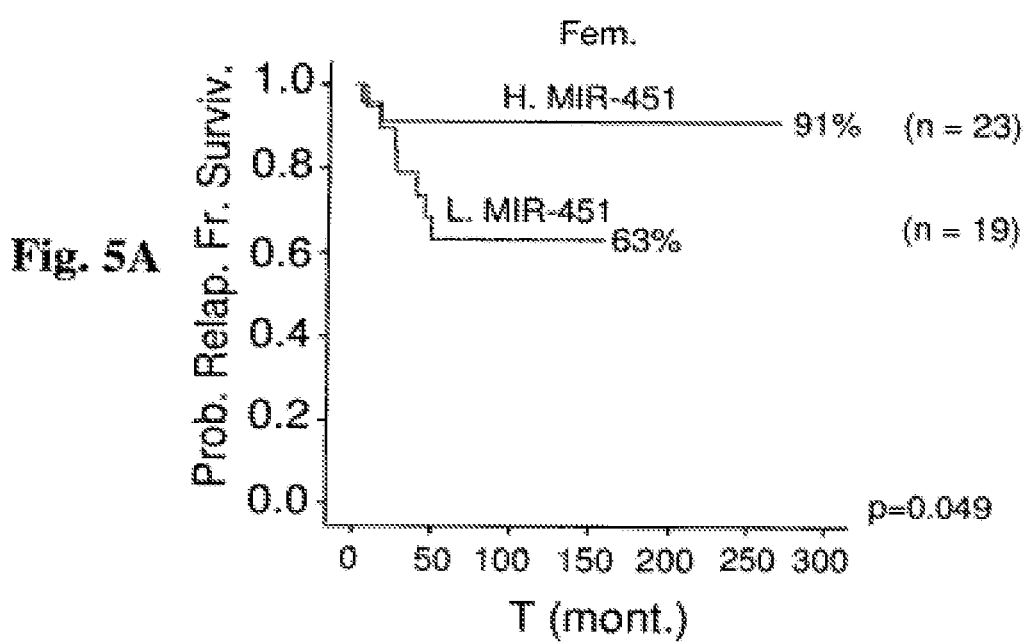
Figure 6A:
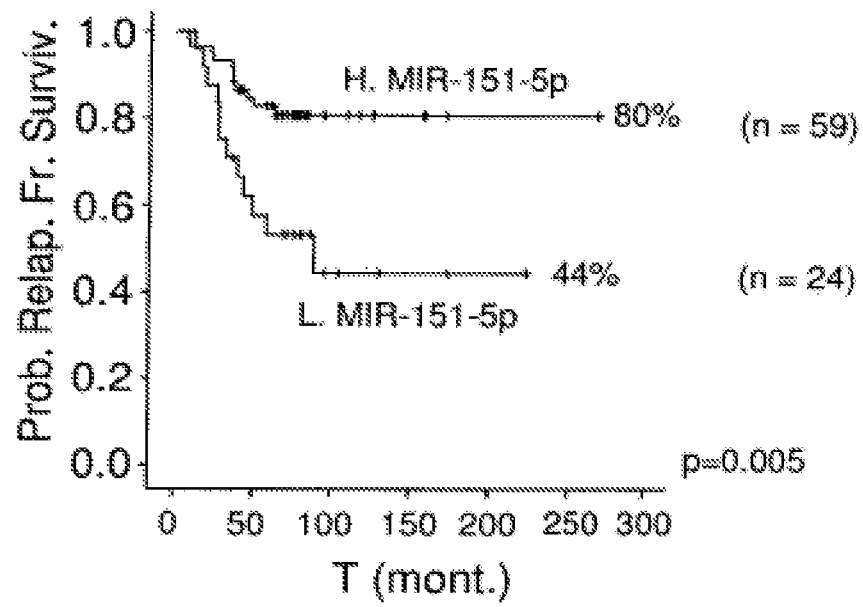
FIG. 6A-6D: Prognostic relevance of miR-151-5p and miR-451 expression in an extended cohort Probability of relapse-free survival in months from diagnosis commencement is shown. The figure provides an analysis of the original patient population (which is presented in FIG. 2) augmented by the addition of more patients (extended cohort).
Figure 6B:
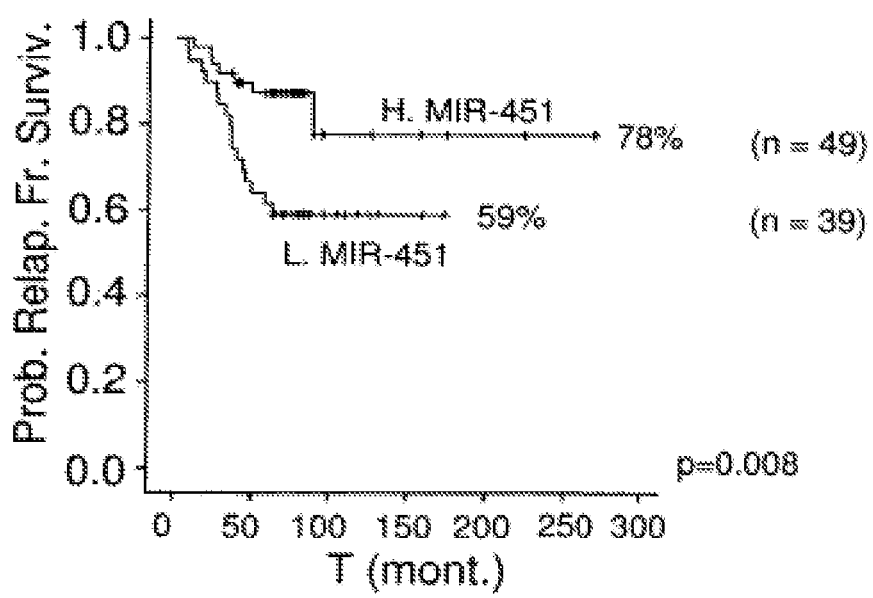
Figure 6C:
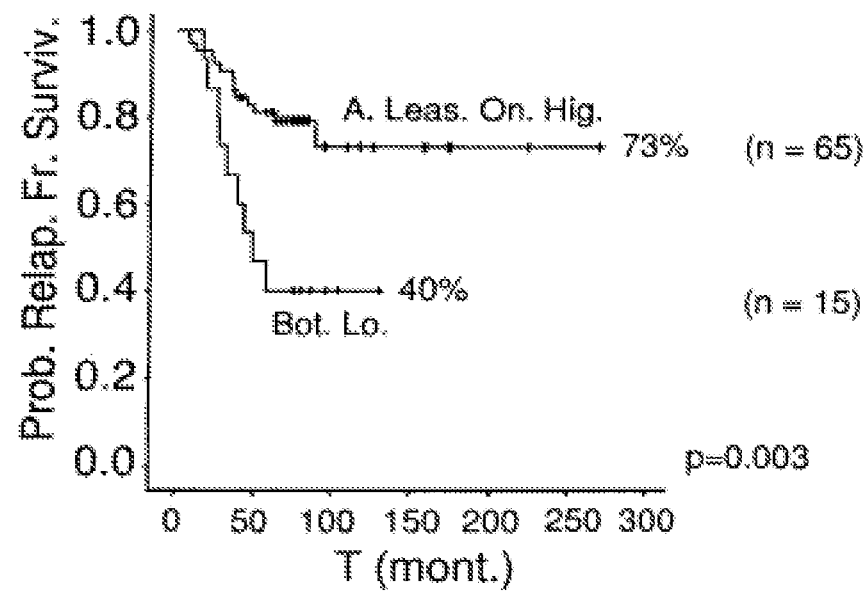
Figure 6D:
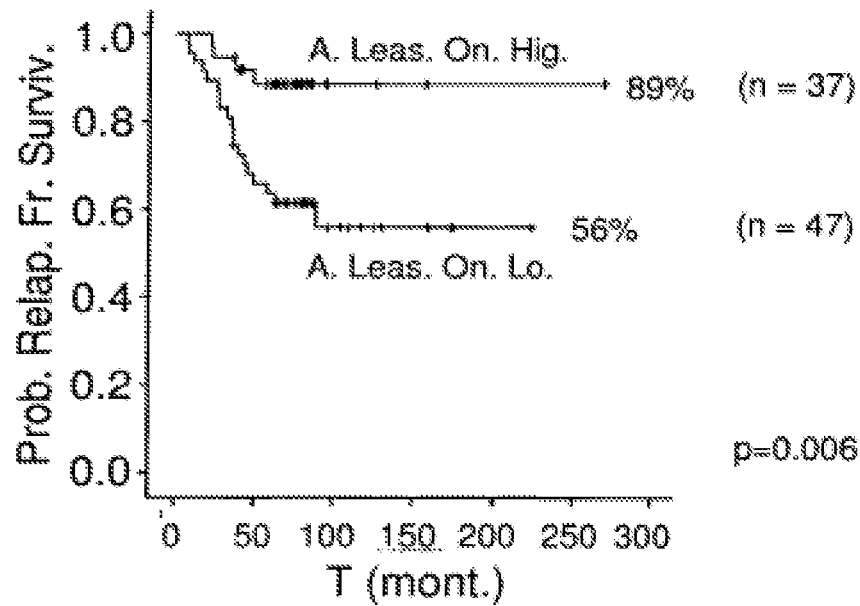

Example 7 miR-451 can Distinguish Two Subgroups within the Favorable Clinical Prognostic Groups Similarly to miR-151-5p, miR-451 also provides a sharp dissection tool for better RFS prognosis for patient groups displaying favorable clinical prognostic parameters. FIG. 5A shows that in female patients (n=42), high miR-451 expression correlates with RFS at 91% (2 relapses in 23 patients), whereas low miR-451 expression correlates with RFS at 63% (7 relapses in 19 patients) (p=0.049). FIG. 5B shows that in patients with a good prednisone response (n=77), high miR-451 expression correlates with RFS at 79% (7 relapses in 46 patients), whereas low miR-451 expression correlates with RFS at 58% (13 relapses in 31 patients) (p=0.014). FIG. 5C shows that in patients with a WBC count under 20,000 (n=49), high miR-451 expression correlates with RFS at 74% (4 relapses in 29 patients), whereas low miR-151-5p expression correlates with RFS at 55% (9 relapses in 20 patients) (p=0.023). As indicated earlier in Example 3, FIG. 2B illustrates that within the entire B-ALL patients group, high miR-451 expression correlates with RFS at 78%, whereas low miR-451 expression correlates with RFS at 50% (p=0.002).

Example 8

Prognostic Relevance of miR-151-5p and miR-451 Expression in an Extended Cohort

In the course of their investigations, the inventors received further samples and decided to include said samples into an extended cohort which will facilitate an even more accurate analysis of the prognostic capability of the invention.

Twenty-seven additional samples of B-ALL patients undergoing the same treatment regimen as the patients treated in Schneider Children's Medical Center of Israel and described in the previous Examples (BFM), were obtained from Prague. The new, extended B-ALL cohort was re-analyzed.

The B-lineage group consisted of 67 patients treated at Schneider Children's Medical Center of Israel and 27 patients treated at the University Hospital Motol, Prague. Of this group, Philadelphia positive patients (n=3) were excluded from further analysis. Low expression of miR-151-5p or miR-451 independently, or in a combination of both together, or of at least one of them resulted in poor RFS (44%, 59%, 40% and 56%, respectively) compared to significantly higher RFS rates when the miRNAs' expression was high (80%, 78%, 73% and 89% and p=0.005, 0.008, 0.003 and 0.006, respectively), as seen in FIGS. 6A-6D.

When the cohort was stratified according to the well established PCR-MRD risk analysis, expression level of both miRNAs together could divide the PCR-MRD intermediate risk group into 2 distinct subgroups with different outcome, respectively. As demonstrated in FIGS. 7A and 7B, patients expressing low levels of both miRNAs together had a poor RFS (50% and 0%, respectively) versus significantly higher RFS rates when miR-451 or both were highly expressed (92% and 87% and p=0.004 and 0.002, respectively; FIGS. 7A and 7B). Cox regression analysis including PCR-MRD, low expression of both miRNAs, low expression of at least one microRNA, age, WBC and PR, identified low expression of both miRNAs as an independent prognostic marker with an increased risk for relapse of 9 (p=0.006; see Table 3), in addition to PCR-MRD. When analyzing each miRNA separately, only miR-151-5p was detected as an independent prognostic marker with an increased risk for relapse of 5.9 (p=0.025), in addition to PCR-MRD.

TABLE 3

Univariate and multivariate Cox regression analyses for relapse in the B-lineage ALL cohort

|  |  | Multivariate | | |
| --- | --- | --- | --- | --- |
| Variant | Univariate P | P | RR | 95% CI |
| Low expression of both miRs | 0.022 | 0.006 | 9 | 1.9-44 |
| Low expression of at least one miR | 0.051 | | | |
| PCR-MRD | 0.005 | 0.003 | 5.9 | 1.8-19 |
| Age | NS | | | |
| WBC | NS | | | |
| Prednisone response | NS | | | |

Low expression of both miRs (miR-151-5p, miR-451) was defined as miR expression values under or equal to the cutoff of both miRs. Low expression of at least one miRs (miR-151-5p, miR-451) was defined as miR expression values under or equal to the cutoff of either miR. PCR-MRD risk groups were defined according to BFM-2000.

Abbreviations: RR (relative risk); CI (confidence interval).

Example 9

Prognostic Relevance of miR-151-5p and miR-451 Expression in the Extended Cohort Excluding Patients with Ikaros Deletion or P2RY8-CRLF2 Rearrangement A deletion of the IKZF1 gene and the P2RY8-CRLF2 rearrangement have recently been shown to be associated with poor prognosis in B-lineage ALL [Mullighan C. G. et al., N. Eng. J. Med. 360:470-480 (2009); Kuiper R. P. et al., Leukemia 24:1258-1264 (2010); Cario G. et al., Blood 115:5393-5397 (2010)]. However, they are not included in the risk stratification. Thus, the inventors next assessed the effect of exclusion of patients harboring the known adverse prognostic genetic parameters including Ikaros deletion and P2RY8-CRLF2 rearrangement.

Kaplan Meier analysis was performed again on a uniform cohort of B-lineage ALL with no Ikaros deletion or P2RY8-CRLF2 rearrangement (n=50). The expression of miR-151-5p significantly correlated with prognosis. Patients with low expression had a 65% RFS versus 91% RFS in the group with high miR-151-5p expression (p=0.043; FIG. 8). Multivariate analysis including expression of both microRNAs, at least one, age, WBC and PCR-MRD identified the expression of both microRNAs as an independent prognostic marker with an increased relative risk of 22 to relapse (p=0.017) in addition to PCR-MRD, as shown in Table 4.

TABLE 4

Univariate and multivariate Cox regression analyses for relapse in the B-lineage ALL cohort excluding patients with Ikaros deletion or P2RY8-CRLF2 rearrangement

| Variant | Univariate P | Multivariate P | RR | 95% CI |
|---|---|---|---|---|
| Low expression of both miRs | 0.054 | 0.017 | 22 | 1.7-284 |
| Low expression of at least one miR | 0.058 | | | |
| PCR-MRD | 0.035 | 0.021 | 18 | 1.6-200 |
| Age | NS | | | |
| WBC | NS | | | |
| Prednisone response | NS | | | |

Low expression of both miRs (miR-151-5p, miR-451) was defined as miR expression values under or equal to the cutoff of both miRs. Low expression of at least one miR (miR-151-5p, miR-451) was defined as miR expression values under or equal to the cutoff of either miRs. PCR-MRD risk groups were defined according to BFM-2000.

Abbreviations: RR (relative risk); CI (confidence interval).

The presented results demonstrate that miR-151-5p and miR-451 can serve as novel biomarkers for prediction of outcome and treatment response in pediatric B precursor acute lymphoblastic leukemia, treated according to BFM-based protocols, on top of the PCR-MRD classification. Low expression levels of both miRNAs can identify true high-risk patients, within the non-high risk group. These high risk patients cannot be identified to date since they do not harbor any of the known adverse genetic abnormalities such as the Philadelphia chromosome, IKZF1 deletion or CRLF2 rearrangement.

Example 10

Validation of miR-451 as a Relapse Prognostic Marker in Patients Undergoing a Different Treatment Regimen The inventors obtained 35 B-ALL samples from the Netherlands, of patients receiving the Dutch Childhood Oncology Group (DCOG) protocol ALL-9. The expression levels of miR-151 and miR-451 was determined in these samples. FIG. 9 illustrates that although the follow up is still short, miR-451 could identify patients with 100% RFS (high expression) versus 40% in the low expressing patients (p=0.003).

This result emphasizes that the findings of the inventors that miR-451 can serve as a biomarker predicting relapse in B-ALL, are not confined only to the BFM protocol and are independent of the treatment regimen.

Example 11 miR-151-5p and miR-451 Expression During Follow Up

In order to better characterize the expression pattern of miR-151-5p and miR-451 throughout the treatment process, the inventors collected samples from four patients (thus far) and determined their miR-151-5p and miR-451 levels. Two patients relapsed (A and B) and 2 patients are well during a long follow up (C and D)

Patient A

The expression levels of miR-151-5p and miR-451 were measured in 5 samples collected from this patient:
Sample 1: at diagnosis (AD); sample 2: day 42 from AD; sample 3: 15 months from AD; sample 4: Relapse sample 22 months from AD; sample 5: 2 months post relapse and 24 months from AD. This patient relapsed again at 26 months from AD in the central nervous system (CNS).

Following treatment, there was a 2- and 4-log increase in the expression levels of miR-451 after day 42 and 15 months, respectively. However, there was a reduction of 2-logs in the relapse sample and this reduction continued, since this patient underwent an additional relapse 2 months later as illustrated in FIG. 10A. miR-151-5p exhibited a similar trend with smaller differences.

Patient B

The expression levels of miR-151-5p and miR-451 were measured in 5 samples from this patient:
Sample 1: at diagnosis (AD); sample 2: 5 months from AD; sample 3: 37 months from AD; sample 4: Relapse sample 45 months from AD; sample 5: 2 months post relapse and 47 months from AD.

Following treatment, there was a 3 log increase in the expression levels of miR-451 after 5 months. However, there was a reduction of 2 logs in the sample prior to relapse (8 months prior to relapse) this downward trend continued and an additional reduction of 1.5 logs was measured in the relapse sample. Two months following relapse there was an increase in the levels of almost 2 logs (see FIG. 10B). miR-151-5p exhibited a similar trend with smaller differences.

These results suggest that miR-451 and miR-151-5p can be used to monitor follow up samples. The changes in expression levels can identify occult relapse, prior to the full blown relapse.

Patients C and D (Non-Relapse Patients)

The inventors evaluated the expression pattern of miR-151-5p and miR-451 in two non-relapse patients (patient C and D, as shown in FIGS. 10C and 10D, respectively) during lengthy follow up periods (180 and 224 months from diagnosis, respectively). In patient C, the expression levels of miR-151-5p remained steady and started to increase 19 months post-diagnosis.

A similar expression pattern was observed in the case of Patient D, which suffered from T-ALL. The expression levels of miR-151-5p increase until an increase of 1 log was reached 20 months post-diagnosis.

These results suggest that miR-451 and miR-151-5p can be used to monitor follow up samples. The changes in expression levels can identify occult relapse, prior to the full blown relapse. As demonstrated the marker miRNAs expression patterns can effectively discern between non-relapsing and relapsing patients.

We claim:

1. A method of treatment for acute lymphoblastic leukemia (ALL) in a mammalian subject, comprising:
   (a) contacting a test sample from the subject with nucleic acid molecules specific for miR-451, or miR-451 and miR-151-5p;
   (b) determining the expression value of the miR-451, or miR-451 and miR-151-5p in the test sample;
   (c) comparing the expression value of the miR-451, or miR-451 and miR-151-5p in the test sample with a control value of miR-451, or miR-451 and miR-151-5p; wherein lower expression of miR-451, or miR-451 and miR-151-5p in the test sample in comparison to the control indicates that the subject has an increased risk of ALL relapse; and
   (d) if the subject does not have an increased risk of ALL relapse, administering to the subject a standard risk ALL treatment regimen selected from the group consisting of standard risk regimens of COG, ACS, BFM, and UKALL2003;
   and if the subject has an increased risk of ALL relapse administering to the subject a high risk ALL treatment regimen selected from the group consisting of high risk regimens of COG, ACS, BFM, and UKALL2003.

2. The method of claim 1, wherein the ALL is B-ALL.

3. The method of claim 1, further comprising
   (e) repeating steps (a) to (c) with a temporally-separated test sample from the subject, wherein a decrease over time in the expression of miR-451, or miR-451 and miR-151-5p between the temporally-separated test samples, in comparison to the control expression, indicates that the subject is in relapse; and
   (f) adjusting the treatment provided to the patient in step (d) to treat the relapsed subject.

4. The method of claim 1, wherein (a) further comprises contacting the test sample with a nucleic acid specific to a control gene or miRNA; wherein (b) further comprises determining the expression of the control gene or miRNA; and before (c), further comprising normalizing the expression value of miR-451, or miR-451 and miR-151-5p according to the expression of the control gene or miRNA, and wherein the normalized expression value of miR-451, or miR-451 and miR-151-5p in the test sample is used in step (c) for comparison with the control expression value of miR-451, or miR-451 and miR-151-5p.

5. The method of claim 1, wherein the risk of ALL relapse in the subject is further correlated with ALL-associated clinical criteria selected from the group consisting of: B-ALL and T-ALL diagnosis, minimal residual disease (MRD) high and low risk definitions, response to prednisone on day 8 of treatment; BFM high and low risk definitions, white blood count (WBC) being over or below 20,000 cells/ml, patient age, CCG high and low risk definitions, and gender.

6. The method of claim 1, wherein the subject has been diagnosed with B-ALL.

7. The method of claim 1, wherein the test sample is isolated from bone marrow or blood of the subject.

* * * * *